United States Patent
Dubreuil et al.

(10) Patent No.: US 10,509,035 B2
(45) Date of Patent: Dec. 17, 2019

(54) ANTIBODIES, ANTIBODY DRUG CONJUGATES AND METHODS OF USE

(71) Applicant: GAMAMABS PHARMA, Toulouse (FR)

(72) Inventors: Olivier Dubreuil, Toulouse (FR); Jean-Marc Barret, Toulouse (FR); Jean-François Prost, Toulouse (FR); Delphine Desigaud, Toulouse (FR)

(73) Assignee: GAMAMABS PHARMA SA, Toulouse (FR)

( * ) Notice: Subject to any disclaimer, the term of this patent is extended or adjusted under 35 U.S.C. 154(b) by 0 days.

(21) Appl. No.: 15/229,307

(22) Filed: Aug. 5, 2016

(65) Prior Publication Data

US 2017/0035903 A1   Feb. 9, 2017

Related U.S. Application Data

(60) Provisional application No. 62/202,396, filed on Aug. 7, 2015.

(51) Int. Cl.
| G01N 33/574 | (2006.01) |
| C07K 16/28  | (2006.01) |
| A61K 51/10  | (2006.01) |
| A61K 47/68  | (2017.01) |

(52) U.S. Cl.
CPC ... *G01N 33/57415* (2013.01); *A61K 47/6803* (2017.08); *A61K 47/6849* (2017.08); *A61K 47/6869* (2017.08); *A61K 51/1036* (2013.01); *A61K 51/1093* (2013.01); *C07K 16/2869* (2013.01); *G01N 33/57434* (2013.01); *G01N 33/57442* (2013.01); *G01N 33/57449* (2013.01); *C07K 2317/24* (2013.01); *C07K 2317/41* (2013.01); *C07K 2317/73* (2013.01); *C07K 2317/77* (2013.01); *C07K 2317/92* (2013.01); *G01N 2333/72* (2013.01)

(58) Field of Classification Search
None
See application file for complete search history.

(56) References Cited

U.S. PATENT DOCUMENTS

| 5,202,238 A | 4/1993 | Fell, Jr. et al. |
| 5,204,244 A | 4/1993 | Fell et al. |
| 5,208,020 A | 5/1993 | Chari et al. |
| 5,225,539 A | 7/1993 | Winter |
| 5,416,064 A | 5/1995 | Chari et al. |
| 5,475,092 A | 12/1995 | Chari et al. |
| 5,500,362 A | 3/1996 | Robinson et al. |
| 5,530,101 A | 6/1996 | Queen et al. |
| 5,565,332 A | 10/1996 | Hoogenboom et al. |
| 5,585,089 A | 12/1996 | Queen et al. |
| 5,585,499 A | 12/1996 | Chari et al. |
| 5,821,337 A | 10/1998 | Carter et al. |
| 5,846,545 A | 12/1998 | Chari et al. |
| 5,994,524 A | 11/1999 | Matsushima et al. |
| 6,333,410 B1 | 12/2001 | Chari et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,441,163 B1 | 8/2002 | Chari et al. |
| 6,534,660 B1 | 3/2003 | Yongxin et al. |
| 6,596,757 B1 | 7/2003 | Chari et al. |
| 6,630,579 B2 | 10/2003 | Chari et al. |
| 6,756,397 B2 | 6/2004 | Zhao et al. |
| 7,276,497 B2 | 10/2007 | Chari et al. |
| 8,236,319 B2 | 8/2012 | Chari et al. |
| 8,278,423 B2 | 10/2012 | Teulon et al. |
| 9,012,607 B2 * | 4/2015 | Behrens ............... A61K 33/24 530/387.1 |
| 9,150,649 B2 | 10/2015 | Singh et al. |
| 9,458,239 B2 * | 10/2016 | Teulon ............... C07K 16/2869 |
| 9,511,138 B2 * | 12/2016 | Gaucher .......... A61K 39/39533 |
| 9,637,544 B2 * | 5/2017 | Behrens ............... A61K 31/282 |
| 10,179,816 B2 * | 1/2019 | Gaucher .......... A61K 39/39533 |
| 2005/0169933 A1 | 8/2005 | Steeves et al. |

(Continued)

FOREIGN PATENT DOCUMENTS

| EP | 0 239 400 | 8/1994 |
| EP | 0 125 023 | 3/2002 |

(Continued)

OTHER PUBLICATIONS

Casadevall et al (PNAS 109(31):12272-12273, 2012).*
Caldas et al (Molecular Immunology 39:941-852, 2003).*
Panowski, S. et al. "Site-specific antibody drug conjugates for cancer therapy" *Landes Bioscience*, Jan./Feb. 2014, pp. 34-45, vol. 6, No. 1.
Peters, C. et al. "Antibody-drug conjugates as novel anti-cancer chemotherapeutics" *Bioscience Reports*, 2015, pp. 1-20, vol. 35.
Badescu, G. et al. "Bridging Disulfides for Stable and Defined Antibody Drug Conjugates" *Bioconjugate Chemistry*, May 3, 2014, pp. 1124-1136, vol. 25.

(Continued)

*Primary Examiner* — Patricia Duffy
(74) *Attorney, Agent, or Firm* — Saliwanchik, Lloyd & Eisenschenk

(57) ABSTRACT

This invention relates to antibody drug conjugates (ADC), antibody conjugates (AC) and novel antibodies. Particularly, the ADC, AC and antibodies disclosed herein specifically bind to the human anti-Müllerian hormone type II receptor (AMHR-II) and can be used to treat and/or identify AMHR-II expressing cancers, such as prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma.

9 Claims, 22 Drawing Sheets
(8 of 22 Drawing Sheet(s) Filed in Color)
Specification includes a Sequence Listing.

(56) References Cited

U.S. PATENT DOCUMENTS

2015/0004156 A1 1/2015 Gaucher et al.
2015/0125473 A1 5/2015 Burt et al.

FOREIGN PATENT DOCUMENTS

| EP | 0 592 106 | 11/2004 |
| EP | 0 519 596 | 2/2005 |
| EP | 0 770 628 | 9/2006 |
| EP | 2 097 453 | 3/2011 |
| WO | WO 91/09967 | 7/1991 |
| WO | WO 94/11026 | 5/1994 |
| WO | WO 96/02576 | 2/1996 |
| WO | WO 2005/007197 | 1/2005 |
| WO | WO 2008/053330 | 5/2008 |
| WO | WO 2010/100430 | 9/2010 |
| WO | WO 2011/141653 | 11/2011 |
| WO | WO 2013/093379 | 6/2013 |

OTHER PUBLICATIONS

Chari, R.V.J. et al. "Antibody-Drug Conjugates: an Emerging Concept in Cancer Therapy" *Angewandte Chemie International Edition*, 2014, pp. 3796-3827, vol. 53.

Iamele, L. et al. "Antibody-drug conjugates: targeted weapons against cancer" *Antibody Technology Journal*, 2015, pp. 1-13, vol. 5.

Sassoon, I. et al. "Antibody-Drug Conjugate (ADC) Clinical Pipeline: A Review", Chapter 1 in *Antibody-Drug Conjugates, Methods in Molecular Biology* 1045, ed. Laurent Ducry, Humana Press, 2013, pp. 1-27.

\* cited by examiner

| VH domain | SEQ ID | FR1 (1-25) | CDR1 (26-35) | FR2 (36-49) | CDR2 (50-65) | FR3 (66-94) | CDR3 (95-102) | FR4 (103-113) |
|---|---|---|---|---|---|---|---|---|
| 3C23K | 19 | QVRLVQSGAEVKKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| 3C23KR | 20 | QVQLVQSGAEVKKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| 5B42 | 21 | QVQLVQSGAEVKKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| K4D24 | 22 | RVRLVQSGAEVKKPGASVKVSC | KASGYTFTSYHIH | WVRQAPGQRLEWMG | WIYPGDDSTKYSQKFQG | RVTITRDASASTAYMELSSLRSEDTAVYYCTR | GDRF---AY | WGQGTLVTVSS |
| K4D20 | 23 | QVRLVQSGAEVKKPGASVKVSC | KASGYTFTSNHIH | WVRQAPGQRLEWMG | WIYPGDDSTKYSQKFQG | RVTITRDTSASTAYMELSSLRSEDTAVYYCTR | GDRF---AY | WGQGTLVTVSS |
| K4A12 | 24 | QVRLVQSGAEVKKPGTSVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| K5D05 | 25 | QVRLVQSGAEVKKPGASVKVSC | KASGYTFTGYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| K5D14 | 26 | QVRLVQSGAEVKKPGASVKVSC | KASGYTSFTSYHIH | WVRQAPGQSLEWMG | WIYPGDDSTKYSQKFQG | RVTITRDTSASTAYMELSSLRSEDTAVYYCTR | GDRF---AY | WGQGTLVTVSS |
| K4D123 | 27 | QVRLVQSGAEVKKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| K4D127 | 28 | QVRLVQSGAEVKKPGASVKVSC | KASGYTFTSYHIH | WVRQAPGQRLEWMG | WIYPGDDSTKYSQKFQG | RVTFTRDTSASTAYMELSSLRSEDTAVYYCTR | GDRF---AY | WGQGTLVTVSS |
| 5C14 | 29 | QVRLVQSGAEVKKPGASVKVSC | KASGYTFTSYHIH | WVRQAPGQRLEWMG | WIYPGDDSTKYSQKFQG | RMTITRDTSASTAYMELSSLRSEDTAVYYCTR | GDRF---AY | WGQGTLVTVSS |
| 5C26 | 30 | QVRLVQSGAEVKKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| 5C27 | 31 | QVRLVQSGAEVKKPGASVKVSC | KASGYTFTSYHIH | WVRQAPGQRPEWMG | WIYPGDDSTKYSQKFQG | RVTITRDTSASTAYMELSSLRSEDTAVYYCTR | GDRF---AY | WGQGTLVTVSS |
| 5C60 | 32 | QVRLVQSGAKVRKPGASVKVSC | KASGYTFTSYHIH | WVRQAPGQRLEWMG | WIYPGDDSTKYSQKFQG | RVTITRDTSASTAYMELSSLRSEDTAVYYCTR | GDRF---AY | WGQGTLVTVSS |
| 6C13 | 33 | QVRLVQSGAEVKKPGASVKVSC | KASGYTFTSYHIH | WVRQAPGQRLEWMG | WIYPEDDSTKYSQKFQG | RVTITRDTSASTAYMELSSLRSEDTAVYYCTR | GDRF---AY | WGQGTLVTVSS |
| 6C18 | 34 | QVRLVQSGAEVKKPGASVKVSC | KASGYTFTSYHIH | WVRQAPGQRLEWMG | WIYPGDDSTKYSQKFQG | PVTITRDTSASTAYMELSSLRSEDTAVYYCAR | GDRF---AY | WGQGTLVTVSS |
| 6C54 | 35 | QVRLVQSGAEVKKPGASVKVSC | KASGYTFTSYHIH | WVRQAPGQRLEWMG | WIYPGDDSTKYSQKFQG | RVTIRDTSASTAYMELSSLRPEDTAVYYCTR | GDRF---AY | WGQGTLVTVSS |

FIGURE 14A

| VL domain | SEQ ID | FR1 (1-23) | CDR1 (24-34) | FR2 (35-49) | CDR2 (50-56) | FR3 (57-88) | CDR3 (89-97) | FR4 (98-107) |
|---|---|---|---|---|---|---|---|---|
| 3C23K | 36 | DIQMTQSPSTLSASVGDRVTITC | RASSS-VRYIA | WYQQKPGKAPKLLIY | PTSSLKS | GVPSRFSGSGSGTEFTLTISSLQPDDFATYYC | LQWSSYPWT..ab | FGGGTKVEIK |
| 3C23 | 37 | DIQMTQSPSTLSASVGDRVTITC | RASSS-VRYIA | WYQQKPGKAPKLLIY | PTSSLES | GVPSRFSGSGSGTEFTLTISSLQPDDFATYYC | LQWSSYPWT | FGGGTKVEIK |
| 6B78 | 38 | DIQMTQSPSTLSASVGDRVTITC | RASSS-VRYIA | WYQQKPGKAPKLLIY | STSSLKS | GVPSRFSGSGSGTEFTLTISSLQPDDFATYYC | LQWSSYPWT | FGGGTKVEIK |
| 5B42 | 39 | DIQMTQSPSTLSASVGDRVTITC | RASSS-VRYIA | WYQQKPGKAPKLLIY | PTSSLES | GVPSRFSGSGSGTEFTLTISSLQPDDFATYYC | LQWSSYPWT | FGGGTKVEIK |
| 6C59 | 40 | DIQMTQSPSTLSASVGDRVTITC | RASPP-VRYIA | WYQQKPGKAPKLLIY | PTSSLKS | GVPSRFSGSGSGTEFTLTISSLQPDDFATYYC | LQWSSYPWT | FGGGTKVEIK |
| 6C07 | 41 | DIQMTQSPSTLSASVGDRVAITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 5C10 | 42 | DIQMTQSPSTLSASVGDRVTITC | RASPS-VRYIA | WYQQKPGKAPKLLTY | PTSSLKS | GVPSRFSGSGSGTEFTLTISSLQPDDFATYYC | LQWSSYPWT | FGGGTKVEIK |
| 6C54 | 43 | DIQLTQSPPTLSASVGDRVTITC | RASSS-VWYIA | WYQQKPGKAPKLLTY | PTSSLKS | GVPSRFSGSGSGTEFTLTISSLQPDDFATYYC | LQWSSYPWT | FGGGTKVEIK |
| K4D25 | 44 | DIQLLTQSPSTLSASVGDRVTITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| K4A03 | 45 | DIQMTQSPSTLPASVGDRVTITC | RASSS-VRYTA | WYQQKPGKAPKLLTY | PTSSLKS | GVPSRFSGSGSGTEFTLTISSLQPDDFATYYC | LQWSSYPWT | FGGGTKVEIK |
| K4A08 | 46 | DIQLTQSPSTLSASVGDRATITC | RASSS-VRYIA | WYQQEPGKAPKLLTY | PTSSLKS | GVPSRFSGSGSGTEFTLTISSLQPDDFATYYC | LQWSSYPWT | FGGGTKVEIK |
| K5D26 | 47 | DIQMTQSPSTLSASVGDRVTIPC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 5C08 | 48 | DIQMTQSPSTLSASVGDRVTITC | RASSS-VRDIA | WYHQKPGKAPKLLTY | PTSSLKS | GVPSRFSGSGSGTEFTLTISSLQPDDFATYYC | LQWSSYPWT | FGGGTKVEIK |
| 5C18 | 49 | DIQMTQSPSTLSASVGDRVTITC | RASSS-VRYIA | WYQQKPGKAPKLLTY | PTSSLKS | GVPSRFSGSGSGTEFTLTISSLQPDDFATYYC | LQWSSYPWT | FSGGTKVEIK |
| 5C42 | 50 | DIQMTQSPSTLSASVGDRVTITC | RASSS-VRYIA | WYQQKPGKAPKLLTY | PTSSLKS | GVPSRFCGSGSGTEFTLTISSLQPDDFATYYC | LQWSSYPWT | FGGGTKVEIK |
| 5C44 | 51 | DIQMTQSPSTLPASVGDRVTITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 5C52 | 52 | DIQMTQSPSTLSASVGDRATITC | RASSS-VRYIA | WYQQKPGKAPKLLTY | PTSSLKS | GVPSRFSGSGSGTEFALTISSLQPDDFATYYC | LQWSSYPWT | FGGGTKVEIK |
| 5C56 | 53 | DIQMTQSPSTLSASVGDRVTITC | RASSS-VRYIA | WYQQMPGKAPKLLTY | PTSSLKS | GVPSRFSGSGSGTEFTLTISSLQPDDFATYYC | LQWSSYPWT | FGGGTKVEIK |
| 6C03 | 54 | DIQMTQSPSTLSASVGDRVTITC | RASSS-VWYIA | WYQQKPGKAPKLLTY | PTSSLKS | GVPSRFSGSGSGTEFTLTISSLQPDDFATYYC | LQWSSYPWT | FGGGTKVEIK |
| 6C05 | 55 | DIQLTQSPSTLSASVGDRVTITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 6C16 | 56 | DNQMTQSPSTLSASVGDRVTITC | RASSS-VRYIA | WYQQKPGKRAPKLLTY | PTSSLKS | GVPSRFSGSGSGTEFTLTISSLQPDDFATYYC | LQWSSYPWT | FGGGTKVEIK |
| 6C17 | 57 | DIQMTQSPSTLSASVGDRVTITC | RASSS-VGYIA | WYQQKPGKAPKLLTY | PTSSLKS | GVPSRFSGSGSGTEFTLTISSLQPDDFATYYC | LQWSSYPWT | FGGGTKVEIK |
| 6C28 | 58 | DIQMTQSPSTLSASVGDRVTITC | RASSS-VRYIA | WYQQKPGKAPKLLTH | PTSSLKS | GVPSRFSGSGSGTEFTLTISSLQPDDFATYYC | LQWSSYPWT | FGGGTKVEIK |
| 725C02 | 59 | DIQMTQSPSTLSASVGDRVTITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 725C17 | 60 | DTQMTQSPSTLSASVGDRVTITC | RASSS-VRYIA | WYQQKPGKAPKLLTY | PTSSLKS | GVPSRFSGSGSGTEFTLTFSSLQPDDFATYYC | LQWSSYPWT | FGGGTKVEIK |
| 725C21 | 61 | DTQMTQSPSTLSASVGDRVTITC | RASSS-VRYIA | WYQQKPGKAPKLLTY | PTSSLKS | GVPSRFSGSGSGPEFTLTISSLQPDDFATYYC | LQWSSYPWT | FGGGTKVEIK |
| 725C33 | 62 | DIQMTQSPSTLSASVGDRVTITC | RASSS-VRYIA | WYQQKPGKAPKLLTY | PTSSLKS | GVPSRFSGSGSGTEFTLTISSLQPDDFATYYC | LQCSSYPWT | FGGGTKVEIK |
| 725C42 | 63 | DIQLTQSPSTLSASVGDRVSITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |
| 725C57 | 64 | DIQMTQSPSTLSASVGDRVTITC | RASSS-VRYIA | WYQQKPGKAPKLLTY | PTSSLKS | GVPSRFSGSGSGTEFTLTISSLQPDDFATYYC | LQWSSYPWT | FGGGTKVEIK |

FIGURE 14B

ANTIBODIES, ANTIBODY DRUG CONJUGATES AND METHODS OF USE

CROSS-REFERENCE TO RELATED APPLICATION

This application claims the benefit of U.S. Provisional Application Ser. No. 62/202,396, filed Aug. 7, 2015, the disclosure of which is hereby incorporated by reference in its entirety, including all figures, tables and amino acid or nucleic acid sequences.

The Sequence Listing for this application is labeled "Seq-List-replace.txt" which was created on Dec. 27, 2017 and is 97 KB. The entire content of the sequence listing is incorporated herein by reference in its entirety.

The human anti-Müllerian hormone is a glycoprotein of 560 amino acids, a member of the TGF-β family. It is a hormone released by the Sertoli cells of the fetal testis, which causes degeneration of the Müller duct. It is expressed in the adult in the Sertoli cells and Leydig cells (testis) and the granulosa cells (ovary). The anti-Müllerian hormone plays a role in the activity of the adult ovary in regulation of folliculogenesis.

The anti-Müllerian hormone type II receptor (AMHR-II) is a peptide of 573 amino acids and has serine-threonine kinase activity. The receptor is involved in regression of the Müller duct associated with development of the human reproductive system. It atrophies in men, where it only forms the prostatic vesicle and the sessile hydatid, but it persists in women, where it gives rise to the fallopian tubes, the uterus and most of the vagina. In pathology, this receptor is re-expressed in a majority of ovarian and endometrial cancers.

BRIEF SUMMARY OF THE INVENTION

This invention relates to novel antibody drug conjugates (ADC). Particularly, the ADC disclosed herein specifically bind to the human anti-Müllerian hormone type II receptor (AMHR-II) and can be used to treat AMHR-II expressing cancers, such as prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma. In certain embodiments, the antibody portion of the ADC is an antibody or antigen binding fragment thereof that binds to AMHR-II and can be a murine monoclonal antibody, a chimeric antibody or a humanized antibody that bind to AMHR-II. In certain embodiments, the antibody that binds to AMHR-II is selected from monoclonal antibody 12G4, a chimeric 12G4 antibody or a humanized 12G4 antibody or antigen binding fragments thereof. In general this invention provides ADCs that are highly selected for AMHR-II expressing gynecologic cancers and the ADCs display both higher efficacy and higher tolerability that results in an outstanding efficacy/safety ratio.

The subject application also provides methods of providing therapeutic benefit to subjects having cancers that contain AMHR-II densities of less than about 20,000 per cell. For cancerous cells expressing these levels of AMHR-II density, it has been found, typically, that this receptor density is insufficient for providing therapeutic benefit to a subject. However, as illustrated in the examples accompanying this application, we have shown that, unexpectedly, dramatic in vivo antitumoral efficacy with a single administration of an ADC as disclosed herein which resulted in a complete shrinking of the tumor. While not wishing to be bound by theory, it is believed that the unexpectedly high antitumoral efficacy is a function of two concomitant properties: 1) AMHR-II is able to recycle at a very high rate at the cell surface from its intracellular compartment; and 2) the ADC displays very high affinity for AMHR-II with a slow K-off binding rate. The combination of these two properties supports the fact that once having bound to AMHR-II, the disclosed ADC remains bound to AMHR-II for a sufficient amount of time to induce internalization within the cell before being released from AMHR-II. This permits the subsequent release of the payload (therapeutic agent) within endosomes and expected therapeutic activity when a therapeutic agent is coupled to the antibody in the ADC.

Another aspect of the invention provides for generating high affinity antibodies against AMHR-II which provides an unexpectedly effective method for preparing ADCs effective against gynecologic cancers (such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma). Such antibodies provide for ADC having high efficacy and high tolerability as a result of the restricted tissue distribution and off-target effects. These antibodies can be conjugated to drugs via a variety of methods.

Another aspect of the invention provides ADC having improved tolerability and pharmacokinetics. As demonstrated in the Examples, ADC according to the disclosed invention have very high antitumoral efficacy (resulting in complete tumor shrinking) while no clinical side effects were observed (indicating an outstanding tolerability). Another aspect of the invention provide for ADC having reduced affinity for the CD16 receptor. In this aspect of the invention, it has been unexpectedly demonstrated that the ADC disclosed herein have a significantly reduced affinity for CD16 as compared to the unmodified antibody. For example, the ADC based upon the 3C23K antibody displays little affinity for CD16 whereas the unmodified antibody exhibits a very high affinity (in the nanomolar range) for CD16 receptor. As illustrated in the Examples, certain embodiments provide ADCs that have little or no off-target binding, especially in the liver and lymphoid tissues.

BRIEF DESCRIPTION OF THE FIGURES

The patent or application file contains at least one drawing executed in color. Copies of this patent or patent application publication, with color drawing(s), will be provided by the Office upon request and payment of the necessary fee.

FIGS. 14A-14B: Amino acid variable domain sequences of the antibodies of the invention. A) Alignment of the VH domain, B) Alignment of the VL domain. Amino acid numbering according to Kabat.

DETAILED DESCRIPTION

Definitions

Figure 1:
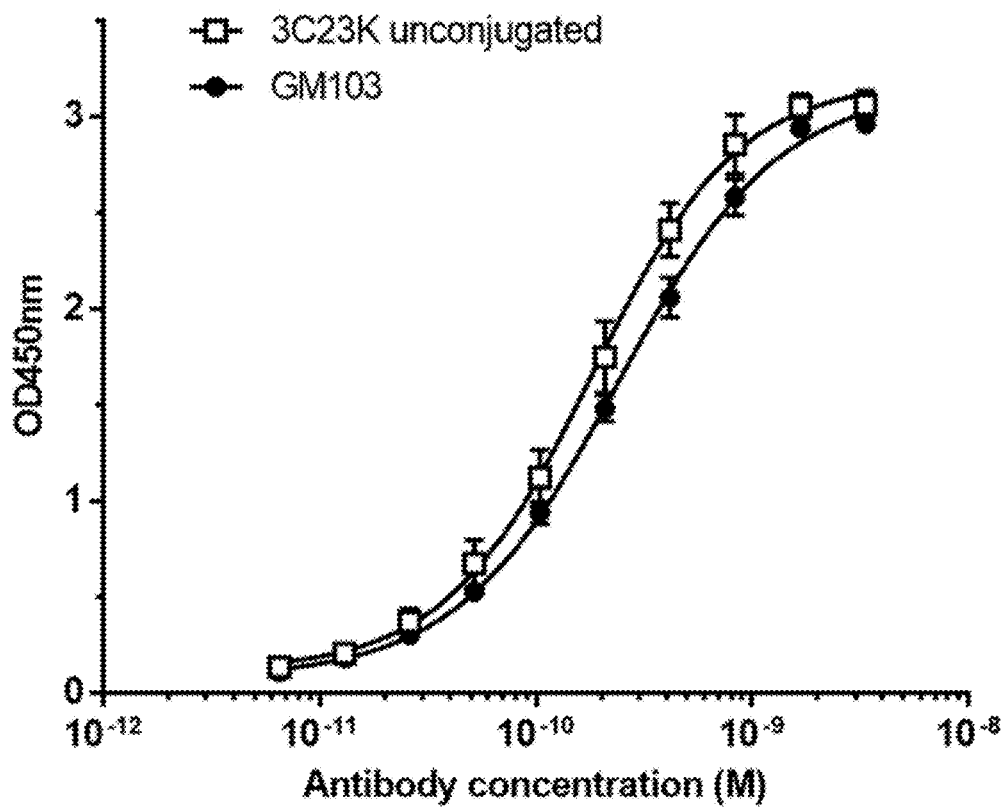
FIG. 1: Binding of anti-AMHR-II antibodies to the extracellular domain of AMHR-II receptor. Binding of unconjugated 3C23K and GM103 was determined by ELISA using HRP-labelled anti-human Fab'2 antibody.

The terms "antibody" or "immunoglobulin" (and grammatical variants thereof) have the same meaning, and can be used interchangeably within the application. Antibody refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). In the context of this invention and for the purposes of this invention, the term "antibody" or "immunoglobulin" refers to the murine 12G4 antibody or its chimeric or humanized variants.

The term "chimeric antibody" refers to an engineered antibody which comprises a VH domain and a VL domain of an antibody derived from a non-human animal, a CH domain and a CL domain of another antibody, in particular a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody". Preferred antibodies for the purposes of this invention include those disclosed in U.S. Pat. No. 9,012,607 (which is hereby incorporated by reference in its entirety and may be referred to as the "607 patent). Particularly preferred antibodies for use in the disclosed ADC are those identified as 3C23 antibodies (and variants thereof).

"Antibody fragments" comprise an antigen binding or variable region of the intact antibody. Examples of antibody fragments include Fab, F(ab')2, Fab'. For the purposes of this application, antibody fragments must contain an intrachain or interchain disulfide bond. The term "Fab" denotes an antibody fragment having a molecular weight of about 50,000 and antigen binding activity, in which about a half of the N-terminal side of heavy (H) chain and the entire light (L) chain are present and bound together through a disulfide bond.

The term "F(ab')$_2$" refers to an antibody fragment having a molecular weight of about 100,000 and antigen binding activity. This fragment is slightly larger than the Fab and contains disulfide bonds found in the hinge region of the intact antibody. "F(ab')$_2$" can give rise to Fab' fragments via the reduction of the disulfide bond connecting the two Fab'.

The term "AMHR-II" denotes the human Anti-Müllerian Hormone type II Receptor. The sequence of the human AMHR-II (lacking the signal peptide MLGSLGLWALL-PTAVEA (SEQ ID NO: 17) is:

```
                                         (SEQ ID NO: 18)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMALVLLGLFLLLLLLLGSIIL

ALLQRKNYRVRGEPVPEPRPDSGRDWSVELQELPELCFSQVIREGGHAVV

WAGQLQGKLVAIKAFPPRSVAQFQAERALYELPGLQHDHIVRFITASRGG

PGRLLSGPLLVLELHPKGSLCHYLTQYTSDWGSSLRMALSLAQGLAFLHE

ERWQNGQYKPGIAHRDLSSQNVLIREDGSCAIGDLGLALVLPGLTQPPAW

TPTQPQGPAAIMEAGTQRYMAPELLDKTLDLQDWGMALRRADIYSLALLL

WEILSRCPDLRPDSSPPPFQLAYEAELGNTPTSDELWALAVQERRRPYIP

STWRCFATDPDGLRELLEDCWDADPEARLTAECVQQRLAALAHPQESHPF

PESCPRGCPPLCPEDCTSIPAPTILPCRPQRSACHFSVQQGPCSRNPQPA

CTLSPV.
```

Several variants of the human AMHR-II are also known. The sequences for these isoforms are provided by the identifiers Q16671-2 and Q16671-3 at the web site uniprot.org.

As used herein, the term "subject" denotes a mammal, such as a rodent, a feline, a canine, or a primate. Preferably a subject according to the invention is a human.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means a range of 0-20%, 0 to 10%, 0 to 5%, or up to 1% around given value. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropiiate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. A range can also include time frames characterized by the phrase "up to", such as "up to 4 weeks". In this context, the range represents any number of weeks or days within the range up to 4 weeks or 28 days and can be rephrases as a range of "1 to 4 weeks", "2 to 4 weeks", "5 to 10 days", etc.

The present invention relates to monoclonal antibodies and fragment thereof directed against the human Anti-Müllerian Hormone type II receptor (AMHR-II). These antibodies can be coupled to a drug (and may be referred to as an antibody drug conjugate (ADC)). The present invention also provides for the use of the disclosed ADC for treating and diagnosing AMHR-II expressing cancers, such as prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma.

Antibodies:

Antibodies that specifically bind to AMHR-II may be produced by any technique known in the art. Thus, antibodies useful for the production of ADC, as described herein, can be murine monoclonal antibodies, human monoclonal antibodies, chimeric antibodies or humanized antibodies. Where chimeric and humanized antibodies are contemplated, the amino acid sequence of the desired sequence, one skilled in the art can readily produce such antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, such antibodies can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In certain embodiments, a method of producing an antibody is provided that comprises the steps consisting of: (i) culturing a transformed host cell under conditions suitable to allow expression of said antibody or polypeptide; and (ii) recovering the expressed antibody. Antibodies and polypeptides of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, a human chimeric antibody of the present invention can be produced by obtaining nucleic sequences encoding VL and VH domains of a monoclonal antibody, constructing a human chimeric antibody expression vector by inserting the nucleic sequences encoding VL and VH domains of said monoclonal antibody into an expression vector genes encoding human antibody CH and human antibody CL sequences. The CH domain of a human chimeric antibody may be any region which belongs to human immunoglobulin, but those of IgG class are suitable and any one of subclasses belonging to IgG class, such as IgG1, IgG2, IgG3 and IgG4 can also be used. For the CL portion of a human chimeric antibody, it may be a kappa class or lambda class light chain constant region. Methods for producing chimeric antibodies involve conventional recombinant DNA and gene transfection techniques are well known in the art (See Morrison S L. et al. (1984) and patent documents U.S. Pat. Nos. 5,202,238; and 5,204,244, each of which is hereby incorporated by reference in its entirety).

Humanized antibodies may be produced by obtaining nucleic acid sequences encoding CDR domains and constructing a humanized antibody according to techniques known in the art. Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

A monoclonal antibody against Mullerian Hormone type II receptor (and humanized derivatives thereof) has been developed for the treatment of ovarian cancer (see EP 2097453B1 and U.S. Pat. No. 8,278,423, which is hereby incorporated by reference in its entirety). The present invention, thus, relates to the monoclonal antibody 12G4 (mAb 12G4), or chimeric or humanized variants thereof, which has been derivatized with a drug or detectable label to form an ADC. The hybridoma producing mAb12G4 has been deposited at the Collection Nationale de Cultures de Microorganismes (CNCM, Institut Pasteur, 25 rue du Docteur Roux, 75724 Paris Cedex 15, France), in accordance with the terms of Budapest Treaty, on the 26th of Sep. 2006) and has CNCM deposit number 1-3673. The variable domain of the light and heavy chains of the mAb 12G4 have been sequenced as have been the complementarity determining regions (CDRs) of mAb 12G4 (see EP 2097453B1 and U.S. Pat. No. 8,278,423, which is hereby incorporated by reference in its entirety). mAb 12G4 and its chimeric or humanized variants can be used for the production of ADC as disclosed herein.

PCT/FR2011/050745 (International Publication No. WO/2011/141653) and U.S. Pat. No. 9,012,607, each of which is hereby incorporated by reference in its entirety, disclose novel humanized antibodies that are derived from the murine 12G4 antibody. In particular embodiments, the antibody used for the construction of the ADC disclosed herein are those identified as the 3C23 and 3C23K antibodies in these patent documents. The nucleic acid sequences and polypeptide sequences of these antibodies are provided as SEQ ID NOs: 1-16 herein. In some aspects of the invention, the antibodies may be referred to as "comprising a light chain comprising SEQ ID NO: _____ and a heavy chain comprising SEQ ID NO: _____". Thus, in various embodiments, particularly preferred antibodies for the generation of ADC comprise:

a) a light chain comprising SEQ ID NO: 2 and a heavy chain comprising SEQ ID NO: 4 (3C23 $V_L$, and $V_H$ sequences without leaders);

b) a light chain comprising SEQ ID NO: 6 and a heavy chain comprising SEQ ID NO: 8 (3C23K $V_L$, and $V_H$ sequences without leaders);

c) a light chain comprising SEQ ID NO: 10 and a heavy chain comprising SEQ ID NO: 12 (3C23 light and heavy chains without leaders);

d) a light chain comprising SEQ ID NO: 14 and a heavy chain comprising SEQ ID NO: 16 (3C23K light and heavy chains without leaders).

Other antibodies (e.g., humanized or chimeric antibodies) can be based upon the heavy and light chain sequences provided in FIGS. 14A and 14B (e.g., antibodies, such as humanized or chimeric antibodies containing the CDR sequences disclosed within the Figures) can be used for the formation of ADCs disclosed herein. Thus, the invention also pertains to antibodies comprising/containing CDRs comprising (or consisting of) the following sequences: CDRL-1: $RASX_1X_2VX_3X_4X_5A$ (SEQ ID NO: 65), where $X_1$ and $X_2$ are, independently, S or P, $X_3$ is R or W or G, $X_4$ is T or D, and $X_5$ is I or T; CDRL-2 is $PTSSLX_6S$ (SEQ ID NO: 66) where $X_6$ is K or E; and CDRL-3 is LQWSSYPWT (SEQ ID NO: 67); CDRH-1 is $KASGYX_7FTX_8X_9HIH$ (SEQ ID NO: 68) where $X_7$ is S or T, $X_8$ is S or G and $X_9$ is Y or N; CDRH-2 is $WIYPX_{10}DDSTKYSQKFQG$ (SEQ ID NO: 69) where $X_{10}$ is G or E and CDRH-3 is GDRFAY (SEQ ID NO: 70) and ADCs generated using such antibodies. Antibodies (e.g., chimeric or humanized) within the scope of this application include those disclosed in the following table: Alternatively, human monoclonal antibodies that specifically bind to AMHR-II can be used for the preparation of ADCs.

3C23K antibody is defined by:
SEQ ID NO: 19 for VH amino acid sequence
SEQ ID NO: 36 for VL amino acid sequence

| | Antibody | VH mutations | SEQ ID in sequence listing | VL mutations | SEQ ID in sequence listing |
|---|---|---|---|---|---|
| 1 | 3C23K | | 19 | | 36 |
| 2 | 3C23 | | 19 | L-K55E | 37 |
| 3 | 3C23KR | H-R3Q | 20 | | 36 |
| 4 | 6B78 | H-R3Q | 20 | L-T48I, L-P50S | 38 |
| 5 | 5B42 | H-R3Q, H-T73A | 21 | L-T48I, L-K55E | 39 |
| 6 | K4D-24 | H-Q1R | 22 | | 36 |
| 7 | 6C59 | H-Q1R | 22 | L-S27P, L-S28P | 40 |
| 8 | K4D-20 | H-Y32N | 23 | | 36 |
| 9 | K4A-12 | H-A16T | 24 | | 36 |
| 10 | K5D-05 | H-S31G | 25 | | 36 |
| 11 | K5D-14 | H-T28S | 26 | | 36 |
| 12 | K4D-123 | H-R44S | 27 | | 36 |
| 13 | K4D-127 | H-I69T | 28 | | 36 |
| 14 | 6C07 | H-I69T | 28 | L-M4L, L-T20A | 41 |
| 15 | 5C14 | H-I69F | 29 | | 36 |
| 16 | 5C26 | H-V67M | 30 | L-S27P | 42 |
| 17 | 5C27 | H-L45P | 31 | | 36 |
| 18 | 5C60 | H-E10K, H-K12R | 32 | | 36 |
| 19 | 6C13 | H-G53E | 33 | | 36 |
| 20 | 6C18 | H-T93A | 34 | | 36 |
| 21 | 6C54 | H-S84P | 35 | L-M4L, L-S9P, L-R31W | 43 |
| 22 | K4D-25 | | 19 | L-M4L | 44 |
| 23 | K4A-03 | | 19 | L-I33T | 45 |
| 24 | K4A-08 | | 19 | L-M4L, L-K39E | 46 |

-continued

3C23K antibody is defined by:
SEQ ID NO: 19 for VH amino acid sequence
SEQ ID NO: 36 for VL amino acid sequence Mutations

| | Antibody | VH mutations | SEQ ID in sequence listing | VL mutations | SEQ ID in sequence listing |
|---|---|---|---|---|---|
| 25 | K5D-26 | | 19 | L-T22P | 47 |
| 26 | 5C08 | | 19 | L-Y32D | 48 |
| 27 | 5C10 | | 19 | L-S27P | 42 |
| 28 | 5C18 | | 19 | L-Q37H | 49 |
| 29 | 5C42 | | 19 | L-G97S | 50 |
| 30 | 5C44 | | 19 | L-S12P | 51 |
| 31 | 5C52 | | 19 | L-19A | 52 |
| 32 | 5C56 | | 19 | L-T72A | 53 |
| 33 | 6C03 | | 19 | L-R31W | 54 |
| 34 | 6C05 | | 19 | L-M4L, L-M39K | 55 |
| 35 | 6C16 | | 19 | L-I2N | 56 |
| 36 | 6C17 | | 19 | L-G63C, L-W91C | 57 |
| 37 | 6C28 | | 19 | L-R31G | 58 |
| 38 | 725C02 | | 19 | L-I75F | 59 |
| 39 | 725C17 | | 19 | L-I2T | 60 |
| 40 | 725C21 | | 19 | L-I2T, L-K42R | 61 |
| 41 | 725C33 | | 19 | L-Y49H | 62 |
| 42 | 725C42 | | 19 | L-M4L, L-T20S, L-K39E | 63 |
| 43 | 725C44 | | 19 | L-S27P | 42 |
| 44 | 725C57 | | 19 | L-T69P | 64 |

Amino acid substitutions numbering according to Kabat.

Also contemplated within the scope of the present application are other monoclonal, chimeric or humanized antibodies that have high affinity for AMHR-II. In the context of the present invention, the antibodies have a dissociation constant (hereinafter, referred to as "$K_D$") that is $1 \times 10^{-5}$ or lower, $5 \times 10^{-6}$ or lower, $2 \times 10^{-6}$ or lower, or $1 \times 10^{-6}$ or lower, more preferably $5 \times 10^{-7}$ or lower, $2 \times 10^{-7}$ or lower, or $1 \times 10^{-7}$ or lower, even more preferably $5 \times 10^{-8}$ or lower, $2 \times 10^{-8}$ or lower, or $1 \times 10^{-8}$ or lower, further more preferably $5 \times 10^{-9}$ or lower, $2 \times 10^{-9}$ or lower, or $1 \times 10^{-9}$ or lower, most preferably $5 \times 10^{-10}$ or lower, $2 \times 10^{-10}$ or lower, or $1 \times 10^{-10}$ or lower for AMHR-II. More specifically, the preferable antibody of the present invention has a $K_D$ value of $2 \times 10^{-8}$ or lower, more preferably $1 \times 10^{-8}$ or lower, even more preferably $5 \times 10^{-9}$ or lower for AMHR-II.

Other embodiments contemplate humanized antibodies that have a binding affinity for AMHR-II that is increased relative to the original murine antibody or a chimeric antibody derived therefrom. In various embodiments the increase in affinity ($K_D$) can be defined a factor determined by dividing the $K_D$ of the murine monoclonal antibody or a chimeric antibody derived therefrom by the $K_D$ of the humanized antibody. Thus, the increase in affinity can be a factor of at least 1.5 up to a factor of 15 or range from 1.5 to 15.0. In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Accordingly, the range of 1.5 to 15.0 represents the terminal values of 1.5 and 15.0, as well as all intermediate ranges encompassed within 1.5 to 15.0 and each intermediate value between 1.5 and 15.0.

An ADC according to the instant application may be labelled with a radioisotope by any method known to the art for use in imaging or therapy. For example imaging radioisotopes, include but are not limited to, $I^{123}$, $I^{124}$, $In^{111}$, $Re^{186}$, $Re^{188}$. ADC may be also labelled with a spin label for nuclear magnetic resonance (NMR) imaging (also known as magnetic resonance imaging, MM). Spin labels for such a use include iodine-123, iodine-131, indium-III, fluorine-19, carbon-13, nitrogen-15, oxygen-17, gadolinium, manganese or iron.

Therapeutic Methods and Diagnostic Methods

The ADC disclosed herein may be used for treating any cancer disease associated with the expression of human AMHR-II. Non-limiting examples of such cancers include prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma. The ADC of the invention may be used alone or in combination with any suitable agent. It is well known that therapeutic monoclonal antibodies can lead to the depletion of cells bearing the antigen specifically recognized by the antibody. This depletion can be mediated through at least three mechanisms: antibody mediated cellular cytotoxicity (ADCC), complement dependent lysis, and direct anti-tumor inhibition of tumor growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed. It is known that mAb 12G4 and its humanized and chimeric variants mediate ADCC and bind strongly to CD16a when these antibodies are produced in YB2/0 cell line. However, it has been, unexpectedly, found that the ADC of this application have significantly reduced binding to CD16a as compared to the unmodified variants of the 12G4 antibody.

Another object of this application relates to a method for treating a cancer associated with the expression of AMHR-II comprising administering a subject in need thereof with a therapeutically effective amount of an ADC as provided herein. In the context of the invention, the term "treating" or "treatment", as used herein, means reversing, alleviating, or slowing the progression of a cancer associated with AMHR-II expression. Particularly, the ADC disclosed herein are useful for the treatment of AMHR-II expressing cancers, such as prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma. As used herein, the terms "patient" or "patient in need thereof" or "subject" or "subject in need thereof" is intended for a human or non-human mammal affected cancer disease with the expression of AMHR-II.

A "therapeutically effective amount" of an ADC an amount of the ADC sufficient to treat said cancers associated with the expression of AMHR-II. It will be understood, however, that the total daily usage of the ADC and compositions thereof will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well known in the medical arts. ADC may be used in combination with any other therapeutic strategy for treating AMHR-II expressing cancers, such as prostate cancer, breast cancer and gynecologic cancers expressing AMHR-II, such as ovarian cancer, in particular metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma (e.g. external radiotherapy, chemotherapy or cytokines) or administration of a "naked" antibody that specifically binds to AMHR-II (such as the 3C23K antibody). In this aspect of the invention, a "naked antibody" is an antibody that is not coupled to a therapeutic or diagnostic agent (i.e., the antibody is not coupled to maytansine and derivatives thereof, radioactive isotopes, chemotherapeutic agents or toxins [also referred to as an "unmodified antibody"]). The naked antibody can be the unconjugated form of any antibody used to generate the ADC disclosed herein or can be a different antibody that specifically binds AMHR-II (provided that the antibody is not conjugated/coupled to a therapeutic or diagnostic agent (i.e., is unmodified).

Various dosing regimens are also contemplated by the disclosed invention. For example, dosing regimens comprising the administration of ADCs disclosed herein include: a) a single weekly ADC dose administered for a period of up to 2 or 3 months; or b) once-weekly ADC doses for up to 4 weeks every 6 months for a period of up to 2 years; or c) consecutive daily ADC doses for a period of up to 4 weeks; or d) two to seven ADC doses, administered once per day, for a period of about two weeks. Following any of these ADC dosing schedules, additional therapeutic agents (external radiotherapy, chemotherapy or cytokines or administration of a "naked" antibody that specifically binds to AMHR-II (such as the 3C23K antibody)) can be administered to the subject. Where a naked antibody is used for subsequent treatment, the naked antibody can be administered: a) as a single dose every two to three months; or b) once weekly for a period of up to four weeks every six months with a duration of the once weekly administration that is between 1 and 4 years (e.g., up to 1 year, up to two years, up to three years or up to four years); or c) once weekly for a period of up to six months; or d) once per month for a period of up to 12 months; or e) biweekly for a period of up to 52 weeks.

In another aspect, the invention is a method of diagnosing a cancer disease associated with AMHR-II expression in a subject by detecting AMHR-II on cells within the subject using the antibody of the invention. In particular, said method of diagnosing may comprise the steps consisting of: (a) administering a labeled ADC according to the subject application to a subject likely to suffer from a cancer disease associated with AMHR-II expression; and (b) detecting and/or quantifying the binding of said ADC to cancerous tissue or cells expressing AMHR-II expression, whereby the detection of said complexes is indicative of a cancer disease associated with AMHR-II expression. In various embodiments, a subject is imaged with a device or detector capable of detecting radionuclide emissions such as a gamma scintillation counter. Where paramagnetic labelling is used, a NMR (Nuclear Magnetic Resonance) spectrometer may be used.

Pharmaceutical Compositions

The ADC disclosed herein may be combined with pharmaceutically acceptable excipients, and optionally sustained-release matrices, such as biodegradable polymers, to form therapeutic compositions. The terms "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. To prepare pharmaceutical compositions, an effective amount of the antibody may be dissolved or dispersed in a pharmaceutically acceptable carrier or aqueous medium.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

An ADC can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid; thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In certain embodiments, the use of liposomes and/or nanoparticles is contemplated for the introduction of antibodies into host cells. The formation and use of liposomes and/or nanoparticles are known to those of skill in the art.

Diagnostic Methods and Uses

A further object of the disclosed invention relates to the use of an antibody of the invention for diagnosing and/or monitoring a cancer disease associated with AMHR-II expression. Cancers associated with AMHR-II expression typically include ovarian cancers. In a preferred embodiment, antibodies of the invention are useful for diagnosing prostate cancer, breast cancer and gynecologic cancers expressing AMHR-II. Non-limiting examples of gynecologic cancers expressing AMHR-II include ovarian cancer, metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma.

In a preferred embodiment, antibodies of the invention may be labelled with a detectable molecule or substance, such as a fluorescent molecule, a radioactive molecule, an enzyme or any others labels known in the art. Labels are known in the art that generally provide (either directly or indirectly) a signal. As used herein, the term "labeled", with regard to the antibody, is intended to encompass direct labeling of the antibody by coupling (i.e., physically linking or coupling) a detectable substance, such as a radioactive agent or a fluorophore (e.g. fluorescein isothiocyanate (FITC) or phycoerythrin (PE) or indocyanine (Cy5)) or an enzyme, such as alkaline phosphatase, to the antibody, as well as indirect labeling of the antibody by reactivity with a detectable substance. For example, an antibody of the invention may be labelled with a radioactive molecule by any method known to the art. For example radioactive molecules include but are not limited radioactive atom for scintigraphic studies such as $I^{123}$, $I^{124}$, $In^{111}$, $Re^{186}$ and $Re^{188}$. Antibodies of the invention may be also labelled with a spin label for nuclear magnetic resonance (NMR) imaging (also known as magnetic resonance imaging, MRI). Such spin labels include, and are not limited to, iodine-123, iodine-131, indium-III, fluorine-19, carbon-13, nitrogen-15, oxygen-17, gadolinium, manganese or iron.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen (e.g., prostate tissue, ovaries, vaginal endometrium, uterus, kidney, or any other tissue associated with a cancer discussed in the preceding paragraphs) or tissue cultures or cells derived therefrom, and the progeny thereof. For example, biological samples include cells obtained from a tissue sample collected from an individual suspected of having a cancer associated with AMHR-II expression, and in a preferred embodiment from ovary. Therefore, biological samples encompass clinical samples, cells in culture, cell supernatants, cell lysates, serum, plasma, biological fluid, and tissue samples.

The term "detection" as used herein includes qualitative and/or quantitative detection (measuring levels) with or without reference to a control.

In another aspect, the invention is a method of diagnosing a cancer disease associated with AMHR-II expression in a subject by detecting AMHR-II on cells from the subject using the antibody of the invention. In particular, said method of diagnosing may comprise:

(a) contacting a biological sample of a subject likely to suffer from a cancer disease associated with AMHR-II expression with an antibody according to the invention in conditions sufficient for the antibody to form complexes with cells of the biological sample that express AMHR-II;

(b) detecting and/or quantifying said complexes, whereby the detection of said complexes is indicative of a cancer disease associated with AMHR-II expression. In order to monitor the cancer disease, the method of diagnosing according to the invention may be repeated at different intervals of time, in order to determine if antibody binding to the samples increases or decreases, whereby it is determined if the cancer disease progresses or regresses.

Antibody Drug Conjugates (ADC)

As discussed above, the disclosed invention relates to antibody drug conjugates comprising an antibody as disclosed herein conjugated to an agent, such as a cytotoxic agent or a growth inhibitory agent. Any antibody that specifically binds to AMHR-II can be used for the formation of an ADC or used as a "naked antibody" as described herein.

Conjugation of the antibodies of the invention with therapeutic or diagnostic agents (e.g., cytotoxic agents or growth inhibitory agents) may be made using a variety of bifunctional protein coupling agents including but not limited to N-succinimidyl (2-pyridyldithio)propionate (SPDP), succinimidyl(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026). In various embodiments, the coupling agent may be a "cleavable linker" facilitating release of the cytotoxic agent or growth inhibitory agent in the cell. For example, an acid-labile linker, peptidase-sensitive linker, photolabile linker, dimethyl linker or disulfide-containing linker (see, for example, U.S. Pat. No. 5,208,020 which is hereby incorporated by reference in its entirety) may be used.

Antibody conjugates of cytotoxic drugs have been, and are, being developed as target-specific therapeutic agents. For example, cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; 7,276,497, each of which is hereby incorporated by reference), DNA (calicheamicin, doxorubicin, CC-1065 analogs; U.S. Pat. Nos. 5,475,092; 5,585,499; 5,846,545; 6,534,660; 6,756,397; 6,630,579, each of which is hereby incorporated by reference) have been conjugated to antibody molecules and are under current clinical investigation. Such antibody-cytotoxic agent conjugates typically are prepared by the initial modification of reactive moieties on antibodies, such as lysine amino groups. Thus, antibodies can be first modified with a heterobifunctional linker reagent, such as those previously exemplified by SPDB, SMCC and STAB (U.S. Patent Publication No. 2005/0169933) to incorporate a linker with a reactive group such as mixed pyridyldisulfide, maleimide or haloacetamide. The incorporated reactive linker group in the antibody is subsequently conjugated with a cytotoxic agent containing a reactive moiety such as a thiol group. Another conjugation route is by reaction of a cytotoxic agent derivative containing a thiol-reactive group (such as haloacetamide, or maleimide) with thiol groups on the antibody.

U.S. Pat. No. 9,150,649, which is hereby incorporated by reference in its entirety (particularly with respect to the maytansinoid conjugates disclosed therein), describes linkers used to conjugate therapeutic agents or diagnostic agents to antibodies. These linkers incorporate polyethylene glycol spacers and increase the potency and/or efficacy of antibodies conjugated to therapeutic agents, such as maytansinoids. Thus, one embodiment of the disclosed invention provides for antibody conjugates comprising the maytansinoid compounds disclosed in U.S. Pat. No. 9,150,649 conjugated to the disclosed antibodies via the primary amine group (free amino groups) on lysine residues found in the antibodies disclosed herein. Other embodiments provide for the conjugation of therapeutic agents, such as maytansinoids, via the linkers disclosed in U.S. Pat. No. 8,236,319, which is hereby incorporated by reference in its entirety. Such linkers can be used to conjugate therapeutic or diagnostic agents to antibodies via a disulfide, thioether, thioester, peptide, hydrazone, ester, ether, carbamate or amide bond. In preferred embodiments, the linkers of U.S. Pat. No. 8,236,319 conjugate therapeutic agents via the free amino group of lysine residues within the antibody. Where the CDRs of an antibody contain a lysine residue, the lysine residue can be substituted with another amino acid, such as asparagine or glutamine, to eliminate the possibility of the conjugate affecting binding affinity due to its attachment to the free amino group of the lysine residue.

In certain embodiments, the drug conjugate portion of the disclosed ADC are of the formula $(((D_q\text{-}Lk^1)_m\text{-}P)_p\text{-}Lk^2\text{-}Lk^3)_n\text{-}$ which is disclosed in U.S. Patent Application Publication US 2015/0125473 which is hereby incorporated by reference in its entirety and much of which is provided in the following sections.

A preferred aspect of the invention provides an ADC which has the general formula:

$(((D_q\text{-}Lk^1)_m\text{-}P)_p\text{-}Lk^2\text{-}Lk^3)_n\text{-}Ab$ (I)

in which D represents a therapeutic or diagnostic agent;
q represents an integer from 1 to 10;
$Lk^1$ represents a linker;
m represents an integer from 1 to 10;
P represents a bond or a z-valent group —$P^1$—NH— where z is from 2 to 11 and $P^1$ is a group containing at least one ethylene unit —$CH_2$—$CH_2$— or ethylene glycol unit —O—$CH_2$—$CH_2$—;
p represents an integer from 1 to 10;
$Lk^2$ represents a bond or a y-valent linker where y is from 2 to 11 and which consists of from 1 to 9 aspartate and/or glutamate residues;
$Lk^3$ represents a linker of the general formula:

—CO-Ph-X—Y— (II)

in which Ph is an optionally substituted phenyl group; X represents a CO group or a CH.OH group; and Y represents a group of formula:

(III)

(IV)

in which each of A and B represents a $C_{1-4}$alkylene or alkenylene group;

Ab represents an any antibody or antigen binding fragment thereof that specifically binds to AMHR-II. In certain embodiments, the antibody or antigen binding fragment thereof can be selected from monoclonal antibody 12G4, a chimeric 12G4 antibody or a humanized 12G4 antibody or antigen binding fragments thereof. The antibody or antigen binding fragment thereof used in the formation of the ADC can be bonded to $Lk^3$ via two sulfur atoms derived from an interchain disulfide bond in the antibody or antigen binding fragment thereof; and n represents an integer from 1 to s where s is the number of disulfide bonds present in the antibody or antigen binding fragment prior to conjugation to $Lk^3$;

the meanings of m, n, p, q, y and z being chosen such that the conjugate contains from 1 to 10 D groups.

As indicated above, the D represents a therapeutic or diagnostic agent. Thus, D can be therapeutic agent is selected from maytansine and derivatives thereof, radioactive isotopes, chemotherapeutic agents and toxins. Thus, D can be a therapeutic agent is selected from chelated $At^{211}$, chelated $I^{131}$, chelated $I^{125}$, chelated $Y^{90}$, chelated $Re^{186}$, chelated $Re^{188}$, chelated $Sm^{153}$, chelated $Bi^{212}$, chelated $I^{332}$, methotrexate, adriamycin, vinca alkaloids, vincristine, vinblastine, etoposide, doxorubicin, melphalan, mitomycin C, chlorambucil, daunorubicin, enzymes, antibiotics, gelonin, ricin and saporin.

When D represents a maytansine moiety (i.e. the $Lk^1$ group is bonded to the residue of a maytansine), this moiety can be maytansine itself or maytansinoids such as 15-methoxyansamitocin P-3, and derivatives thereof (such as those disclosed in U.S. Patent Application Publication US 2015/0125473, which is hereby incorporated by reference in its entirety). For example, the maytansine attached to the disclosed antibody can comprise:

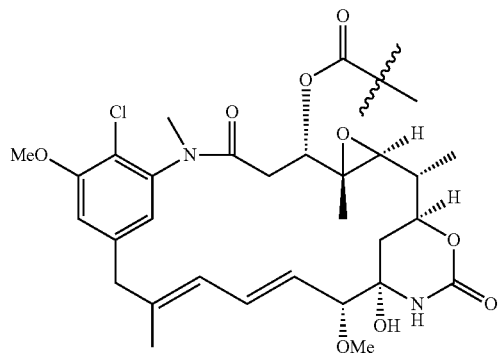

Examples of some maytansines include:

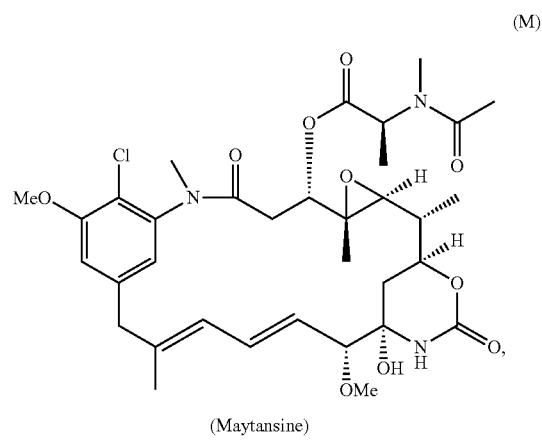

(Maytansine)

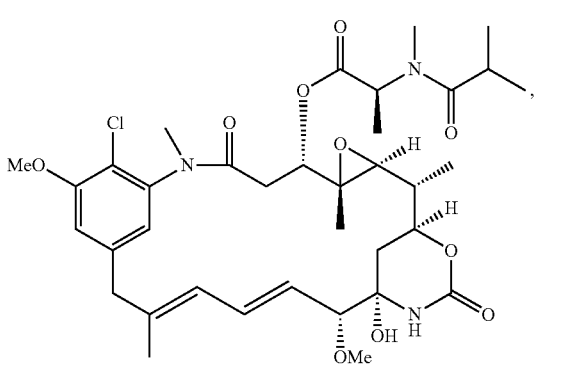

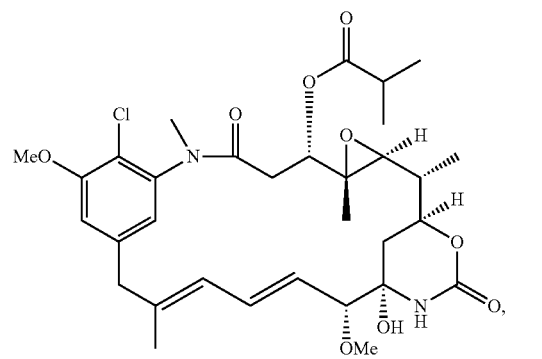

(Ansamitocin P-3)

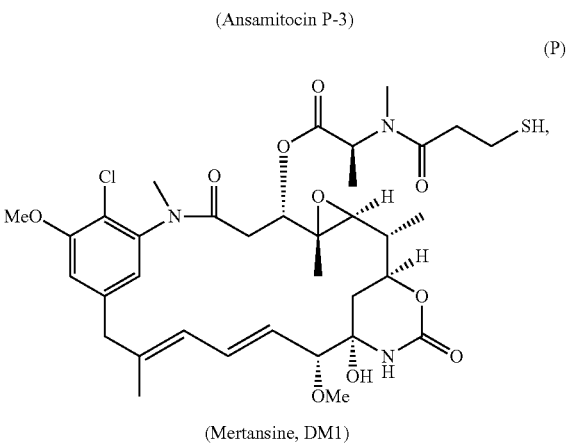

(Mertansine, DM1)

-continued

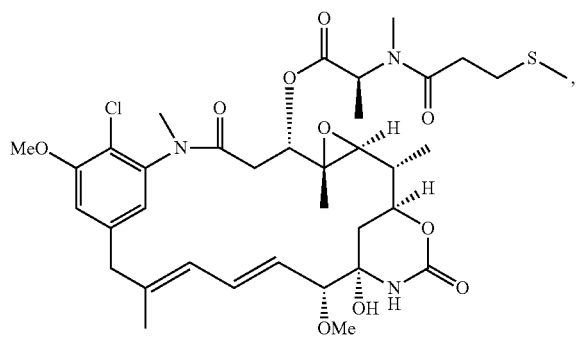

(S-methyl DM1)

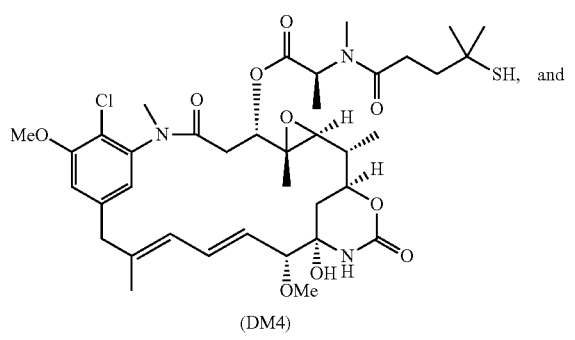

(DM4)

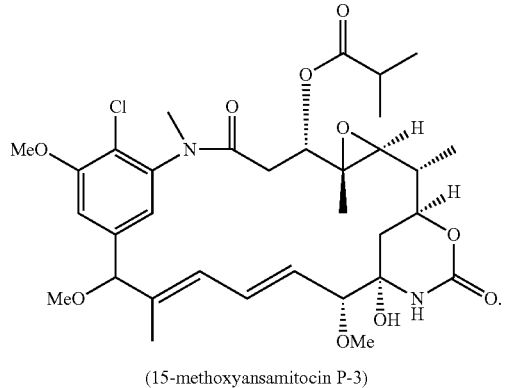

(15-methoxyansamitocin P-3)

Where the therapeutic agents is amaytansine, Lk$^1$ may be bonded at any suitable point. Lk$^1$ may for example be bonded to the nitrogen atom, e.g.:

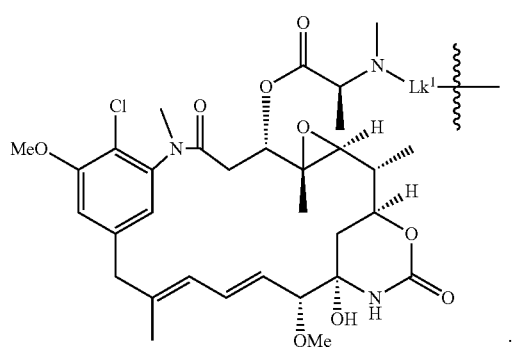

Lk$^1$ is a linker, a bond or a group which connects a maytansine moiety D to a P group and can carry from 1 to 10 D groups. Lk$^1$ preferably contains a degradable group, i.e. Lk$^1$ is preferably a linker which is cleavable under physiological conditions, separating D from the antibody of the disclosed ADC. Alternatively, Lk$^1$ may be a linker that is not cleavable under physiological conditions. When Lk$^1$ is a linker which is cleavable under physiological conditions, it is preferably cleavable under intracellular conditions.

In some embodiments, Lk$^1$ is a degradable linker that contains a group that is sensitive to hydrolysis and, thus, Lk$^1$ may contain a group which degrades at certain pH values (e.g. acidic conditions such as those found, for example, in endosomes or lysosomes). Examples of groups include hydrazones, semicarbazones, thiosemicarboazones, cis-aconitic amides, orthoesters and ketals.

Non-limiting examples of groups susceptible to hydrolytic conditions include:

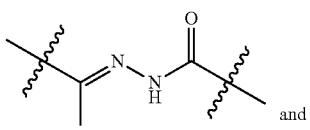 and

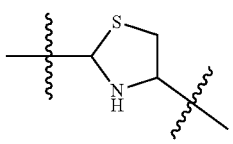

In one embodiment, Lk$^1$ is or includes

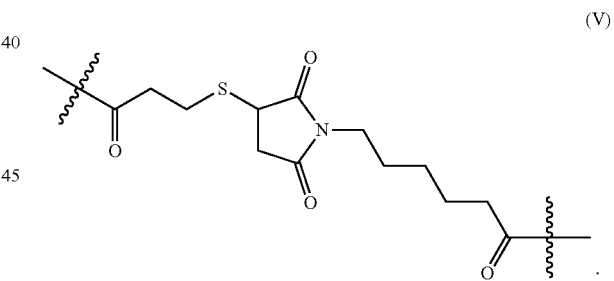

(V)

For example, Lk$^1$ may be:

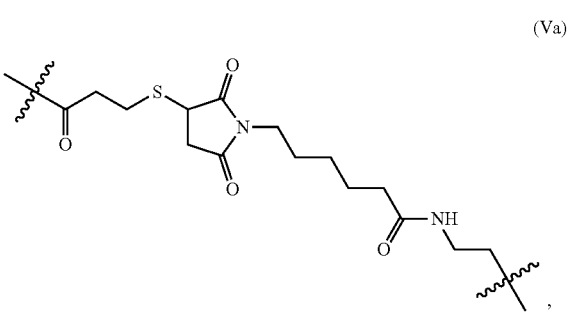 [SMILES: *CCNC(=O)CCCCCN1C(=O)CC(SCCC(*)=O)C1=O]

(Va)

in which case it is bonded to D and P groups as shown:

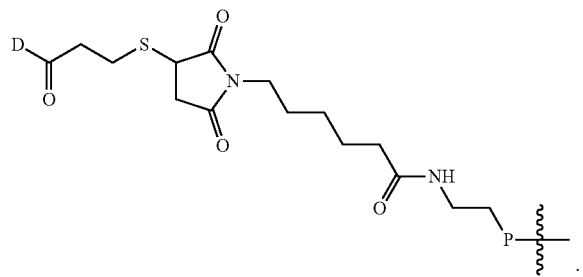

Lk¹ may also be susceptible to degradation under reducing conditions. For example, Lk¹ may contain a disulfide group that is cleavable on exposure to biological reducing agents, such as thiols. Examples of disulfide groups include:

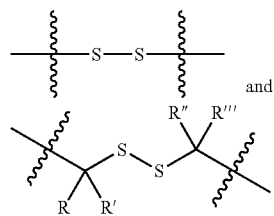

in which R, R', R" and R'" are each independently hydrogen or $C_{1-4}$alkyl. In a preferred embodiment Lk¹ is or includes

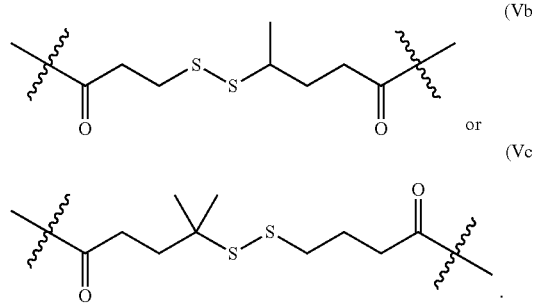

(Vb)

or (Vc)

For example, Lk¹ can be

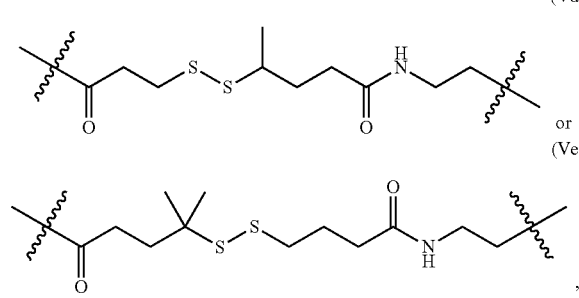

(Vd)

or (Ve)

in which case Lk¹ is preferably bonded to D and P groups as shown:

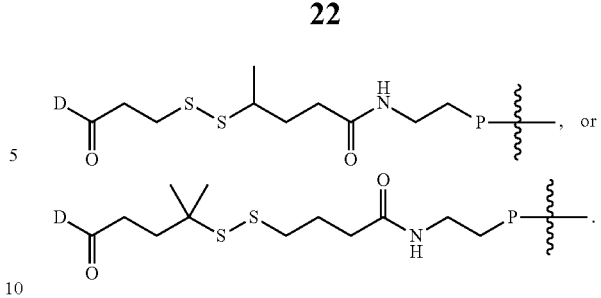

, or

Lk¹ may also contain a group which is susceptible to enzymatic degradation, for example it may be susceptible to cleavage by a protease (e.g. a lysosomal or endosomal protease) or peptidase. For example, Lk¹ may contain a peptidyl group comprising at least one, for example at least two, or at least three amino acid residues (e.g., Phe-Leu, Gly-Phe-Leu-Gly, Val-Cit, Phe-Lys). For example, Lk¹ may be an amino acid chain having from 1 to 5, for example 2 to 4, amino acids. Another example of a group susceptible to enzymatic degradation is:

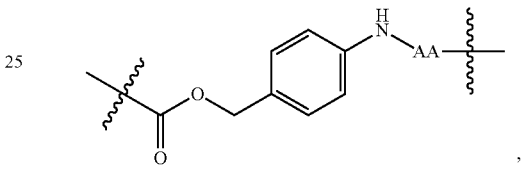

where AA represents a protease-specific amino acid sequence, such as Val-Cit.

In a preferred embodiment, Lk¹ is or includes:

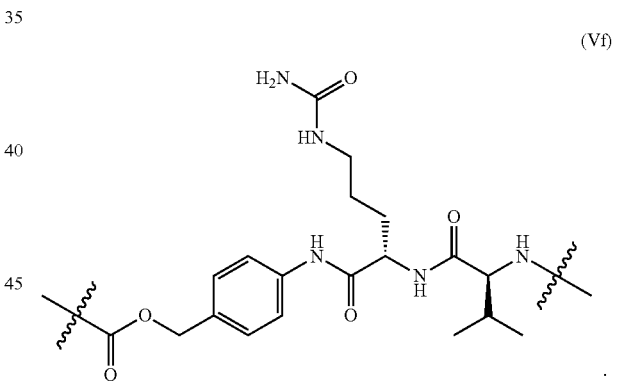

(Vf)

For example, Lk¹ may be

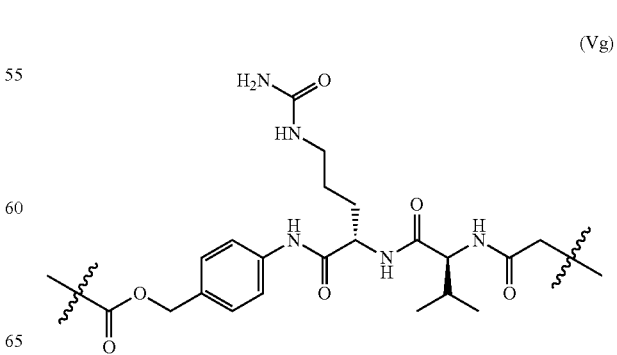

(Vg)

in which case it is preferably bonded to the D and P groups as shown below:

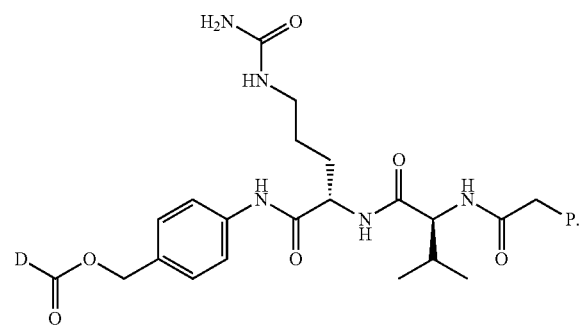

Where multiple therapeutic agents are to be incorporated into the ADC disclosed herein, a branching linker $Lk^1$, which may for example incorporate an aspartate or glutamate or similar residue can be utilized. This introduces a branching element of formula:

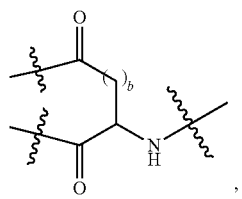

(VI)

where b is 1, 2 or 3, b=1 being aspartate and b=2 being glutamate, and b=3 representing one preferred embodiment. Each of the acyl moieties in the formula VI may be coupled to a group D via a suitable linker $Lk^{1a}$, where $Lk^{1a}$ is any suitable linker, for example a degradable linker incorporating one of the linkages mentioned above for $Lk^1$. In particular embodiments, $Lk^{1a}$ represents the group (Va), (Vd) or (Ve) shown above. The amino group of the aspartate or glutamate or similar residue may be bonded to P by any suitable means, for example the linkage may be via an amide bond, e.g. the branching group above may be connected to P via a —COCH$_2$— group, thus:

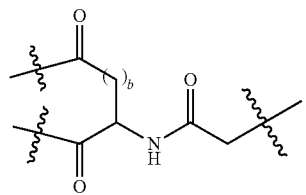

(VIa)

If desired, the aspartate or glutamate or similar residue may be coupled to further aspartate and/or glutamate and/or similar residues, for example:

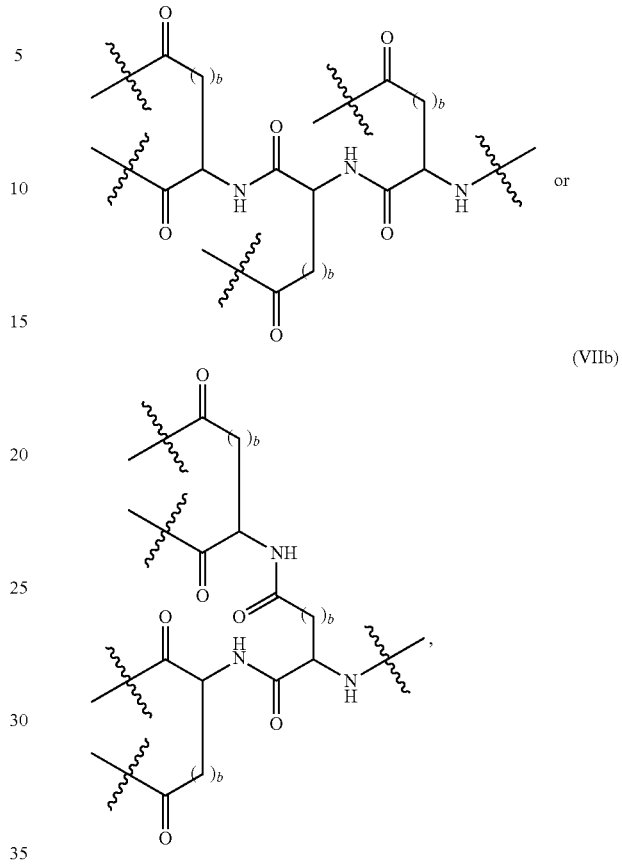

up to a maximum of 9 such residues, giving the potential to incorporate up to 10 D groups. As above, each D may be attached to an aspartate/glutamate or similar residue via any suitable linker $Lk^{1a}$.

Depending on the structure of the conjugate of formula (I), it may exist in the form of a free base or free acid, in the form of a pharmaceutically acceptable salt, and/or as a solvate.

Where P represents a —$P^1$—NH— group, $P^1$ contains at least one ethylene or ethylene glycol unit (—CH$_2$—CH$_2$— or —O—CH$_2$—CH$_2$—). If many such units are present, $P^1$ represents polyethylene, PE, or polyethylene glycol, PEG. These polymers may contain a single linear chain, or may have branched morphology composed of many chains either small or large, in which case they will contain branching groups, typically containing >CH—, as for example in —(CH$_2$CH$_2$)$_2$—CH— or —(O—CH$_2$—)$_2$CH—. They may optionally be derivatized or functionalized in any desired way. They may for example carry an additional therapeutic agent, or a labelling agent.

Where $P^1$ represents PE or PEG, the optimum molecular weight of the polymer will of course depend upon the intended application. Generally, where $P^1$ represents PE, it is preferred that the number average molecular weight is up to 2 kDa, preferably up to 1 kDa. Where $P^1$ represents PEG, higher molecular weights may be used, for example the number average molecular weight may be up to 75 kDa, for example up to 60 kDa, with the minimum number average molecular weight being for example at least 0.5 kDa, for example at least 1 kDa, for example 2 kDa. In one preferred embodiment, PEG of number average molecular weight of from 0.5 to 2 kDa may be used. However, in some preferred embodiments, P may be a bond, or P may represent —$P^1$—NH— wherein $P^1$ contains a small number of discrete ethylene or ethylene glycol units, for example from 2 to 10, for example 2 or 3, ethylene or, preferably, ethylene glycol units.

If it is desired for the conjugate of formula I to contain more than one —($CH_2$—$CH_2$)$_a$— or —(O—$CH_2$—$CH_2$)$_a$— chain (where a is the number of ethylene or ethylene glycol units in any linear chain), for example so that each such chain may carry a $D_q$-$Lk^1$ group, this may be achieved either by bonding more than one (i.e. from 2 to 10) such chains to $Lk^2$, or by using a branched PE or PEG, in which case only one group P will be attached to $Lk^2$, but this will contain more than one branch, for example from 1 to 9 branches (providing from 2 to 10 attachment points for D-$Lk^1$ groups).

It will be understood that where P is —$P^1$—NH—, the or each P group is coupled to adjacent groups $Lk^1$ and/or $Lk^2$ via an amide bond. For example PEG (which normally terminates with an —OH group) may be converted into the corresponding PEG amine, which terminates with an —$NH_2$ group, for amide bond formation with a —$CO_2$ group in, say, $Lk^2$; or the OH group may be reacted to form a linkage —NHCOCH$_2$O— with $Lk^1$ as described above. In a preferred embodiment, $P^1$ represents PEG, a water-soluble, synthetic polymer, and throughout this specification, except where the context requires otherwise, any general reference to $P^1$ should be understood to include a specific reference to PEG.

$Lk^2$ represents a y-valent linker where y is from 2 to 11. It is thus capable of bonding from 1 to 10 groups P or $Lk^1$. In its simplest form, $Lk^2$ is a bond, in which case $Lk^1$ is bonded directly to a —$P^1$—NH— group or, if P is a bond, to a D-$Lk^1$ group. However, $Lk^2$ may be used as a means of incorporating more than one D group into the conjugates of the invention. This is achieved by coupling an aspartate or glutamate residue to the —CO— group of $Lk^3$ via an amide linkage (e.g. reacting the aspartate or glutamate amine group with a suitable carboxylic acid derivative corresponding to $Lk^3$). This introduces a branching element of formula VI shown above. In that case, each of the acyl moieties may be coupled to a —$P^1$—NH— group via an amide linkage, or when P is a bond, to a D-$Lk^1$ group.

Alternatively, the aspartate or glutamate residue may be coupled to further aspartate and/or glutamate residues, as shown in formulae VIIa and VIIb shown above, and so on, up to a maximum of 9 such residues, giving the potential to incorporate up to 10 D groups via bonding of multiple D-$Lk^1$-P groups at different attachment points in $Lk^2$. It will be understood that the valency of $Lk^2$ is associated with the number of D-$Lk^1$-P groups present.

For example, when P is —$P^1$—NH—, for each D-$Lk^1$-P group, the valency of $Lk^2$ is associated with the number of —$P^1$—NH— groups present, i.e. p will equal y-1. When P is a bond, for each D-$Lk^1$-P group, the valency of $Lk^2$ is associated with the number of groups D-$Lk^1$ present, i.e. m will equal y-1.

$Lk^3$ is a specific linker capable of binding to the disclosed antibody via two sulfur groups derived from a disulfide bond in the antibody or antibody fragment. In $Lk^3$, the phenyl group Ph may be unsubstituted or substituted. Substituents which may optionally be present on the phenyl group Ph include for example one or more of the same or different substituents selected from alkyl (preferably $C_{1-4}$alkyl, especially methyl, optionally substituted by OH or $CO_2H$), —CN, —$NO_2$, —$CO_2R^4$, —COH, —$CH_2OH$, —$COR^4$, —$OR^4$, —$OCOR^4$, —$OCO_2R^4$, —$SR^4$, —$SOR^4$, —$SO_2R^4$, —$NHCOR^4$, —$NR^4COR^4$, $NHCO_2R^4$, —$NR^4.CO_2R^4$, —NO, —NHOH, —$NR^4.OH$, —C=N—$NHCOR^4$, —C=N—$NR^4.COR^4$, —$N^+R^4_3$, —$N^+H_3$, —$N^+HR^4_2$, —$N^+H_2R^4$, halogen, for example fluorine or chlorine, —C≡$CR^4$, —C=$CR^4_2$ and —C=$CHR^4$, in which each $R^4$ independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example —CN, —$NO_2$, —$OR^4$, —$OCOR^4$, —$SR^4$, —$NHCOR^4$, —$NR.COR^4$, —NHOH and —$NR^4.COR^4$. Preferably, however, the phenyl group Ph is unsubstituted.

When Y represents the group III, a single carbon bridge is formed between the linker $Lk^3$ and two sulfur atoms derived from a disulfide bond in the Ab, and when Y represents the group IV, the nature of the groups A and B determine the length of the bridge which is formed between the linker $Lk^3$ and two sulfur atoms derived from a disulfide bond in the Ab. Preferably, a 3-carbon bridge is formed, i.e. preferably Y has the formula:

(IVa)

As mentioned above, ADC which contain more than therapeutic agent moiety may have advantages. The presence of more than one therapeutic agent may be achieved in a number of different ways, for example as described above by the use of a branched PEG, by the use of a multivalent linking group $Lk^2$, or by the use of a multivalent group $Lk^1$. It may however also be achieved by attaching more than one linker $Lk^3$ to the Ab. In general, normal full-length antibodies have 4 interchain disulfide bonds (heavy-heavy chain or heavy-light chain for whole IgG1 antibodies), and any or all of these can be bridged by the linker $Lk^3$ according to the invention. It is also envisaged that one or more intrachain disulfide bonds in the antibody may be bridged by a linker $Lk^3$. Where more than one conjugating group is present, n is greater than 1 (for example 2, 3, or 4).

Alternatively or in addition, one or more additional therapeutic agent can be present linked via a linker $Lk^1$ to P or, where P is a bond, directly to $Lk^2$. In this case, m is greater than 1, for example 2, 3 or 4, up to a maximum of 10. If more than one linker $Lk^1$ is present, these may be the same as each other, or different. Alternatively or in addition, one or more additional therapeutic agent be linked to a multivalent linker $Lk^1$. In this case, q is greater than 1, for example 2, 3 or 4, up to a maximum of 10. Thus, it is possible for the disclosed ADC to carry up to 10 D groups (therapeutic agents). Where it is desired for the conjugate of formula I to contain more than one D group, this may be achieved in any one of a number of ways. For example, multiple $(((D_q\text{-}Lk^1)_m\text{-}P)_p\text{-}Lk^2\text{-}Lk^3)$- groups may be bonded to a single antibody (i.e. n is from 2 to s). This mode of attachment forms one way of providing conjugates containing more than one group D. A second way of providing ADC containing more than one group D is by use of a multivalent linker $Lk^1$, for example a linker $Lk^1$ which contains one or more aspartate and/or glutamate or similar residues as described above (as for example in formulae VI, VIIa and VIIb), allowing multiple D groups to be present (i.e. q is from 2 to 10).

Alternatively or in addition, where $Lk^2$ is a group consisting of from 1 to 9 aspartate and/or glutamate residues, multiple $((D_q\text{-}Lk^1)_m\text{-}P)$— groups may be bonded at different positions on the $Lk^2$ group (i.e. p is from 2 to 10), by amide bonding of each group through an amine moiety with a carboxyl group of an aspartate or glutamate residue in the $Lk^2$ group. Where $P^1$ contains at least one ethylene or ethylene glycol unit and also contains at least one branching unit, multiple $(D_q\text{-}Lk^1)$- groups may additionally or alternatively be bonded at different positions on the $P^1$ group (i.e. m is from 2 to 10).

Different $Lk^3$, $Lk^2$, P, $Lk^1$ and D groups may also be present in the same conjugate, for example where an ADC contains two $((D\text{-}Lk^1)\text{-}P)\text{-}Lk^2\text{-}Lk^3$ groups, one of those $((D\text{-}Lk^1)\text{-}P)\text{-}Lk^2\text{-}Lk^3$- groups can have $Lk^2$ as a bond and the other $((D\text{-}Lk^1)\text{-}P)\text{-}Lk^2\text{-}Lk^3$- group can have an aspartate or glutamate residue as $Lk^2$. Likewise, where a conjugate contains multiple $(D\text{-}Lk^1)_m\text{-}P$ groups bonded to an $Lk^2$ group, one of those groups, P, may be a bond, and another $(D\text{-}Lk^1)_m\text{-}P$ group can have a P group of —$P^1$—NH—. Thus, in its simplest form, the disclosed ADC ca have a single therapeutic agent (n=m=q=p=1). The conjugates may contain up to 10 therapeutic agents (e.g., maytansine moieties). Where two D groups are present, these may for example be in conjugates of the formulae:

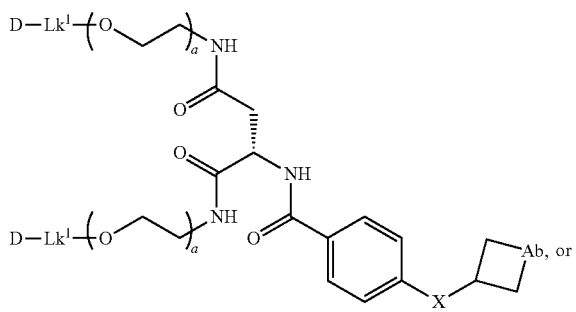

(Ia)

in which $Lk^1$ preferably comprises a group of formula (Va), (Vd) or (Ve) as described above.

Alternatively, where two D groups are present, these may for example be in conjugates of the formulae:

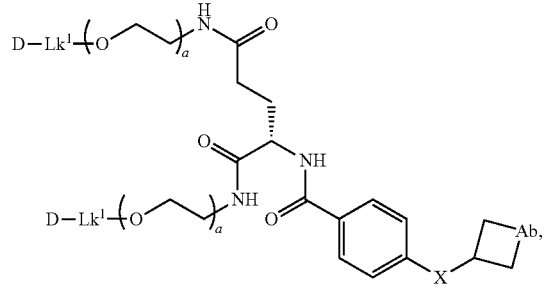

(Ib)

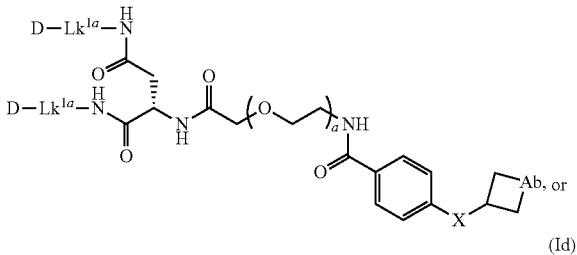

(Ic)

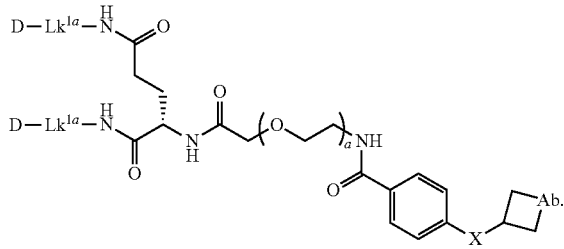

(Id)

The above formulae show the bonding of X across one of the disulfide bonds present in Ab. Antibodies may contain up to 4 inter-chain disulfide bonds, and if each of these bonds is bridged by a reagent carrying a single maytansine molecule, the resulting conjugate will have a drug:antibody ratio (DAR) of 4. If a reagent carrying two maytansine molecules is used to bridge all 4 disulfide bonds, for example a reagent carrying two PE or PEG chains or having a branched PE or PEG chain or having a branched linker $Lk^1$, then the DAR will be 8.

Conjugates of the present invention may be prepared by reducing one or more disulfide bonds in an antibody or antigen binding fragment thereof and subsequently reacting with a conjugating reagent of the general formula:

$((D_q\text{-}Lk^1)_m\text{-}P)_p\text{-}Lk^2\text{-}Lk^{3a}$ (VIII)

in which D, $Lk^1$, P, $Lk^2$ and m, p and q have the meanings given for the general formula I, and $Lk^{3a}$ represents a group of formula:

—CO-Ph-$X^a$—$Y^a$ (IX)

in which Ph has the meaning given above, $X^a$ represents a CO group, and $Y^a$ represents a group selected from:

(X)

(XI)

(XII)

(XIII)

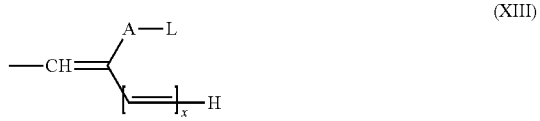

in which A and B have the meanings given above, each L independently represents a leaving group, and x represents an integer from 1 to 4.

Groups of formulae X, XI, XII and XIII above are chemical equivalents of each other, with groups of formula X and XI leading to a single carbon bridge across a disulfide bond of the antibody, and groups of formula XII and XIII leading to longer carbon bridges, shown below for the case where n=1:

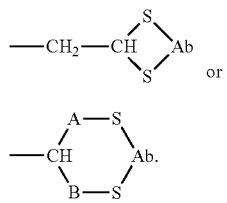

(XIV)

or (XV)

When reacting a conjugating reagent containing a group X or XII with an antibody, the immediate step in the reaction pathway is loss of one leaving group L leading to a conjugating reagent containing a group XI or XIII, respectively. Thus, conjugating reagents of formula XI or XIII are either prepared in situ, or are used ab initio. A key feature of using conjugation reagents containing any of groups X, XI, XII or XIII, is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred and bis-alkylation results from sequential and interactive Michael and retro-Michael reactions. The electron withdrawing group and the leaving group are optimally selected so bis-alkylation can occur by sequential Michael and retro-Michael reactions. It is also possible to prepare cross-functional alkylating agents with additional multiple bonds conjugated to the double bond or between the leaving group and the electron withdrawing group.

A leaving group L may for example represent —SR$^4$, —SO$_2$R$^4$, —OSO$_2$R$^4$, —N$^+$R$^4_3$, —N$^+$HR$^4_2$, —N$^+$H$_2$R$^4$, halogen, or —OØ, in which R$^4$ has the meaning given above, and Ø represents a substituted aryl, especially phenyl, group, containing at least one electron withdrawing substituent, for example —CN, —NO$_2$, —CO$_2$R$^4$, —COH, —CH$_2$OH, —COR$^4$, —OR$^4$, —OCOR$^4$, —OCO$_2$R$^4$, —SR$^4$, —SOR$^4$, —SO$_2$R$^4$, —NHCOR$^4$, —NR$^4$COR$^4$, —NHCO$_2$R$^4$, —NR$^4$CO$_2$R$^4$, —NO, —NHOH, —NR$^4$OH, —C=N—NHCOR$^4$, —C=N—NR$^4$COR$^4$, —N$^+$R$^4_3$, —N$^+$HR$^4_2$, —N$^+$H$_2$R$^4$, halogen, especially chlorine or, especially, fluorine, —C≡CR$^4$, —C=CR$^4_2$ and —C=CHR$^4$, in which each R$^4$ independently has one of the meanings given above. An especially preferred leaving group L is —SR$^4$ or —SO$_2$R$^4$, especially —SO$_2$R$^4$, where R$^4$ represents a phenyl or, especially, a tosyl group. Thus, a particularly preferred group Y$^a$ is:

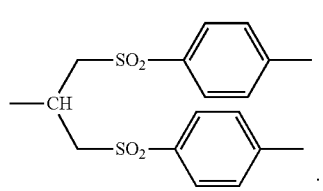

(XIIa)

Examples of preferred conjugating reagents include:

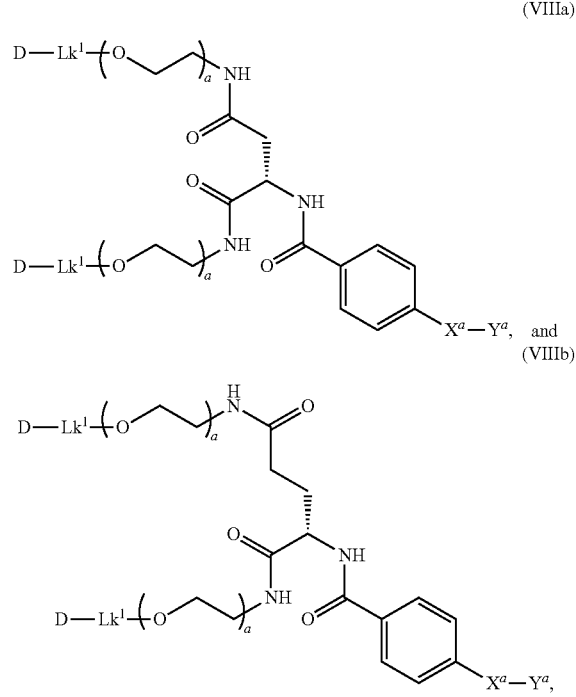

(VIIIa)

and (VIIIb)

in which Lk$^1$ preferably comprises a group of formula (Va), (Vd) or (Ve) as described above, and in which Y$^a$ is preferably a group of formula (XII), especially in which A and B are each —CH$_2$—.

Further preferred examples of conjugating agents include:

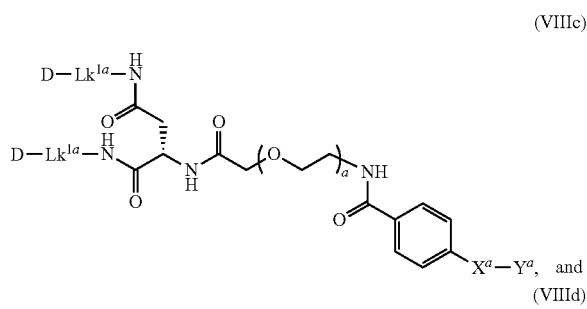

(VIIIc)

and

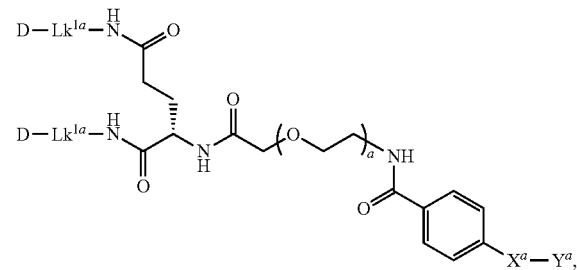

(VIIId)

in which Y$^a$ is preferably a group of formula (XII), especially in which A and B are each —CH$_2$—.

The immediate product of the conjugation process using one of the reagents described above is a maytansine-antibody conjugate in which X represents a keto group CO. However, the process of the invention is reversible under suitable conditions. This may be desirable for some applications, for example where rapid separation of the maytansine from the antibody is required, but for other applications, rapid separation may be undesirable. It may therefore be desirable to stabilize the conjugates by reduction of the CO group X to give a CH.OH group X. Accordingly, the process described above may comprise an additional optional step of reducing the initially-formed CO group X in Lk to give a conjugate having a CH.OH group X in $Lk^3$. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminum alkoxide, and lithium aluminum hydride.

Suitable reaction conditions for the process described above are given in WO 2005/007197 and WO 2010/100430, the contents of which are incorporated herein by reference. The process may for example be carried out in a solvent or solvent mixture in which all reactants are soluble. The antibody may be allowed to react directly with the conjugation reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 8.2. The optimal reaction conditions will of course depend upon the specific reactants employed.

Reaction temperatures between 3-37° C. are generally suitable. Reactions conducted in organic media (for example THF, ethyl acetate, acetone) are typically conducted at temperatures up to ambient. The antibody can be effectively conjugated with the desired reagent using a stoichiometric equivalent or an excess of reagent. Excess reagent and the product can be easily separated during routine purification, for example by standard chromatography methods, e.g. ion exchange chromatography or size exclusion chromatography, diafiltration, or, when a polyhistidine tag is present, by separation using metal affinity chromatography, e.g. based on nickel or zinc. Targeting of specific disulfide bonds in the antibody or antigen binding fragment thereof may be carried out by known methods; for example, by partial reduction of the protein, see for example Liu et al., Anal. Chem. 2010, 82, 5219-5226.

The as-filed application also provides the following non-limiting embodiments:

1. An antibody drug conjugate (ADC) of the general formula:

in which D represents a therapeutic or diagnostic agent;
q represents an integer from 1 to 10;
$Lk^1$ represents a linker;
m represents an integer from 1 to 10;
P represents a bond or a z-valent group —P1-NH— where z is from 2 to 11 and $P^1$ is a group containing at least one ethylene unit —CH$_2$—CH$_2$— or ethylene glycol unit —O—CH$_2$—CH$_2$—;
p represents an integer from 1 to 10;
$Lk^2$ represents a bond or a y-valent linker where y is from 2 to 11 and which consists of from 1 to 9 aspartate and/or glutamate residues;
$Lk^3$ represents a linker of the general formula:

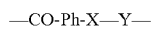

in which Ph is an optionally substituted phenyl group; X represents a CO group or a CHOH group; and Y represents a group of formula:

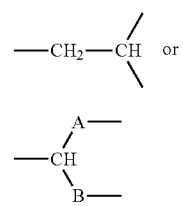

in which each of A and B represents a $C_{1-4}$alkylene or alkenylene group;

Ab represents an antibody or antigen binding fragment thereof selected from a monoclonal antibody that specifically binds an anti-Müllerian hormone type II receptor (AMHR-II) or an antigen binding fragment thereof, a human monoclonal antibody that specifically binds an anti-Müllerian hormone type II receptor (AMHR-II) or an antigen binding fragment thereof, a humanized antibody that specifically binds an anti-Müllerian hormone type II receptor (AMHR-II) or antigen binding fragment thereof, monoclonal antibody 12G4 or antigen binding fragment thereof, a chimeric 12G4 antibody or antigen binding fragment thereof or a humanized 12G4 antibody or antigen binding fragment thereof, said antibody or antigen binding fragment thereof being bonded to $Lk^3$ via two sulfur atoms derived from an interchain disulfide bond in the antibody or antigen binding fragment thereof; and n represents an integer from 1 to s where s is the number of disulfide bonds present in the antibody or antigen binding fragment thereof prior to conjugation to $Lk^3$; and m, n, p, q, y and z are chosen such that the conjugate contains from 1 to 10 D groups.

2. An ADC conjugate according to embodiment 1, wherein the therapeutic agent (D) is selected from maytansine and derivatives thereof, radioactive isotopes, chemotherapeutic agents and toxins.

3. The ADC conjugate according to embodiment 3, wherein the therapeutic agent is selected from $At^{211}$, $I^{131}$, $I^{125}$, $Y^{90}$, $Re^{186}$, $Re^{188}$, $Sm^{153}$, $Bi^{212}$, methotrexate, adriamycin, vinca alkaloids, vincristine, vinblastine, etoposide, doxorubicin, melphalan, mitomycin C, chlorambucil, daunorubicin, enzymes, antibiotics, gelonin, ricin and saporin.

4. The ADC according to any preceding embodiment, in which $Lk^1$ is a degradable linker.

5. The ADC according to embodiment 4, wherein $Lk^1$ is selected from:

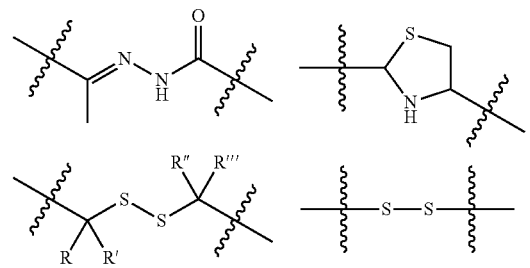

-continued

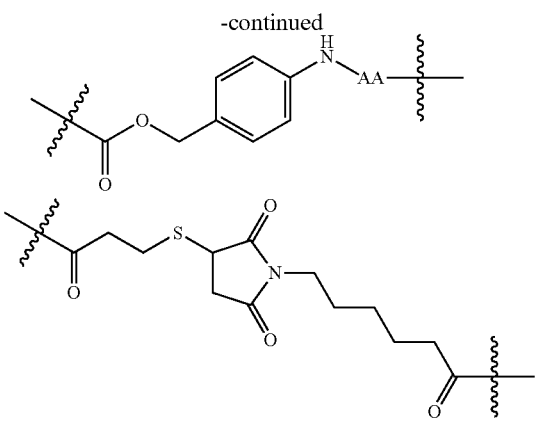

in which each of R, R', R" and R'" represents a hydrogen atom or an alkyl group and AA represents a protease-specific amino acid sequence.

6. The ADC according to embodiment 5, in which $Lk^1$ is:

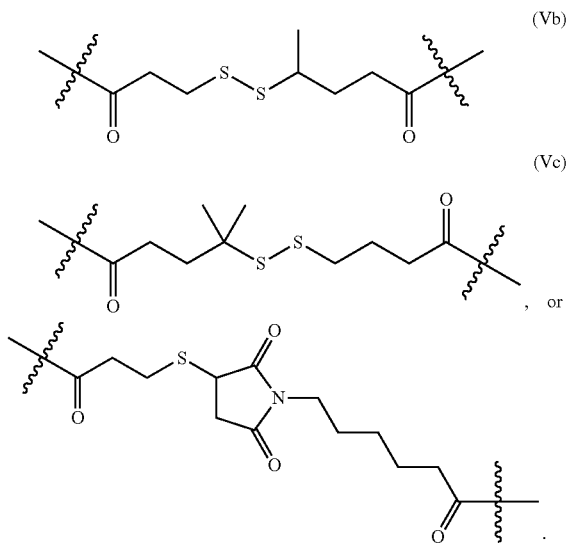

(Vb)

(Vc)

, or

7. The ADC according to embodiment 1 or embodiment 2, in which q is an integer from 2 to 10 and $Lk^1$ is a multivalent linker incorporating one or more aspartate or glutamate residues.

8. The ADC according to any one of embodiments 1-7, in which P represents a bond, or P represents —$P^1$NH— wherein $P^1$ contains from 2 to 10 ethylene glycol units.

9. The ADC according to any preceding embodiment, in which P represents polyethylene glycol.

10. The ADC according to any one of embodiments 1 to 9, in which the phenyl group Ph in Lk3 is unsubstituted.

11. The ADC according to any one of embodiments 1 to 10, in which Y has the formula:

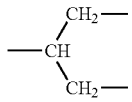

12. The ADC according to any one of embodiments 1-11, wherein said antibody is a humanized 12G4 antibody or an antigen binding fragment thereof.

13. The ADC according to embodiment 1, wherein said humanized antibody or an antigen binding fragment thereof binds AMHR-II and is selected from:

a) a humanized antibody or an antigen binding fragment thereof containing CDRs comprising the following sequences: CDRL-1: RAS$X_1X_2$V$X_3$ $X_4$ $X_5$A (SEQ ID NO: 65), where $X_1$ and $X_2$ are, independently, S or P, $X_3$ is R or W or G, $X_4$ is T or D, and $X_5$ is I or T; CDRL-2 is PTSSL$X_6$S (SEQ ID NO: 66) where $X_6$ is K or E; and CDRL-3 is LQWSSYPWT (SEQ ID NO: 67); CDRH-1 is KASGY $X_7$FT$X_8X_9$HIH (SEQ ID NO: 68) where $X_7$ is S or T, $X_8$ is S or G and $X_9$ is Y or N; CDRH-2 is WIYP$X_{10}$DDSTKYSQKFQG (SEQ ID NO: 69) where $X_{10}$ is G or E and CDRH-3 is GDRFAY (SEQ ID NO: 70);

b) a humanized antibody or an antigen binding fragment thereof comprising a light chain comprising SEQ ID NO: 2 and a heavy chain comprising SEQ ID NO: 4;

c) a humanized antibody or an antigen binding fragment thereof comprising a light chain comprising SEQ ID NO: 6 and a heavy chain comprising SEQ ID NO: 8;

d) a humanized antibody or an antigen binding fragment thereof comprising a light chain comprising SEQ ID NO: 10 and a heavy chain comprising SEQ ID NO: 12;

e) a humanized antibody or an antigen binding fragment thereof comprising a light chain comprising SEQ ID NO: 14 and a heavy chain comprising SEQ ID NO: 16;

f) a humanized antibody or an antigen binding fragment thereof comprising a heavy chain comprising SEQ ID NO: 19 and a light chain comprising SEQ ID NO: 37, 42, 44, 45, 46, 47, 48, 49, 50, 51, 52, 53, 54, 55, 56, 57, 58, 59, 60, 61, 62, 63 or 64;

g) a humanized antibody or an antigen binding fragment thereof comprising a heavy chain comprising SEQ ID NO: 20, 22, 23, 24, 25, 26, 27, 28, 29, 31, 32, 33 or 34 and a light chain comprising SEQ ID NO: 36;

h) a humanized antibody or an antigen binding fragment thereof comprising a heavy chain comprising SEQ ID NO: 20 and a light chain comprising SEQ ID NO: 38;

i) a humanized antibody or an antigen binding fragment thereof comprising a heavy chain comprising SEQ ID NO: 21 and a light chain comprising SEQ ID NO: 39;

j) a humanized antibody or an antigen binding fragment thereof comprising a heavy chain comprising SEQ ID NO: 22 and a light chain comprising SEQ ID NO: 40;

k) a humanized antibody or an antigen binding fragment thereof comprising a heavy chain comprising SEQ ID NO: 28 and a light chain comprising SEQ ID NO: 41;

l) a humanized antibody or an antigen binding fragment thereof comprising a heavy chain comprising SEQ ID NO: 30 and a light chain comprising SEQ ID NO: 42; or m) a humanized antibody or an antigen binding fragment thereof comprising a heavy chain comprising SEQ ID NO: 35 and a light chain comprising SEQ ID NO: 43.

14. A process for the preparation of a conjugate of any one of embodiments 1 to 13, which comprises reducing one or more disulfide bonds in an antibody or antigen binding fragment thereof selected from monoclonal antibody 12G4, a chimeric 12G4 antibody or a humanized 12G4 antibody or thereof, or antigen binding fragments thereof and subsequently reacting with a conjugating reagent of the general formula:

$$((D_q\text{-}Lk^1)_m\text{-}P)_p\text{-}Lk^2\text{-}Lk^{3a}$$ (VIII)

in which D, $Lk^1$, P, $Lk^2$ and m, p and q have the meanings given in embodiment 1, and $Lk^{3a}$ represents a group of formula:

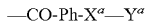     (IX)

in which Ph has the meaning given in embodiment 1, $X^a$ represents a CO group, and $Y^a$ represents a group:

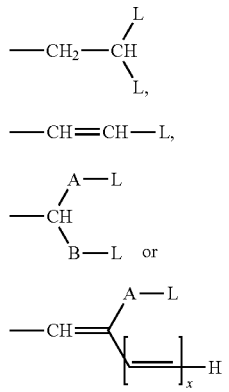

in which A and B have the meanings given in embodiment 1, each L independently represents a leaving group, and x represents an integer from 1 to 4, to produce a conjugate of formula I in which X represents CO; and optionally reducing said initially-formed CO group X to give a conjugate having a CHOH group X.

15. The process according to embodiment 12, in which $Y^a$ represents

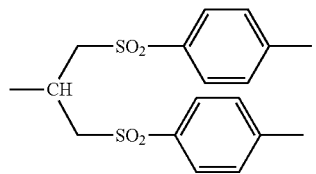     (XIIa)

16. A pharmaceutical composition comprising an ADC according to any one of embodiments 1-13, together with a pharmaceutically acceptable carrier, optionally together with an additional therapeutic agent.

17. An ADC according to any one of embodiments 1-13 or a pharmaceutical composition according to embodiment 16 for use in treatment of a patient having a AMHR-II expressing cancer.

18. A method of treating a patient which comprises administering a pharmaceutically effective amount of an ADC according to any one of embodiments 1 to 13 or a pharmaceutical composition according to embodiment 16 to a subject having a AMHR-II expressing cancers.

19. The use or method according to embodiments 17-18, wherein said method or use comprises the administration of multiple doses of said ADC to said patient.

20. The use or method according to any one of embodiments 17-19, wherein said ADC is administered:
a) as a single weekly ADC dose administered for a period of up to 1 or 2 or 3 months; or
b) consecutive once-weekly ADC doses for up to 4 weeks every 6 months for a period of up to 2 years; or
c) one to 28 daily ADC doses for a period of up to 4 weeks; or
d) two to seven ADC doses, administered once per day, for a period of about two weeks.

21. The use or method according to embodiments 17-20, said use or method further comprising the administration of external radiotherapy, chemotherapy or cytokines or administration of a naked antibody that specifically binds to AMHR-II after the administration of said ADC.

22. The use or method of embodiment 21, wherein a naked antibody is administered subsequent to the administration of said ADC.

23. The use or method of embodiment 22, wherein said naked antibody is administered: a) as a single dose every two to three months; or
b) once weekly for a period of up to four weeks every six months with a duration of the once weekly administration that is between 1 and 4 years; or
c) once weekly for a period of up to six months; or
d) once per month for a period of up to 12 months; or
e) biweekly for a period of up to 52 weeks.

24. An antibody or antigen binding fragment thereof that binds AMHR-II and is selected from:
a) a humanized antibody or antigen binding fragment containing CDRs comprising the following sequences: CDRL-1: $RASX_1X_2VX_3 X_4 X_5A$ (SEQ ID NO: 65), where $X_1$ and $X_2$ are, independently, S or P, $X_3$ is R or W or G, $X_4$ is T or D, and $X_5$ is I or T; CDRL-2 is $PTSSLX_6S$ (SEQ ID NO: 66) where $X_6$ is K or E; and CDRL-3 is LQWSSYPWT (SEQ ID NO: 67); CDRH-1 is KASGY $X_7FTX_8X_9HIH$ (SEQ ID NO: 68) where $X_7$ is S or T, $X_8$ is S or G and $X_9$ is Y or N; CDRH-2 is $WIYPX_{10}DDSTKYSQKFQG$ (SEQ ID NO: 69) where $X_{10}$ is G or E and CDRH-3 is GDRFAY (SEQ ID NO: 70);

b) a humanized antibody or antigen binding fragment comprising a heavy chain comprising SEQ ID NO: 19 and a light chain comprising SEQ ID NO: 37, 42, 44, 45, 46, 47, 48, 49, 50, 51, 52, 53, 54, 55, 56, 57, 58, 59, 60, 61, 62, 63 or 64;

c) a humanized antibody or antigen binding fragment comprising a heavy chain comprising SEQ ID NO: 20, 22, 23, 24, 25, 26, 27, 28, 29, 31, 32, 33 or 34 and a light chain comprising SEQ ID NO: 36;

d) a humanized antibody or antigen binding fragment comprising a heavy chain comprising SEQ ID NO: 20 and a light chain comprising SEQ ID NO: 38;

e) a humanized antibody or antigen binding fragment comprising a heavy chain comprising SEQ ID NO: 21 and a light chain comprising SEQ ID NO: 39;

f) a humanized antibody or antigen binding fragment comprising a heavy chain comprising SEQ ID NO: 22 and a light chain comprising SEQ ID NO: 40;

g) a humanized antibody or antigen binding fragment comprising a heavy chain comprising SEQ ID NO: 28 and a light chain comprising SEQ ID NO: 41;

h) a humanized antibody or antigen binding fragment comprising a heavy chain comprising SEQ ID NO: 30 and a light chain comprising SEQ ID NO: 42;

i) a humanized antibody comprising a heavy chain comprising SEQ ID NO: 35 and a light chain comprising SEQ ID NO: 43;

j) an antibody or antigen binding fragment containing CDRs comprising the following sequences: CDRL-1: $RASX_1X_2VX_3 X_4 X_5A$ (SEQ ID NO: 65), where $X_j$ and $X_2$ are, independently, S or P, $X_3$ is R or W or G, $X_4$ is T or D, and $X_5$ is I or T; CDRL-2 is $PTSSLX_6S$ (SEQ ID NO: 66) where $X_6$ is K or E; and CDRL-3 is LQWSSYPWT (SEQ ID NO: 67); CDRH-1 is KASGY X$_7$FTX$_8$X$_9$HIH (SEQ ID NO: 68) where X$_7$ is S or T, X$_8$ is S or G and X$_9$ is Y or N; CDRH-2 is WIYPX$_{10}$DDSTKYSQKFQG (SEQ ID NO: 69) where X$_{10}$ is G or E and CDRH-3 is GDRFAY (SEQ ID NO: 70);

k) an antibody or antigen binding fragment comprising a heavy chain comprising SEQ ID NO: 19 and a light chain comprising SEQ ID NO: 37, 42, 44, 45, 46, 47, 48, 49, 50, 51, 52, 53, 54, 55, 56, 57, 58, 59, 60, 61, 62, 63 or 64;

l) an antibody or antigen binding fragment comprising a heavy chain comprising SEQ ID NO: 20, 22, 23, 24, 25, 26, 27, 28, 29, 31, 32, 33 or 34 and a light chain comprising SEQ ID NO: 36;

m) an antibody or antigen binding fragment comprising a heavy chain comprising SEQ ID NO: 20 and a light chain comprising SEQ ID NO: 38;

n) an antibody or antigen binding fragment comprising a heavy chain comprising SEQ ID NO: 21 and a light chain comprising SEQ ID NO: 39;

o) an antibody or antigen binding fragment comprising a heavy chain comprising SEQ ID NO: 22 and a light chain comprising SEQ ID NO: 40;

p) an antibody or antigen binding fragment comprising a heavy chain comprising SEQ ID NO: 28 and a light chain comprising SEQ ID NO: 41;

q) an antibody or antigen binding fragment comprising a heavy chain comprising SEQ ID NO: 30 and a light chain comprising SEQ ID NO: 42; or r) an antibody or antigen binding fragment comprising a heavy chain comprising SEQ ID NO: 35 and a light chain comprising SEQ ID NO: 43.

25. An antibody conjugate (AC) comprising the humanized antibody or antigen binding fragment according to embodiment 24 or an antibody or antigen binding fragment thereof selected from a monoclonal antibody that specifically binds an anti-Müllerian hormone type II receptor (AMHR-II) or an antigen binding fragment thereof, a human monoclonal antibody that specifically binds an anti-Müllerian hormone type II receptor (AMHR-II) or an antigen binding fragment thereof, a humanized antibody that specifically binds an anti-Müllerian hormone type II receptor (AMHR-II) or antigen binding fragment thereof, monoclonal antibody 12G4 or antigen binding fragment thereof, a chimeric 12G4 antibody or antigen binding fragment thereof or a humanized 12G4 antibody or antigen binding fragment thereof, said antibody or antigen binding fragment thereof conjugated to a therapeutic or diagnostic agent.

26. The AC according to embodiment 25, wherein said antibody is conjugated to a therapeutic agent selected from maytansine and derivatives thereof, radioactive isotopes, chemotherapeutic agents and toxins.

27. The AC according to embodiment 26, wherein the therapeutic agent is selected from At$^{211}$, I$^{131}$, I$^{125}$, Y$^{90}$, Re$^{186}$, Re$^{188}$, Sm$^{153}$, Bi$^{212}$, P$^{32}$, methotrexate, maytansine and derivatives thereof, adriamycin, vinca alkaloids, vincristine, vinblastine, etoposide, doxorubicin, melphalan, mitomycin C, chlorambucil, daunorubicin, enzymes, antibiotics, gelonin, ricin and saporin.

28. The AC according to any one of embodiments 25-27, wherein the therapeutic or diagnostic agent is conjugated to said antibody via the free amino group of a lysine residue in the heavy chain or light chain of said antibody or said antigen binging fragment of said antibody.

29. The AC according to embodiment 28, wherein said lysine residue is not located in a CDR of said antibody.

30. The AC according to embodiment 25, wherein the diagnostic agent is a fluorescent molecule, a spin label, a radioactive molecule or an enzyme.

31. The AC according to embodiment 25, wherein the diagnostic agent is fluorescein isothiocyanate (FITC), phycoerythrin (PE), indocyanine (Cy5)), alkaline phosphatase, I$^{123}$, I$^{124}$, In$^{111}$, Re$^{186}$, and Re$^{188}$, iodine-123, iodine-131, indium-III, fluorine-19, carbon-13, nitrogen-15, oxygen-17, gadolinium, manganese or iron.

32. A pharmaceutical composition comprising an antibody, antibody conjugate or ADC according to any one of embodiments 24-31, together with a pharmaceutically acceptable carrier, optionally together with an additional therapeutic agent.

33. An ADC according to any one of embodiments 25-29 or a pharmaceutical composition comprising an ADC according to embodiment 32 for use in treatment of a patient having a AMHR-II expressing cancers.

34. A method of treating a patient which comprises administering a pharmaceutically effective amount of an ADC according to any one of embodiments 25 to 29 or a pharmaceutical composition comprising an AC according to embodiment 32 to a subject having a AMHR-II expressing cancers.

35. The use or method according to embodiments 33-34, wherein said method or use comprises the administration of multiple doses of said ADC to said patient.

36. The use or method according to any one of embodiments 33-35, wherein said ADC is administered:

a) as a single weekly ADC dose administered for a period of up to 1 or 2 or 3 months; or b) consecutive once-weekly ADC doses for up to 4 weeks every 6 months for a period of up to 2 years; or c) one to 28 daily ADC doses for a period of up to 4 weeks; or d) two to seven ADC doses, administered once per day, for a period of about two weeks.

37. The use or method according to embodiments 33-36 said use or method further comprising the administration of external radiotherapy, chemotherapy or cytokines or administration of a naked antibody that specifically binds to AMHR-II after the administration of said ADC.

38. The use or method of embodiment 37, wherein a naked antibody is administered subsequent to the administration of said ADC.

39. The use or method of embodiment 38, wherein said naked antibody is administered: a) as a single dose every two to three months; or b) once weekly for a period of up to four weeks every six months with a duration of the once weekly administration that is between 1 and 4 years; or c) once weekly for a period of up to six months; or d) once per month for a period of up to 12 months; or e) biweekly for a period of up to 52 weeks.

40. The method or use according to any one of embodiments 17-23 or 32-39, wherein said AMHR-II expressing cancers is selected from prostate cancer, breast cancer and gynecologic cancers expressing AMHR-II.

41. The method or use according to embodiment 40, wherein said gynecologic cancer expressing AMHR-II is selected from ovarian cancer, metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma.

42. A method of identifying a cancer associated with AMHR-II expression in a subject comprising:

(a) contacting a biological sample of a subject suspected of having a cancer associated with AMHR-II expression with an antibody according to any one of embodiments 1-13 and 24-32 under conditions sufficient for the antibody to form complexes with cells of the biological sample that express AMHR-II; and (b) detecting and/or quantifying said complexes, whereby the detection of said complexes is indicative of a cancer associated with AMHR-II expression.

43. The method according to embodiment 42, said method being repeated at different intervals of time, in order to determine if antibody binding to the samples increases or decreases and determining if said cancer progresses or regresses.

44. The method of embodiments 42-43, wherein said biological sample is prostate tissue, ovaries, vaginal endometrium, uterus, kidney, or any other tissue associated with a cancer selected from ovarian cancer, metastatic ovarian cancer, serous cancer, hypernephroma, endometrioid, colloidal epithelium, prostate cancer, germ cell cancer, endometrial cancer, mixed Müllerian malignant tumor of the uterus, leiomyosarcoma, or endometrial stromal sarcoma.

Example 1

Preparation of the Anti-AMHR-II Antibodies

The humanized low fucose 3C23K antibody was prepared as described in WO2011/141653A1. The murine 12G4 antibody was obtained as described in patent WO 2008/053330. The humanized low fucose 3C23K antibody was used to generate the 3C23K-Antibody Drug Conjugate (ADC) named GM103. This was accomplish by conjugation of 3C23K with a MMAE drug payload as disclosed above.

Example 2

Binding Kinetic Parameters of the 3C23K Antibody

Immobilization of AMHRII was performed on a Bia3000 apparatus at 25° C. in HBS-EP (HEPES 10 mM, NaCl 150 mM, EDTA 3 mM, P20 surfactant 0.005%) at IV/min flow rate on CM5 sensor chip using EDC/NHS (1-Ethyl-3-3-dimethylaminopropyl carbodiimidehydrochloride) activation according to the manufacturer's instructions (GE-Healthcare). Briefly, carboxyl functions of CM5 sensor chip were activated with 0.4M EDC/0.1M NHS during 7 min. A solution of AMHR-II-ECD-Fc (R&D System) at 2.5 µg/ml in sodium acetate buffer was injected during 12 min. An injection of 1M ethanolamine hydrochloride was used to neutralize the activation. Recombinant AMHR-II was covalently immobilized at 1270 RU level. A control reference surface was prepared using the same chemical treatment of without injection of AMHRII.

Antibodies at different concentrations (from 0.5 nM to 133 nM) were injected during 180s on AMHRII-coated flowcell and the control flowcell. After a dissociation step of 400s in running buffer, sensor surfaces were regenerated using 5 µl of Glycine-HCl pH1.7. All the sensorgrams were corrected by subtracting the low signal from the control reference surface. Kinetic parameters were evaluated from the sensorgrams using a Langmuir 1:1 fitting model on the BiaEvaluation 4.2 software.

As mentioned in the Table 1 below, the 3C23K exhibits a high affinity ($5 \times 10^{-11}$M) with a slow dissociation rate ($6.93 \times 10^{-6}$ s$^{-1}$) for the AMHR-II receptor protein. Moreover the 3C23K have a better affinity than the parental murine 12G4 with a 5 times higher association rate and a 3 times lower dissociation rate.

TABLE 1

| | ka (M$^{-1}$ s$^{-1}$) | kd (s$^{-1}$) | KA (M$^{-1}$) | KD (M) | χ2 |
|---|---|---|---|---|---|
| 12G4 | $2.89 \times 10^4$ | $2.28 \times 10^{-5}$ | $1.27 \times 10^9$ | $7.88 \times 10^{-10}$ | 2.74 |
| 3C23K | $1.25 \times 10^5$ | $6.93 \times 10^{-6}$ | $1.81 \times 10^{10}$ | $5.53 \times 10^{-11}$ | 5.34 |

Example 3

Binding of Anti-AMHR-II Antibodies to the Extracellular Domain of AMHR-II Receptor The binding capacity of the anti-AMHR-II 3C23K antibodies was evaluated by ELISA. ELISA plates (96 wells, Maxisorp, NUnc) were coated overnight at +4° C. with 50 ng per well of AMHR-II-ECD-Fc (R&D System). Coated ELISA plates were blocked with PBS-BSA 4% for 2 hours at 37° C. and washed three times with PBS-Tween20 0.05%. The anti-AMHR-II unconjugated 3C23K antibodies and the GM103 were serially diluted in PBST-BSA1% and incubated for 1 hour at 37° C. The bound anti-AMHR-II antibodies were detected by adding HRP-conjugated F(ab')2 goat anti-human F(ab'2) fragment specific (Interchim) diluted at 1:10000 and incubated for one hour at 37° C. Revelation was done with TMB (Sigma) and the reaction was stopped by adding H2SO4 1N (v:v). Absorbances were measured at 450 nm and binding data curves were analysis using GraphPad Prism.

FIG. 1 shows an example of the binding curves of the 3C23K antibodies and EC50 are indicated in the Table 2 below. The unconjugated 3C23K and the GM103 bind to the extracellular domain of AMHR-II in a similar range.

TABLE 2

| | EC50 |
|---|---|
| 3C23K | 0.018 nM |
| GM103 | 0.024 nM |

Example 4

Figure 2:
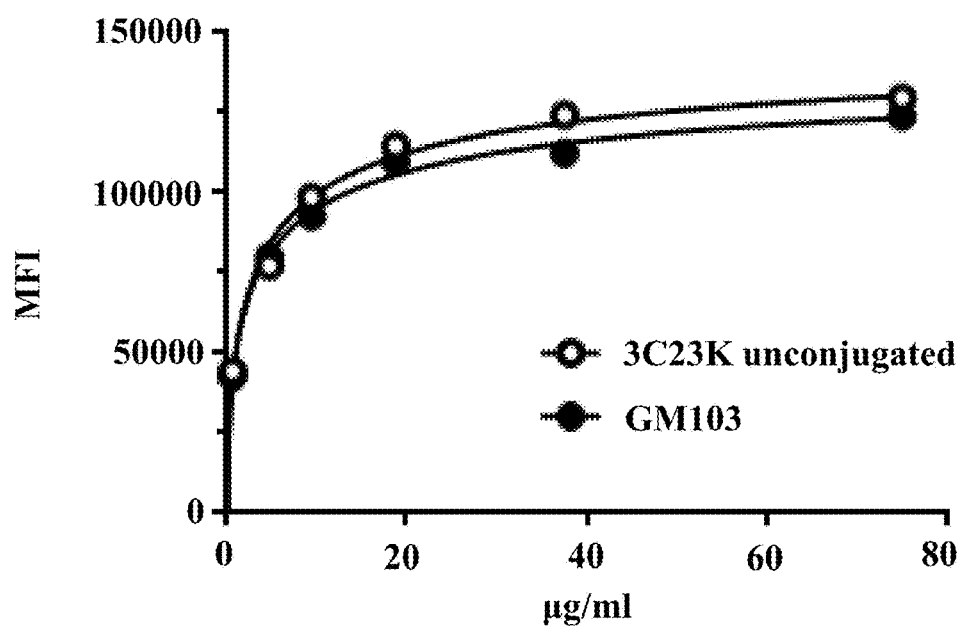
FIG. 2: Binding of the unconjugated 3C23K and GM103 to the AMHR2 receptor expressed at the surface membrane of the COV434 AMHR2 transfected cell line. Binding was determined by FACS analysis in the range of concentrations 0.5 to 75 µg/ml. Binding data curves were analyzed used specific binding with Hill slope equation from GraphPad Prism. GM103 shows similar binding properties than the unconjugated 3C23K antibody with $KD_{apparent}$=3.1 µg/ml.

Binding of Anti-AMHR-II Antibodies to the AMHR-II Receptor at the Surface of Transfected Cell Line The COV434 AMHR-II transfected and the COV434 WT cell lines were maintained in DMEM/GlutaMax (Gibco) supplemented with 10% FBS, penicillin 100 U/ml and Streptomycin 100 µg/ml. Geneticin at 666 µg/ml was added for the COV434 AMHR-II transfected cell line. For Fluorescent-Activated Cell Sorting (FACS) analysis, $5 \times 10^5$ cells were incubated with 3C23K and GM103 antibodies serially diluted from 75 µg/ml to 0.5 µg/ml and incubated 30 min at 4° C. After washes, Phycoerythrin-conjugated anti-human IgG antibody (1:200, Beckman-Coulter) was added for 1 hour at room temperature. FACS analysis of the resuspended cells was done on a BD Accuri™ C6 flow cytometer (BD Bioscience). FIG. 2 shows that no significant change in AMHR-II surface receptor binding was detected for GM103 in comparison to unconjugated 3C23K with a similar $KD_{apparent}$ of 3.1 µg/ml.

Example 5

Binding of the Anti-AMHR-II Antibodies to the FCGRIIIA Receptor (CD16a)

Figure 3:
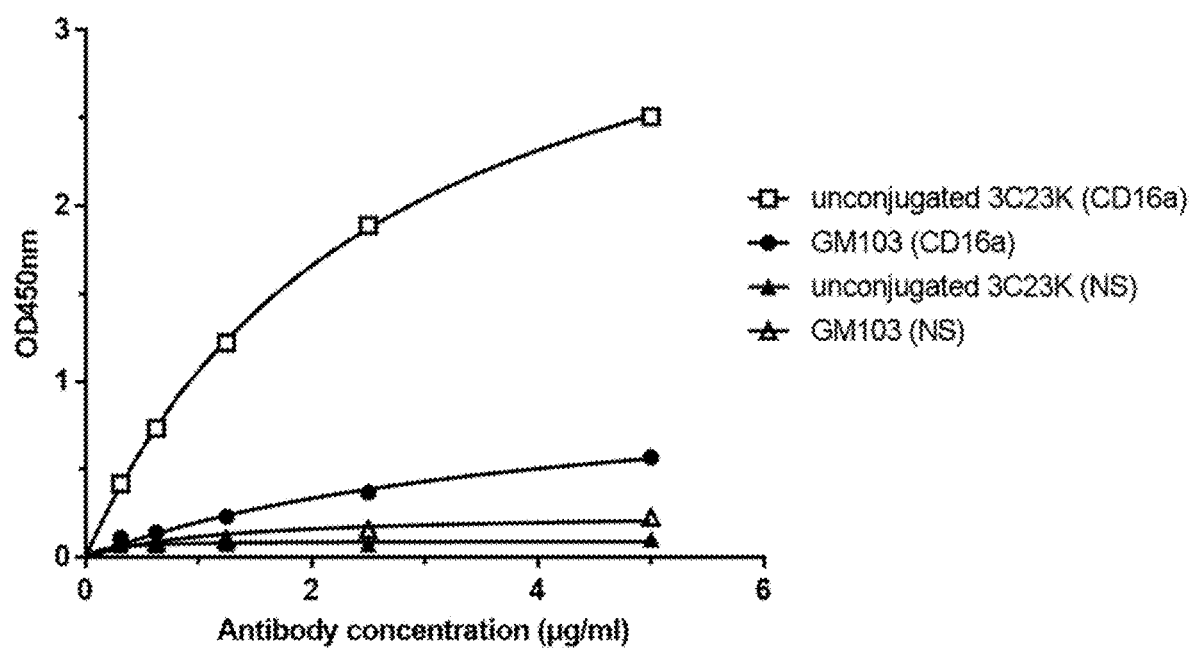
FIG. 3: Binding of the unconjugated 3C23K and GM103 to the CD16a receptor. Binding was determined by ELISA using immobilized extracellular domain of CD16a. NS: non-specific binding on irrelevant protein.

The binding of anti-AMHR-II antibodies to the extracellular domain of CD16a was evaluated by ELISA. ELISA plates (96 wells, Maxisorp, NUnc) were coated overnight at +4° C. with 200 ng per wells of CD16a (R&D System) or an irrelevant protein (NS, non-specific binding). The experimental protocol was identical to that described for example 1. The unconjugated and ADC 3C23K antibodies were tested at concentrations from 0.3 to 5.0 µg/ml. Surprisingly, as shown in FIG. 3, the GM103 exhibits a very low binding to CD16a as compared to the unconjugated 3C23K antibody.

Example 6

In Vitro Cell Proliferation and Cytotoxic Assays

The effects on cells viability was measured using resazurin dye reduction assay (CellTiter Blue, Promega). Cells were plated at 8000 cells per well onto 96-well plate (BD Falcon). After 24 hours at 37° C. under 5% $CO_2$, cells were incubated with serially diluted unconjugated 3C23K or GM103 antibodies in triplicate. Plates were incubated at 37° C. under 5% $CO_2$ for a further 72 hours. In another assay, the specificity of the GM103 effect was evaluated by adding an excess of the unconjugated 3C23K. CellTiter Blue reagent that enable quantification of viable cells by measurement of metabolic activity was added and plates were read with a fluorometer after a minimum of 2 hours with excitation and emission wavelengths of 544 nm and 590 nm respectively. Anti-proliferative effects were evaluated on COV434 AMHR-II transfected cell line (~20000 receptors), COV434 WT (~2000 receptors) and negative cell (no-expression). Data were analyzed using GraphPad Prism and IC50 values, defined as the concentration of antibodies that results in 50% reduction of viability compared with untreated cells, were determined using a 4-parameter non-linear regression model.

Figure 4A:
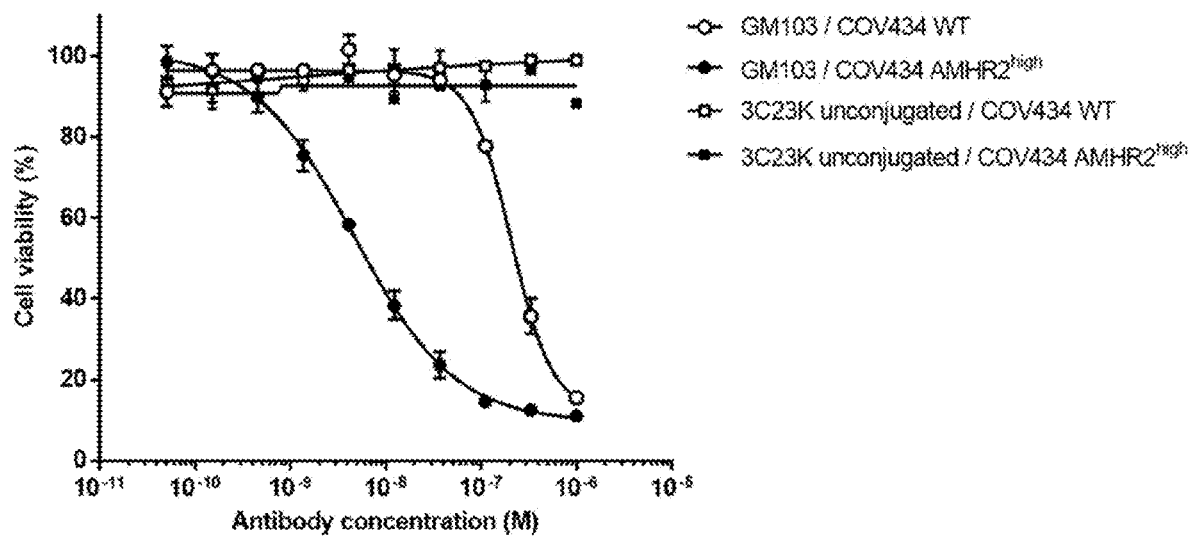
FIGS. 4A-4B: In vitro cell proliferation assay. A) The effects of unconjugated 3C23K and GM103 on cell viability were evaluated with low expressing COV434 WT cell line and high expressing COV434 AMHR-II transfected cell line. Data shown are percentages survival of triplicate wells. B) The AMHR-II receptor surface membrane expression verified by FACS analysis is indicated.
Figure 4B:
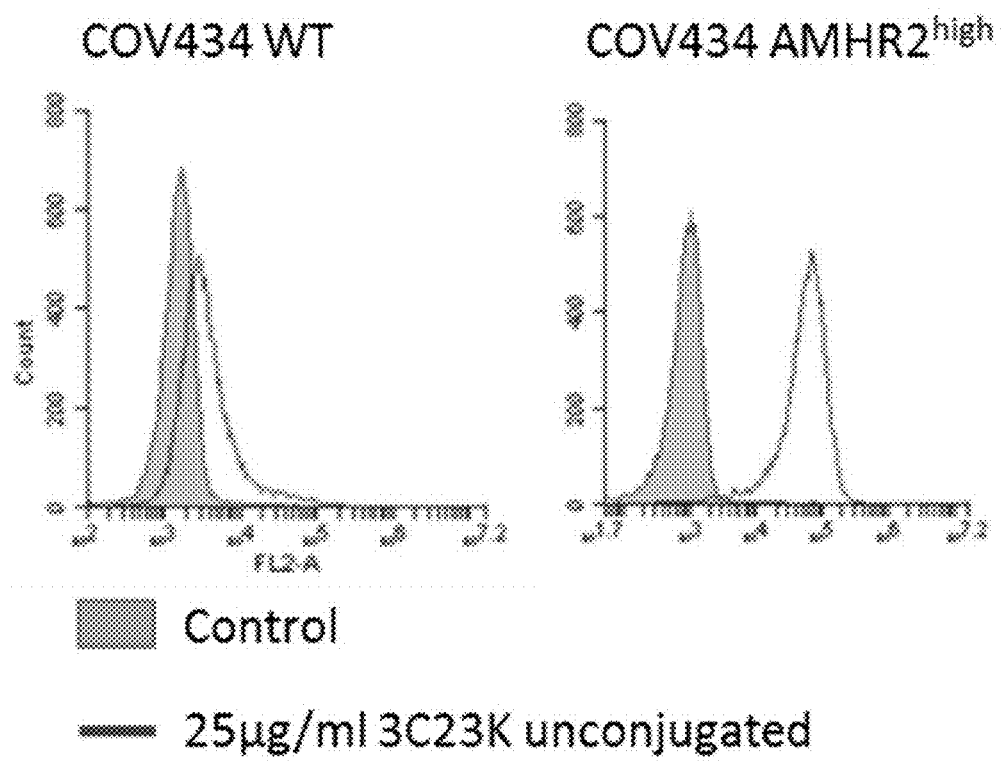
Figure 5A:
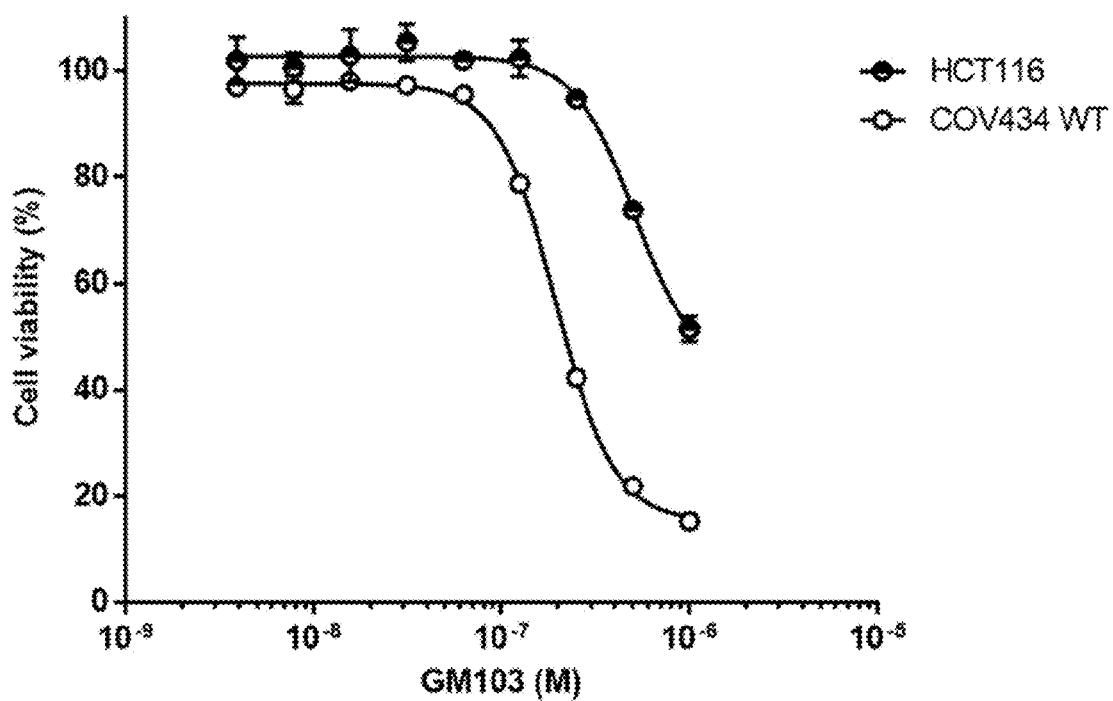
FIGS. 5A-5B: In vitro cell proliferation assay. A) Antiproliferative effect of the GM103 was evaluated with low expressing COV434 WT cell line and with negative HCT116 cancer cell line. B) The level expression of AMHR-II receptor at the membrane surface was evaluated by FACS analysis and is indicated.
Figure 5B:
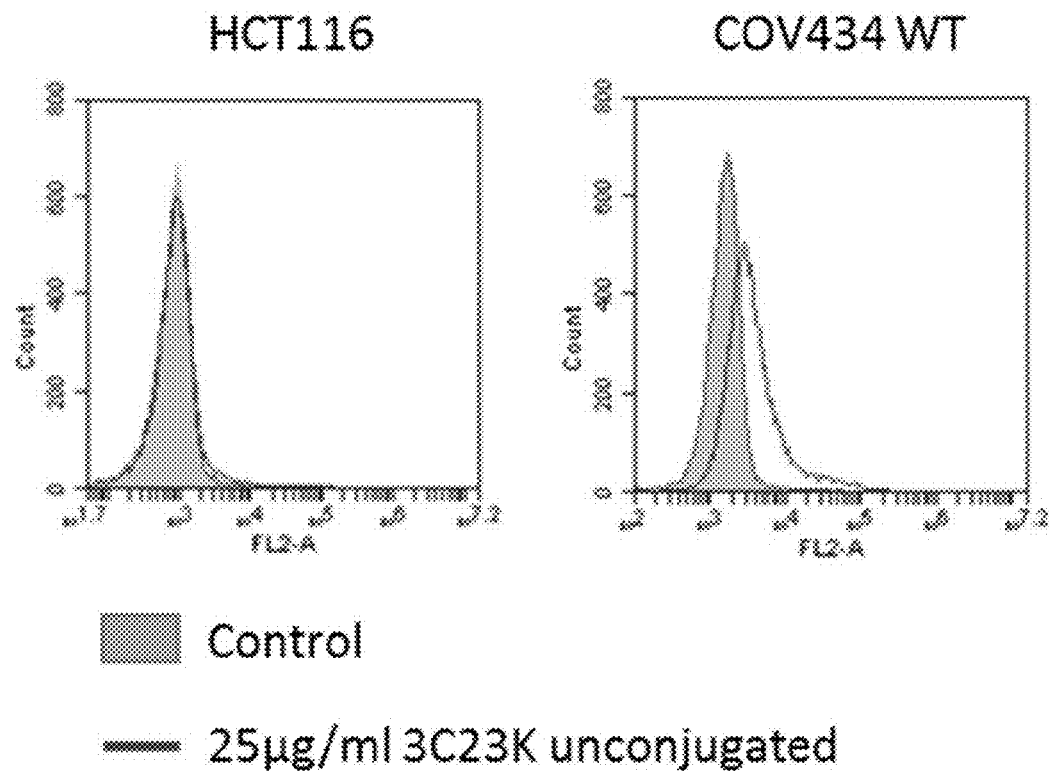
Figure 7:
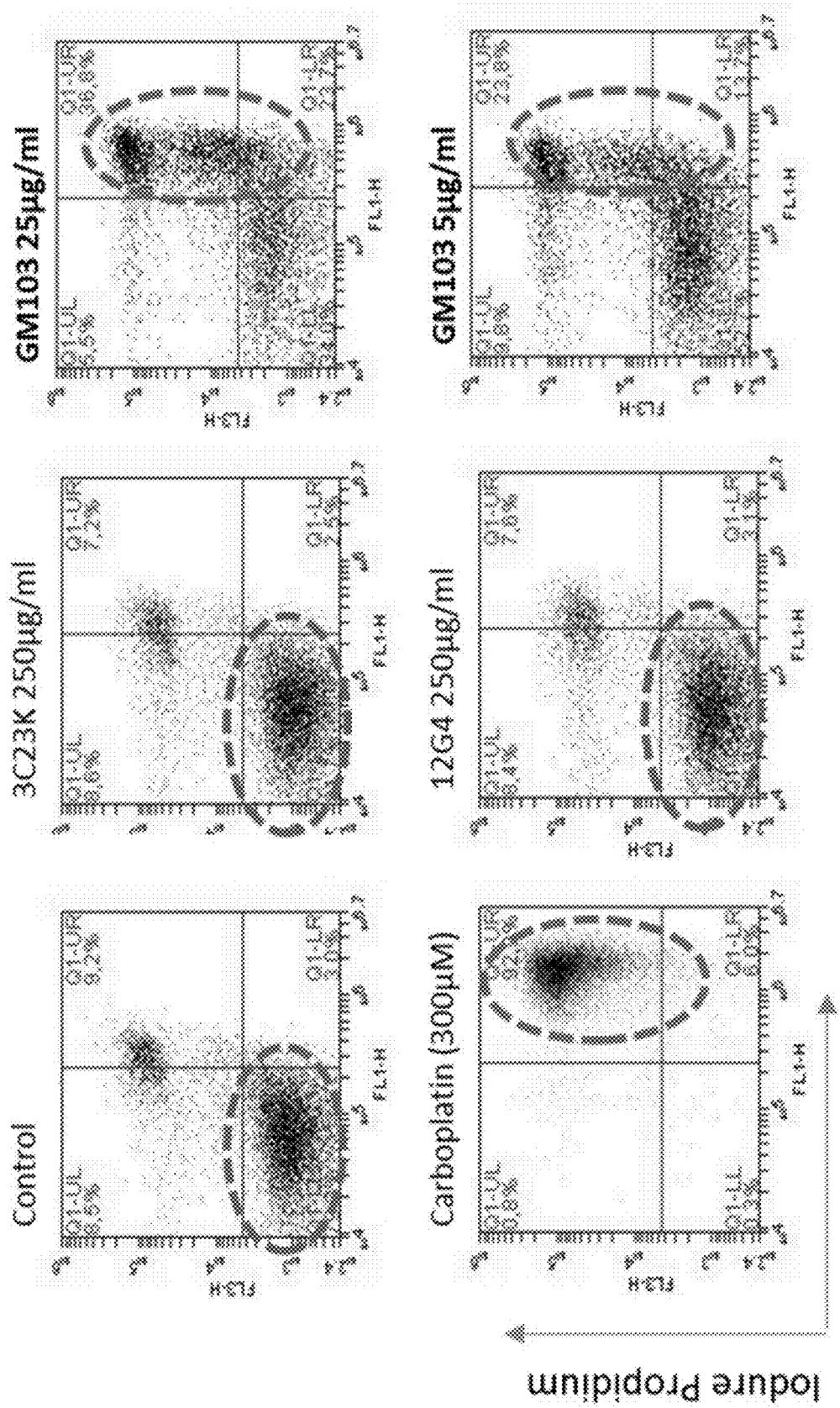
FIG. 7: Apoptosis induction of GM103 in COV434 AMHR-II transfected cell line. Annexin V-FITC and Propidium Iodide were used to detect apoptotic cells after 48H exposure with the GM103.

FIGS. 4 and 5 shows the effects of 3C23K antibodies on cell viability and Table 3 below summarize the IC50 and the minimum viability obtained (ND: could not be calculated).

unconjugated 3C23K (250 µg/ml), 12G4 (250 µg/ml) or GM103 (25 µg/ml and 5 µg/ml) for 48 hours at 37° C. Carboplatin (300 µM) was used as positive control. After washes and centrifugation, the cell pellets were resuspended in the Annexin-V-Fluorescein and propidium iodide reagents. Following 10 minutes incubation at room temperature, samples were analyzed by flow cytometry on a BD Accuri™ C6 flow cytometer (BD Bioscience). FIG. 7 shows that GM103 is effective to induce apoptosis even at 5 µg/ml whilst unconjugated 3C23K or 12G4 antibodies did not induce any apoptosis even at 250 µg/ml.

Induction of apoptosis is confirmed by caspase activation, evaluated using the Apo-ONE Homogeneous Caspase 3/7 assay according to the manufacturer's instruction. Caspase 3/7 activation was measured multiplexed with the proliferation CellTiter Blue assay. Briefly, COV434 AMHR-II transfected or COV434 WT cell lines (10000 cells per well) were incubated with GM103 in dilution series for 72 hours at 37° C. Metabolic activity of viable cells were evaluated by adding the resazurin reagent for 2 hours at 37° C. and fluorescence was recorded at 544 nm excitation and 590 nm emission wavelengths. Then the caspase activity was measured in the same wells by adding the caspase substrate and cells were incubated for another two hours prior fluorescence recording at 485 nm excitation and 538 nm emission wavelengths.

Figure 8A:
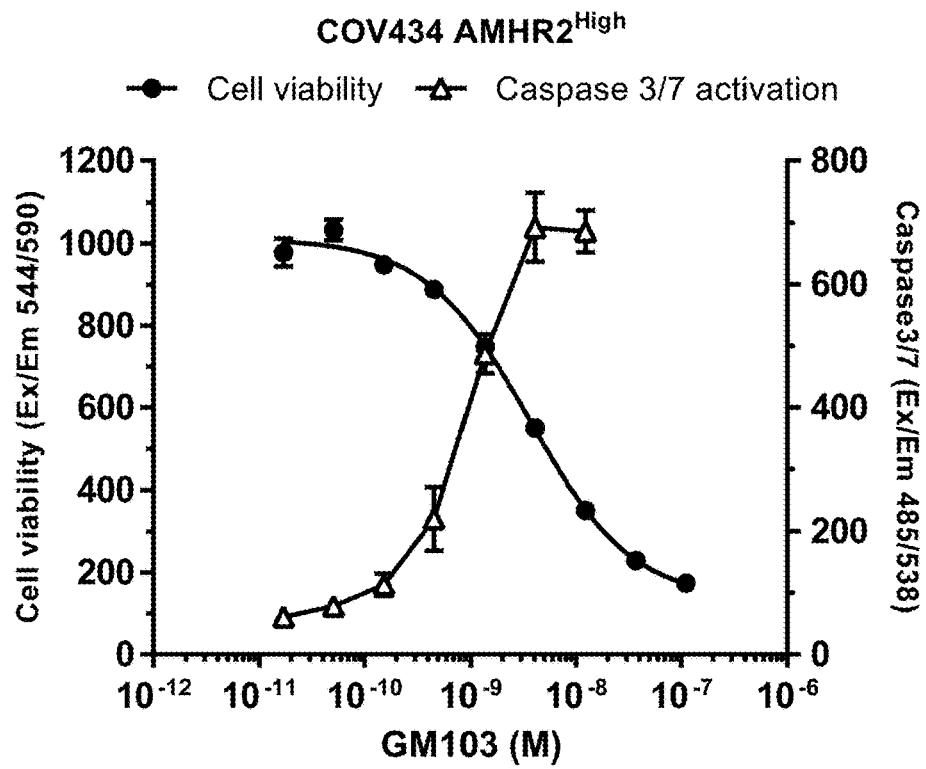
FIGS. 8A-8B: Induction of apoptosis by activation of caspase 3/7 in parallel to measurement of cell proliferation. (A) COV434-AMHR2 transfected and (B) COV434 WT cell lines.
Figure 8B:
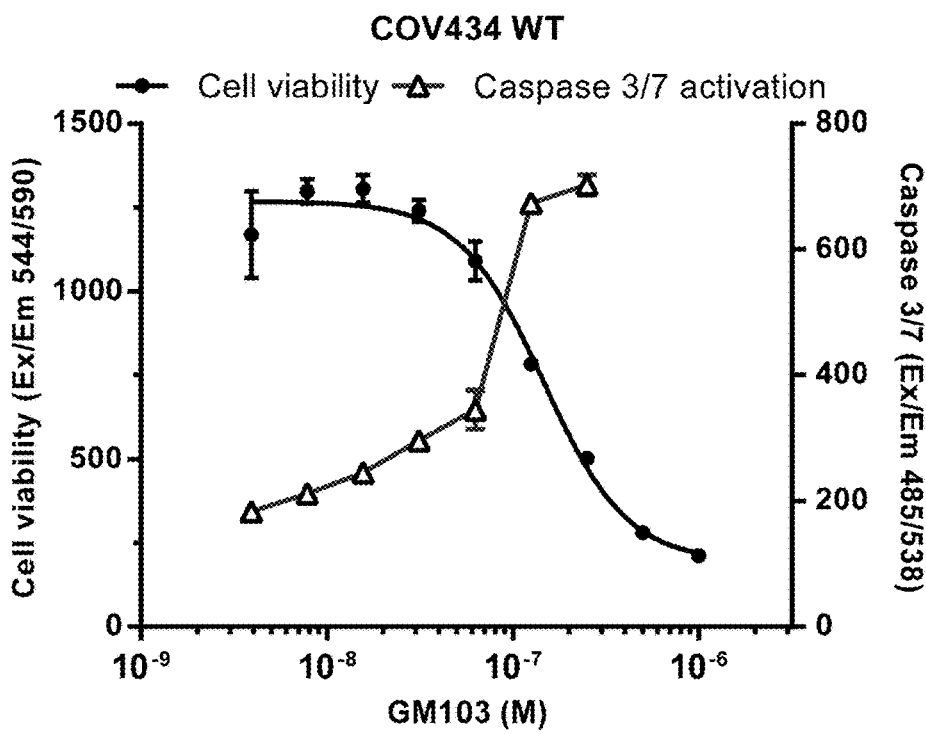

As depicted in FIG. 8, the GM103 is effective to induce apoptosis by activation of the caspase 3/7 in the high expressing COV434AMHR2 transfected cell line but also in the low expressing COV434 WT cell line. In each case, the induction of caspase is synchronized with the diminution of cell viability.

Example 8

Antibody Internalization

Antibody mediated internalization were assessed by flow cytometry analysis and by immunofluorescence imaging. Flow cytometry experiments was done on the two expressing AMHR-II cell lines: COV434 WT with low level of expression and COV434-AMHR-II transfected cell line with high level of expression. Briefly, $5 \times 10^5$ cells were incubated with 3C23K at 10 µg/ml and incubated 30 min at 4° C. After

TABLE 3

|  | COV434 AMHR2$^{High}$ | | COV434 WT | | Negative cell | |
| --- | --- | --- | --- | --- | --- | --- |
|  | IC50 (nM) ± S.E.M | Minimum Viability (%) | IC50 (nM) ± S.E.M | Minimum Viability (%) | IC50 (nM) ± S.E.M | Minimum Viability (%) |
| 3C23K unconjugated | ND | ND | ND | ND | ND | ND |
| GM103 | 4.7 +/− 0.2 | 10% | 208 +/− 21 | 12% | >1000 | ND |

Figure 6:
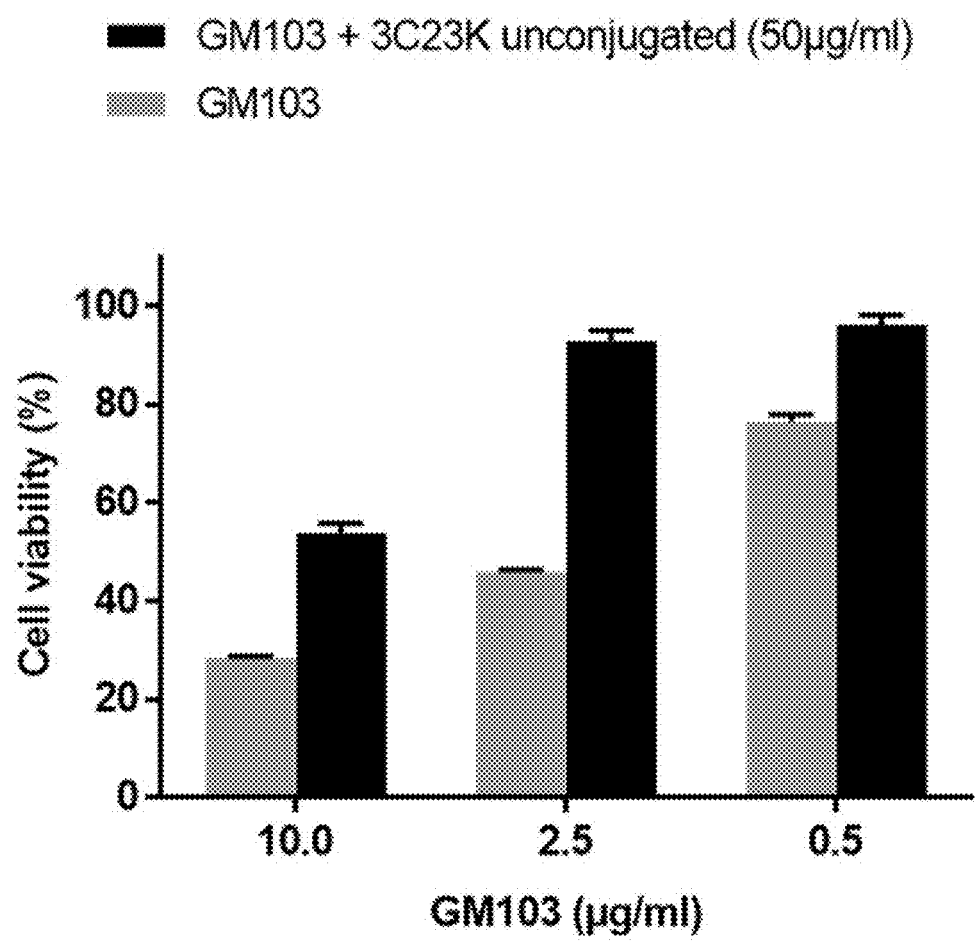
FIG. 6: In vitro competitive cell proliferation assay. A fixed concentration of unconjugated 3C23K (50 µg/ml) was used to inhibit the cytotoxic activity of the GM103 on COV434 AMHR-II transfected cell line

FIG. 6 shows that the anti-proliferative effect of the GM103 is dependent to the binding of antibodies to AMHR-II receptor. Indeed, an excess of unconjugated 3C23K significantly reduces the cytotoxic effect of GM103.

Example 7

Apoptosis Induction

Figure 9A:
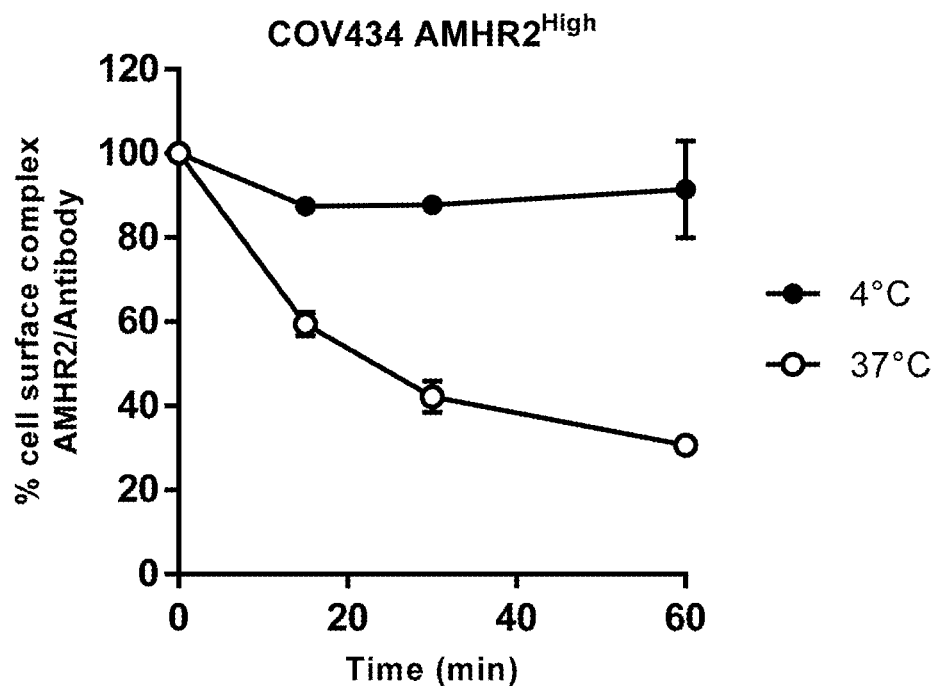
FIGS. 9A-9D: Internalization of unconjugated 3C23K evaluated by flow cytometry on (A) COV434-AMHR2 transfected and (B) COV434 WT cell lines. Visualization by Immunofluorescence of the internalization of 3C23K antibody. C) Time-course microscopy internalization of 3C23K Alexa Fluor 488 in COV434 AMHR-II transfected cells and D) quantification by counting the number of intracellular visible spot.
Figure 9B:
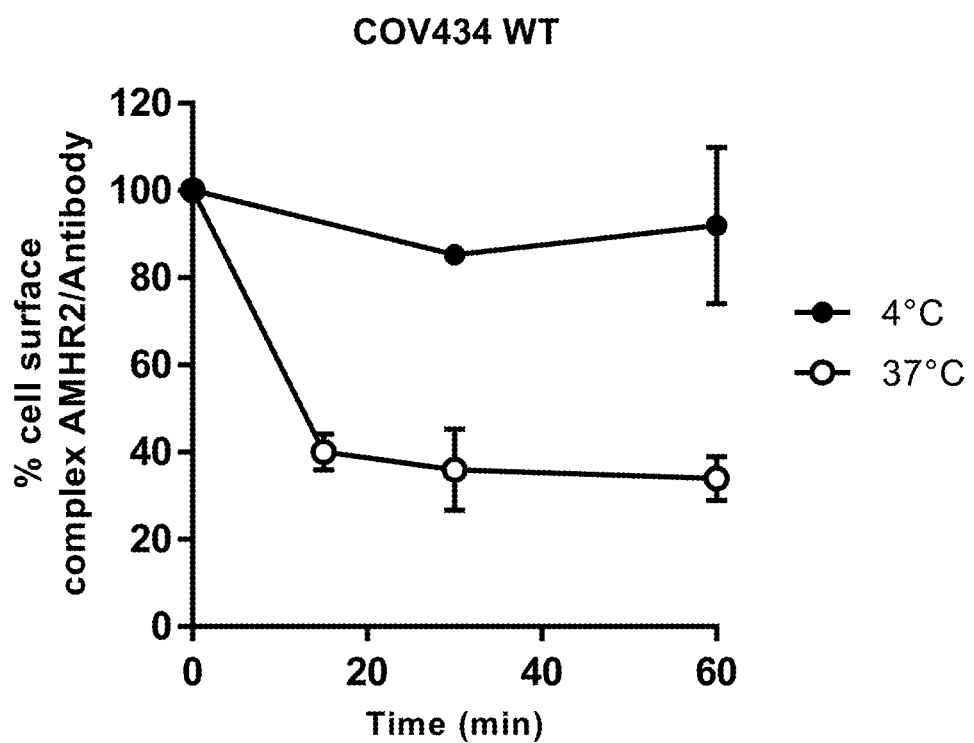

The percentage of apoptotic was assessed using the Annexin V-Fluos Staining kit (Roche) according to the manufacturer's protocol. Briefly, COV434 AMHR-II transfected cell line (25000 cells per well) were incubated with washes, DMEM/GlutaMax (Gibco) medium, cold or pre-warmed at 37° C., was added and incubated at 4° C. or 37° C. at different time points (15 min, 30 min and 60 min). Phycoerythrin-conjugated anti-human IgG antibody (1:200, Beckman-Coulter) was added for 30 min at 4° C. FACS analysis of the resuspended cells was done on a BD Accuri™ C6 flow cytometer (BD Bioscience). As depicted in FIGS. 9A and 9B, the internalization of the 3C23K observed at 37° C. is fast whatever the level of AMHR-II expression. For immunofluorescence imaging experiments, COV434 AMHR-II transfected cell line were grown on poly-D lysine coated glass coverslips overnight at 37° C. at a density of 75000 cells/cm². Cells were incubated with 3C23K directly labelled with Alexa Fluor 488 for 1H30 at 4° C. to carry out surface labelling. Cell surface bound antibodies were allowed to internalize by incubating cells in prewarmed medium at 37° C. At appropriate time points, coverslips were removed and cells were washed in PBS, then fixed in formaline (4%, 30 min at room temperature) and permeabilized (Triton X-100 0.5%, 5 min at room temperature). Nuclei were stained with DAPI (4',6-diamidino-2-phenylindole) and coverslips were mounted on microscope slides and imaged with Leica DM5000 microscope (Leica Microsystems). Internalization was quantified by counting the number of visible vesicles in cell section at different incubation time using Image J software.

Figure 9C:
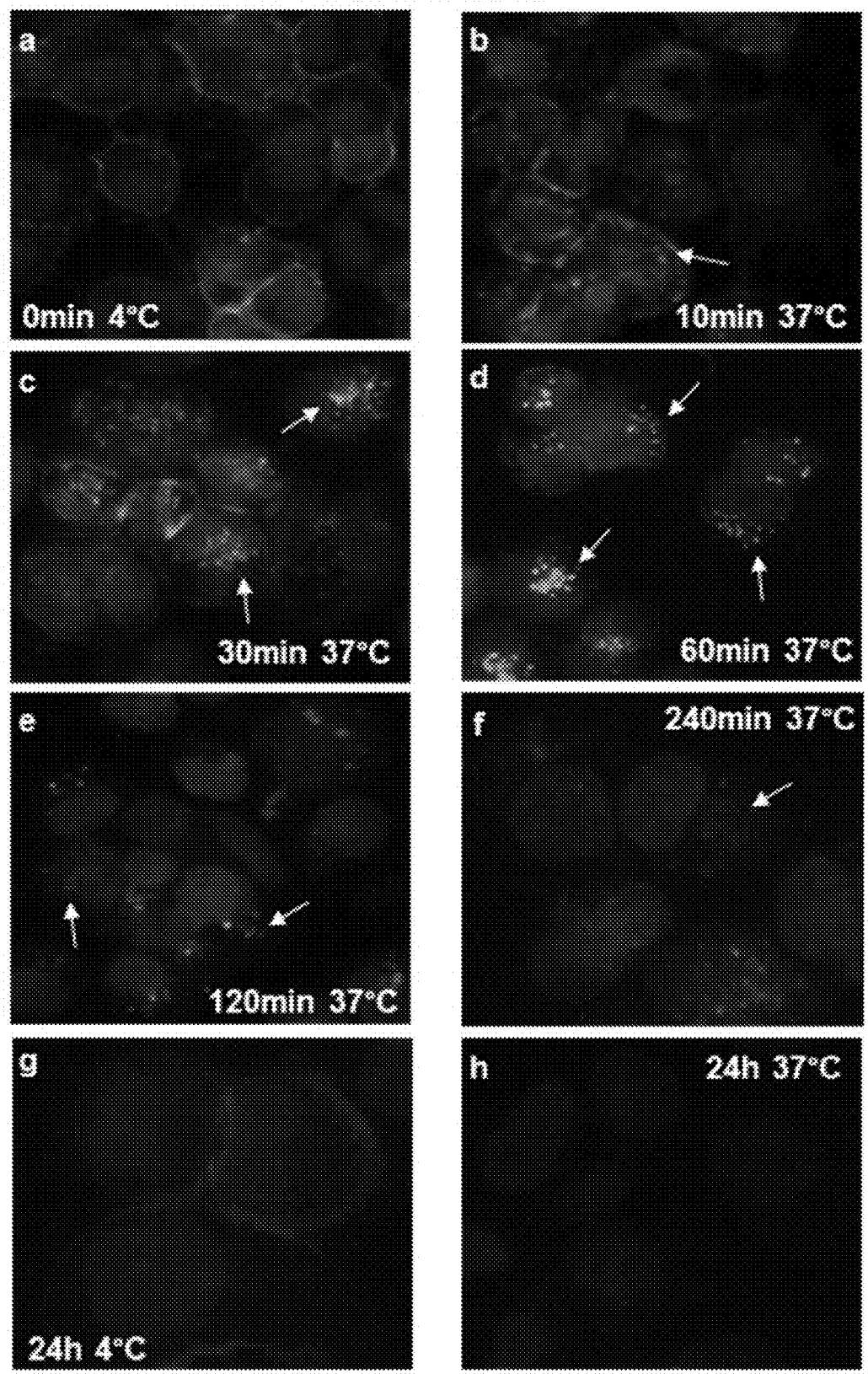
Figure 9D:
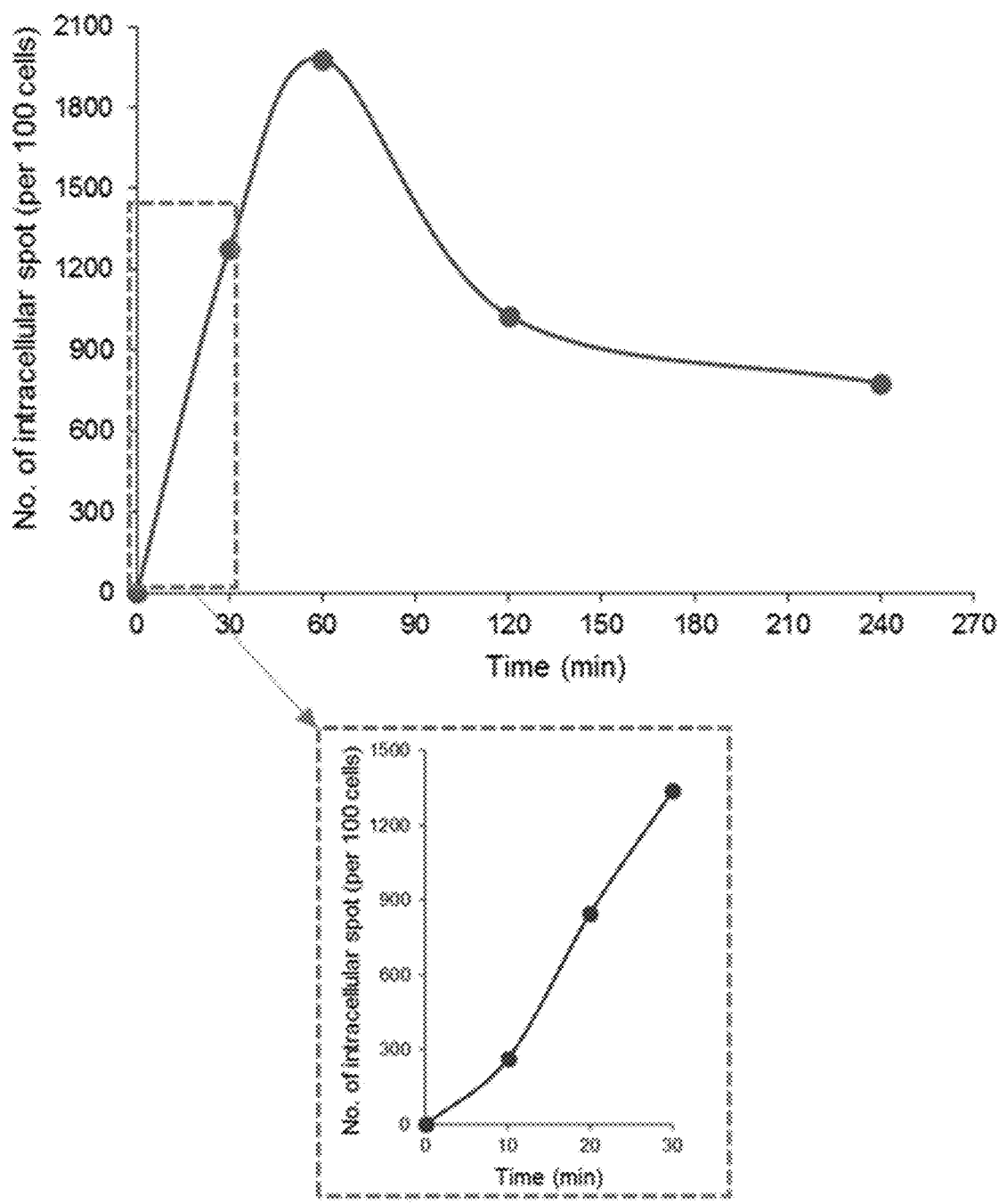
Figure 10A:
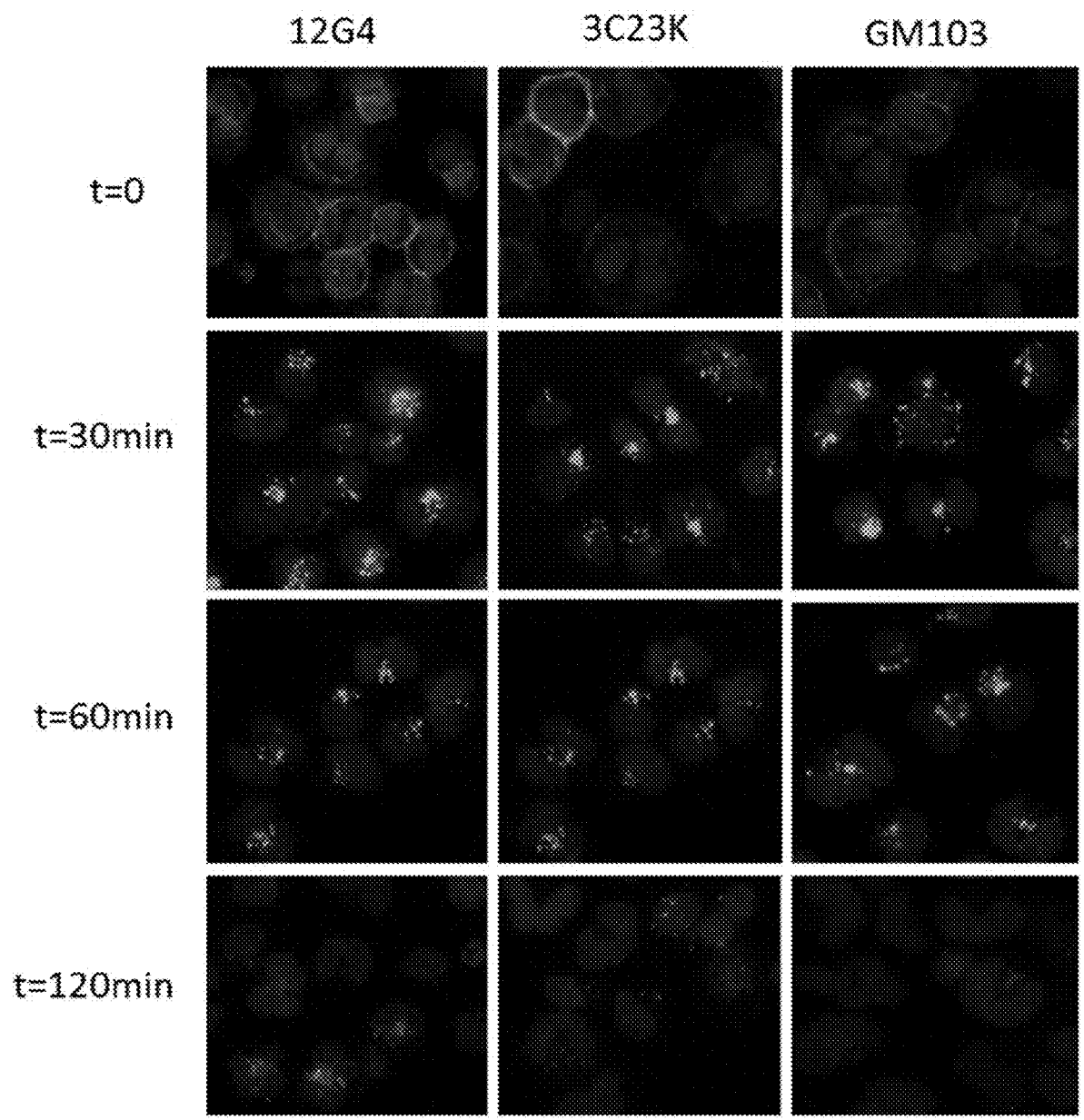
FIGS. 10A-10B: GM103 internalization kinetic is similar to the unconjugated 3C23K antibody. A) Immunofluorescence Imaging. Internalization of parental murine 12G4 antibody is also indicated. Anti-mouse or anti-human FITC conjugated were used to detect anti-AMHR2 antibodies. B) Internalization was evaluated by flow cytometry on COV434 AMHR2 transfected cell line. The majority of the AMHR2 labeling disappeared from the cell surface within 60 minutes.
Figure 10B:
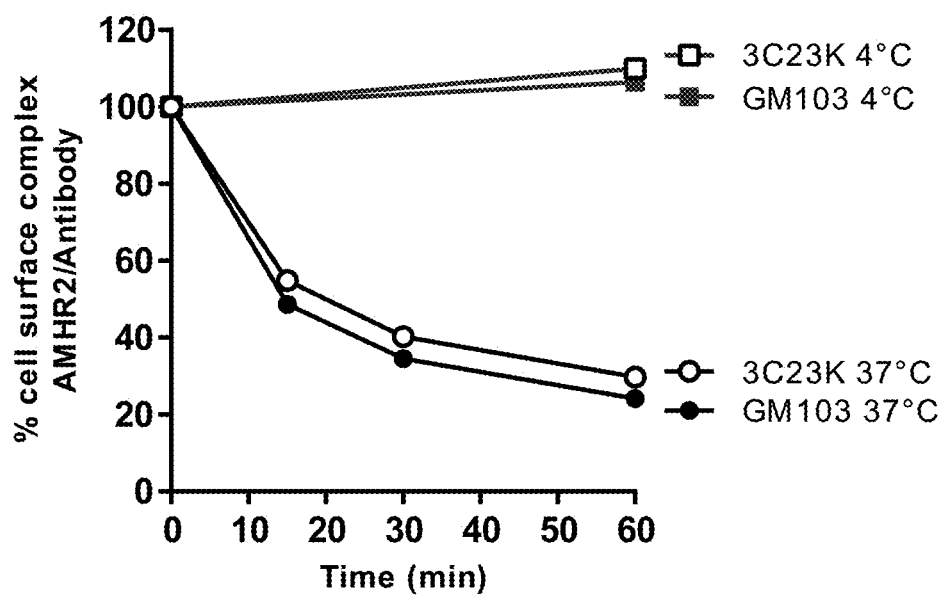

As shown in FIGS. 9C and 9D the 3C23K antibody clearly internalize with a fast rate and a maximum of intracellular location at 60 min. FIG. 10 show that the 3C23K antibody conjugated to the drug payload MMAE (GM103) retains its property of rapid internalization as demonstrated by immunofluorescence imaging (FIG. 10A) and by flow cytometry internalization experiments (FIG. 10B)

Figure 11:
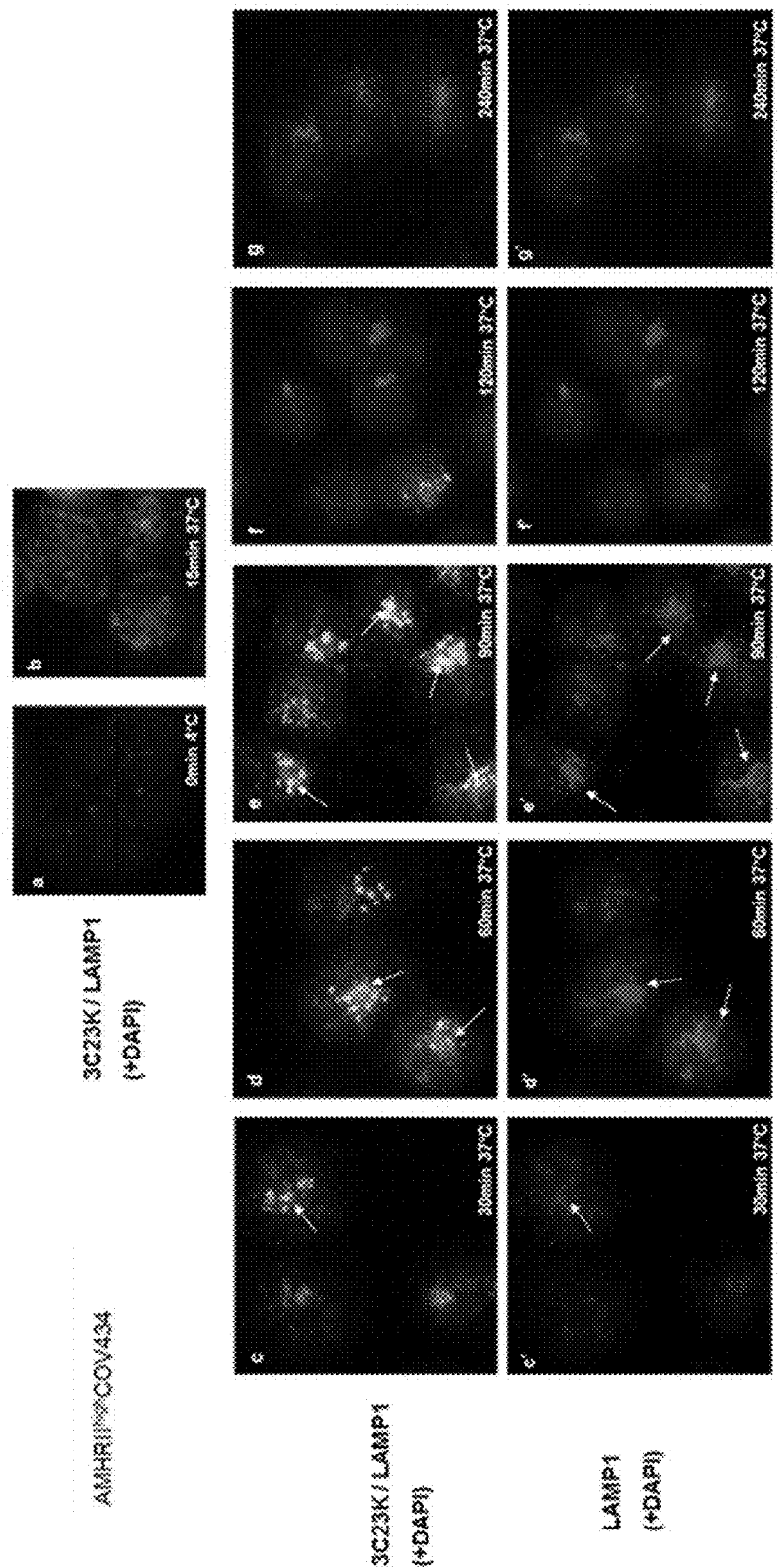
FIG. 11: Co-localization of the 3C23K with the marker of lysosomes LAMP-1.

Lysosomal compartments were visualized with a rabbit anti-LAMP1 antibody (Abcam) following by Alexa Fluor 647 anti-rabbit antibody (Life Technologies). Lysosomal staining was made before nuclei staining with DAPI. As depicted in FIG. 11, the 3C23K antibody is rapidly detected in the lysosomal compartment as demonstrated by the colocalization with the LAMP-1 lysosomal marker.

Figure 12:
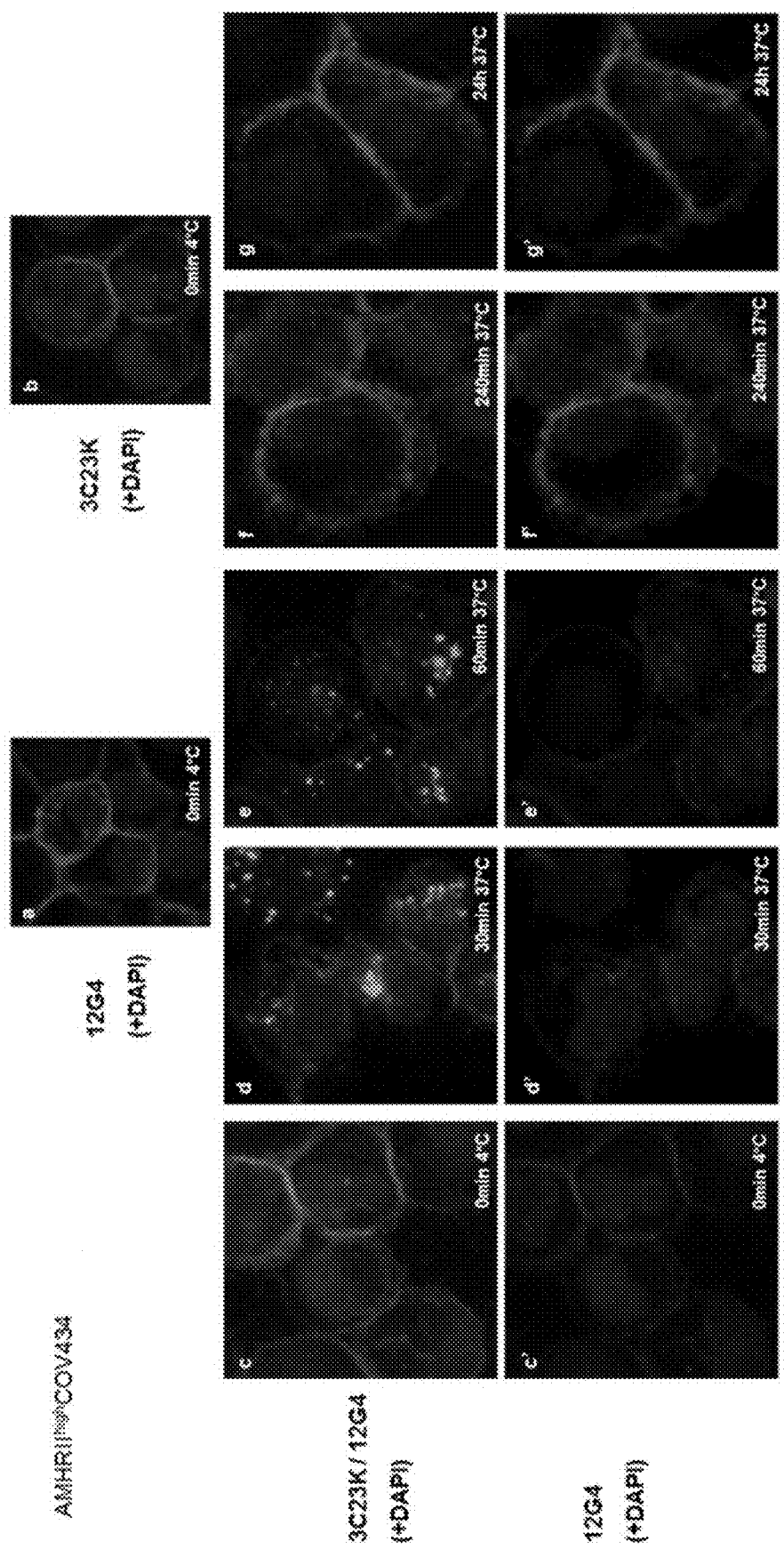
FIG. 12: Recycling of the AMHR-II receptor at the surface membrane after internalization and degradation of the 3C23K antibody.

Recovery of the AMHR-II receptor to the cell surface was investigated after internalization of the Alexa Fluor 488 3C23K. After incubation at several time points at 37° C. to induce internalization, cells were fixed as described previously and the anti-AMHR-II murine 12G4 was used to label the remaining surface AMHR-II receptor. The surface bound 12G4 receptor was detected by a conjugated Alexa Fluor 647 anti-mouse antibody (Life Technologies). FIG. 12 shows that after 240 min, the AMHR-II returns to the surface membrane by recycling.

Example 9

Figure 13A:
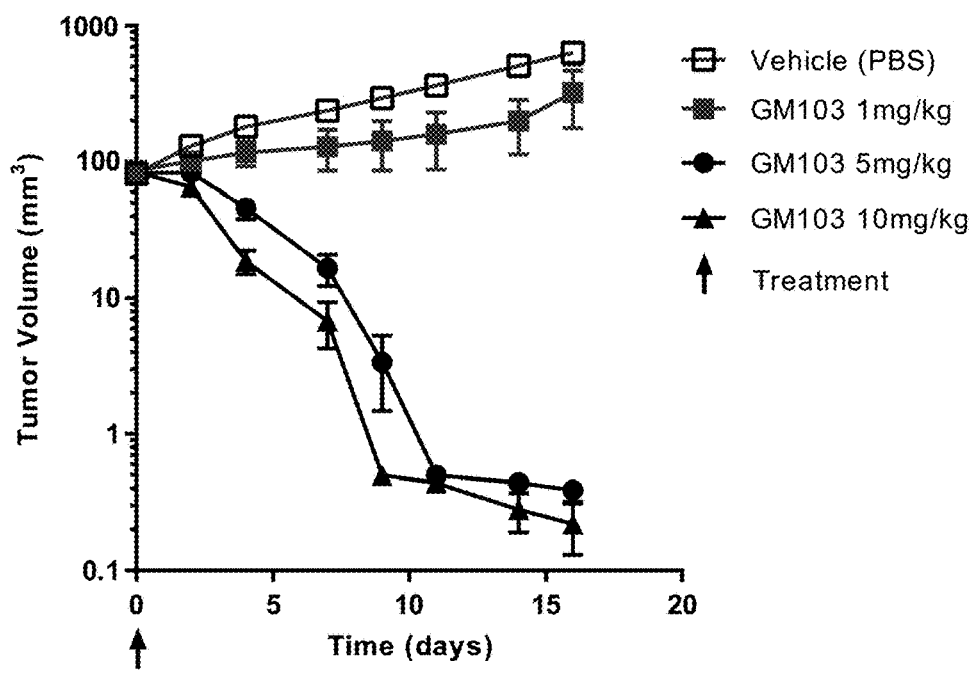
FIGS. 13A-13C: In vivo efficacy of GM103 against xenograft model derived from COV434 AMHR2 transfected cell line. Nude mice (n=9/group) with established tumour (~100 mm3) were treated by intravenous single injection of GM103 at 10, 5 and 1 mg/kg. A) Dose dependent tumor growth shrinkage over 16 days, data shown are mean tumor volumes±S.E.M. per group, B) Individual mouse tumor volume per group of treatment over 16 days. C) Tumor growth inhibition over 70 days.
Figure 13B:
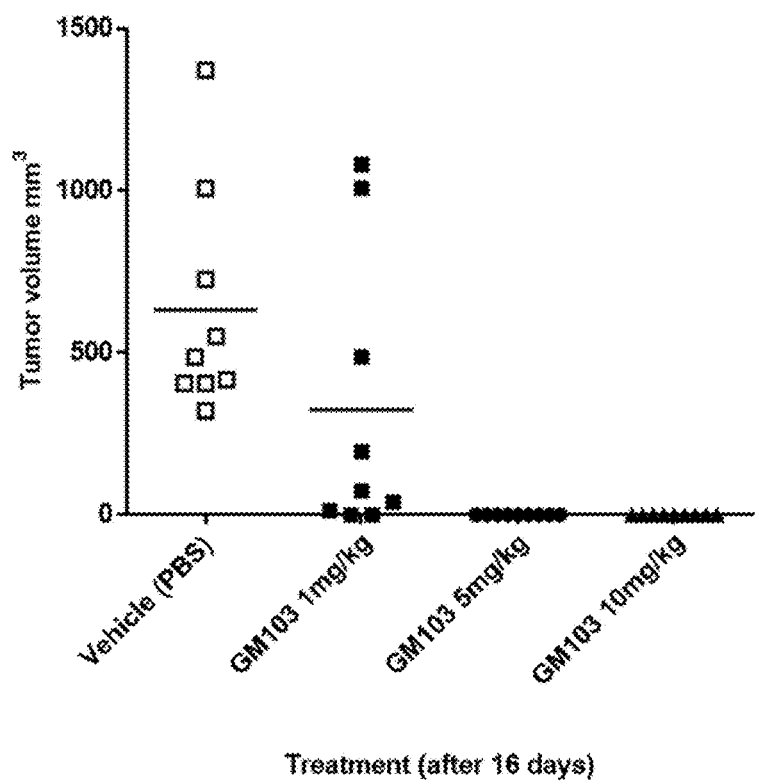
Figure 13C:
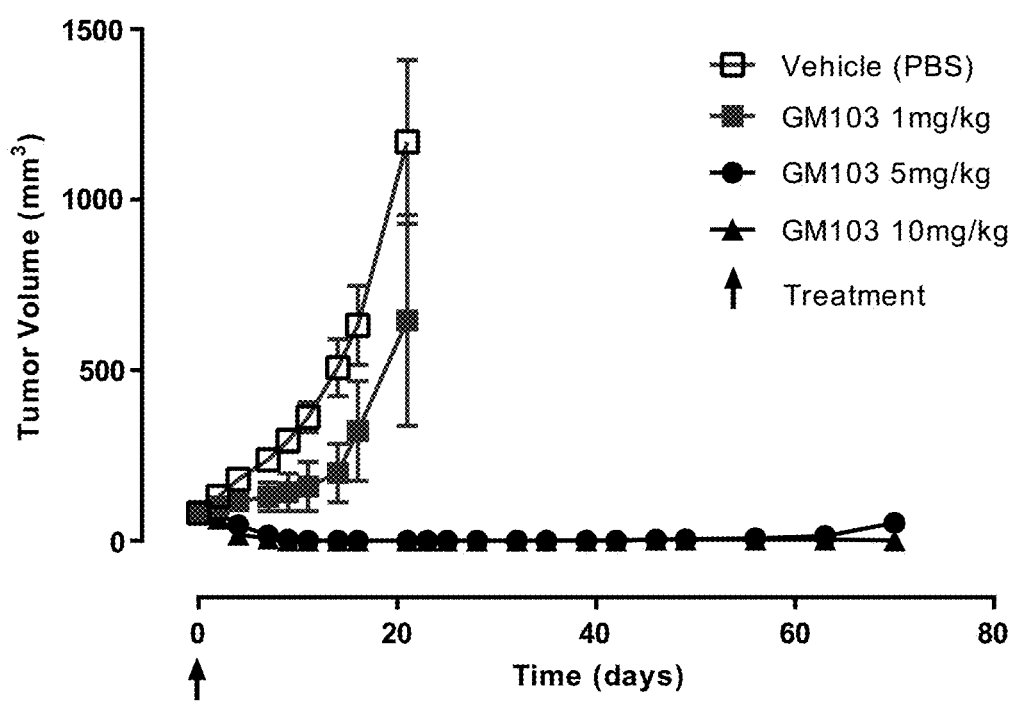

Dose Response of GM103 in COV434 AMHR-II Transfected Cell Line Tumor Xenograft in Nude Mice A COV434 AMHR-II transfected cell line were cultured as described in example 2 and implanted in female athymic nude mice (Hsd:Athymic Nude-Fox1nu, Harlan Laboratories). $10 \times 10^6$ cells (100 μl) were injected in the interscapular mammary fat pad of the mice with matrigel. Mice were allocated to different group according to their tumor volume to give homogenous mean and median tumor volume in each treatment arms. For each group, 10 mice with established growing tumors and tumors volume ranging 60 to 200 mm$^3$ were included in the study. The GM103 was administered once intravenously at 10 mg/kg, 5 mg/kg or 1 mg/kg. The corresponding vehicle (PBS) was administrated on the same day. During the whole experimental period, from grafting to study termination, animals were observed every day, for physical appearance, behavior and clinical changes. Tumor volume was evaluated by measuring tumor diameters three times a week and their size was calculated as mm$^3$=0.5× (tumor length, mm)×(tumor width, mm)$^2$ with the length and the width are the longest and the shortest diameters respectively. As shown in FIG. 13, a dose dependent inhibition of tumor growth is observed for mice treated with the GM103 compared to the vehicle control group with a shrinkage of the tumor (FIG. 10A) and a long term effect of the GM103 over 70 days (FIG. 10C). The data is also provided in the following table (Table 4).

TABLE 4

| COV434-AMHR2$^{High}$ xenografts Tumor volumes (mm$^3$, mean ± sem) | | | | | | | | | |
|---|---|---|---|---|---|---|---|---|---|
| Compound (i.v., once on day 0) | Day 0 | Day 2 | Day 4 | Day 7 | Day 9 | Day 11 | Day 14 | Day 16 | Day 21 |
| Vehicle (PBS) | 82 ± 7 | 130 ± 9 | 180 ± 18 | 237 ± 23 | 294 ± 32 | 362 ± 44 | 508 ± 84 | 632 ± 116 | 1169 ± 240 |
| GM103 1 mg/kg | 86 ± 10 | 101 ± 15 | 116 ± 24 | 129 ± 43 | 142 ± 56 | 159 ± 72 | 199 ± 86 | 322 ± 146 | 647 ± 309 |
| GM103 5 mg/kg | 83 ± 7 | 83 ± 9 | 46 ± 8 | 17 ± 4 | 3 ± 2 | 1 ± 0 | 0 ± 0 | 0 ± 0 | 0 ± 0 |
| GM103 10 mg/kg | 84 ± 8 | 66 ± 9 | 19 ± 4 | 6.78 ± 3 | 0.5 ± 0 | 0 ± 0 | 0 ± 0 | 0 ± 0 | 0 ± 0 |
| Compound (i.v., once on day 0) | Day 23 | Day 25 | Day 28 | Day 32 | Day 35 | Day 39 | Day 42 | Day 46 | Day 49 |
| Vehicle (PBS) | | | | | | | | | |
| GM103 1 mg/kg | | | | | | | | | |
| GM103 5 mg/kg | 0 ± 0 | 0 ± 0 | 0 ± 0 | 0 ± 0 | 0 ± 0 | 0 ± 0 | 0 ± 0 | 3 ± 2 | 5 ± 2 |
| GM103 10 mg/kg | 0 ± 0 | 0 ± 0 | 0 ± 0 | 0 ± 0 | 2 ± 1 | 2 ± 1 | 2 ± 1 | 3 ± 2 | 3 ± 2 |
| Compound (i.v., once on day 0) | Day 56 | | | Day 63 | | | Day 70 | | |
| Vehicle (PBS) | | | | | | | | | |
| GM103 1 mg/kg | | | | | | | | | |
| GM103 5 mg/kg | 8 ± 2 | | | 14 ± 5 | | | 52 ± 26 | | |
| GM103 10 mg/kg | 3 ± 2 | | | 3 ± 2 | | | 2 ± 1 | | |

Example 10

Figure 15A:
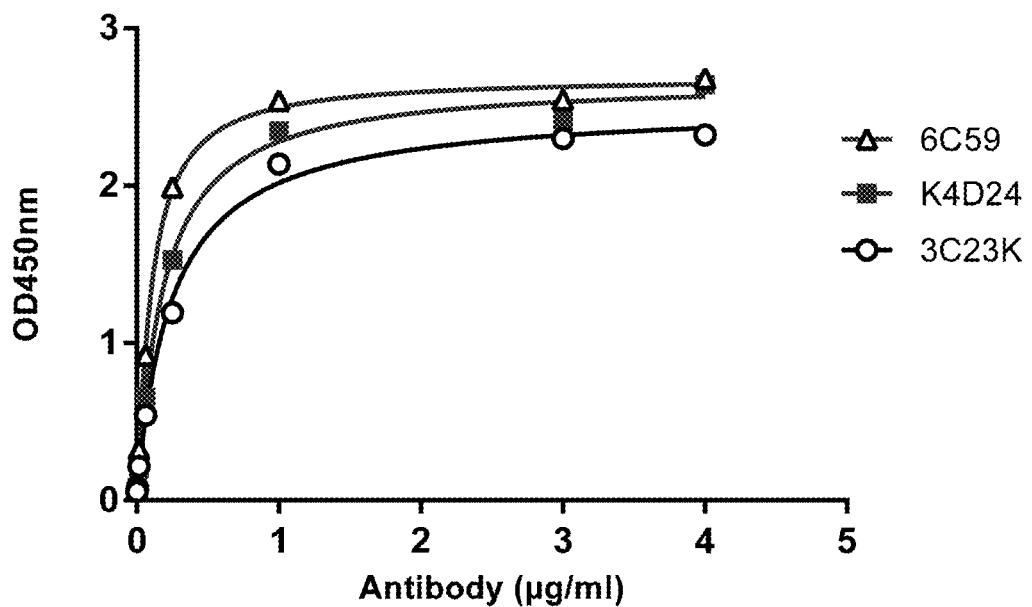
FIGS. 15A-15B: Binding of the variants K4D24 and 6C59 to the extracellular domain of AMHR2 receptor in an ELISA assay with A) a coating at 50 ng/well of the AMHR-II receptor and B) a coating at 10 ng/well. Improved binding of K4D24 and 6C59 was observed when using low amount of coated AMHR-II recombinant protein.
Figure 15B:
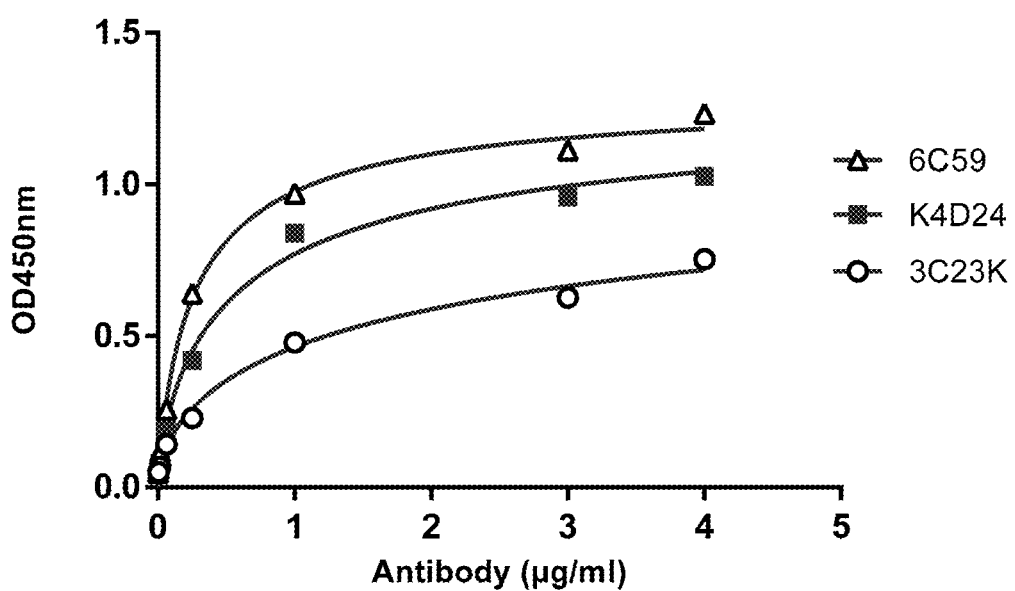

Binding of Variants Antibodies K4D24 and 6C59 to the Extracellular Domain of AMHR-II Receptor The binding capacity of the anti-AMHR-II variants K4D24 and 6C59 antibodies was assayed by ELISA assay as the same manner as in example 3 with only minor changes. ELISA plates (96 wells, Maxisorp, NUnc) were coated overnight at +4° C. with 50 ng per well or 10 ng per well of AMHR-II-ECD-Fc (R&D System). K4D24, 6C59 and 3C23K were serially diluted from 4 µg/ml to 1 ng/ml. Absorbances were measured at 450 nm and binding data curves were analysis using four-parameter nonlinear regression fit from GraphPad Prism. FIGS. 15A-15B show the results. While no major difference of binding between 3C23K and the variants was observed with a coating of 50 ng/well of AMHR-II recombinant protein, the capacity of binding of the K4D24 and 6C59 variants is stronger as compared to the 3C23K when a low amount of immobilized AMHR-II recombinant protein per well is used (10 ng).

Example 11

Figure 16:
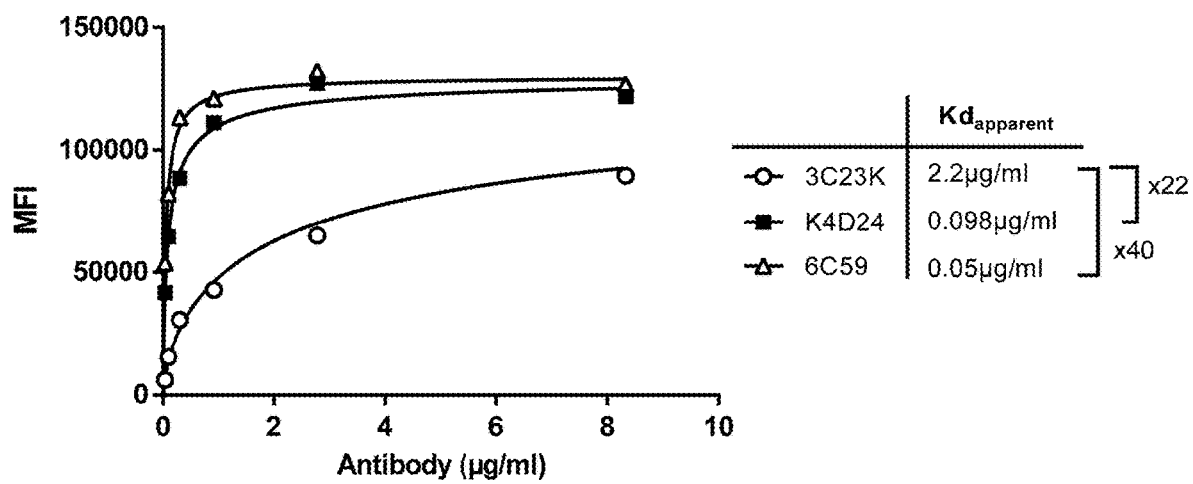
FIG. 16: Binding of the K4D24 and 6C59 compared to 3C23K antibody to the AMHR2 receptor expressed at the surface membrane of the COV434 AMHR2 transfected cell line. Binding was determined by FACS analysis in the range of concentrations 0.034 to 8 µg/ml. Binding data curves were analyzed used specific binding with Hill slope equation from GraphPad Prism. K4D24 and 6C59 variants exhibit an affinity improvement of 22 and 40 fold, respectively.
Figure 17A:
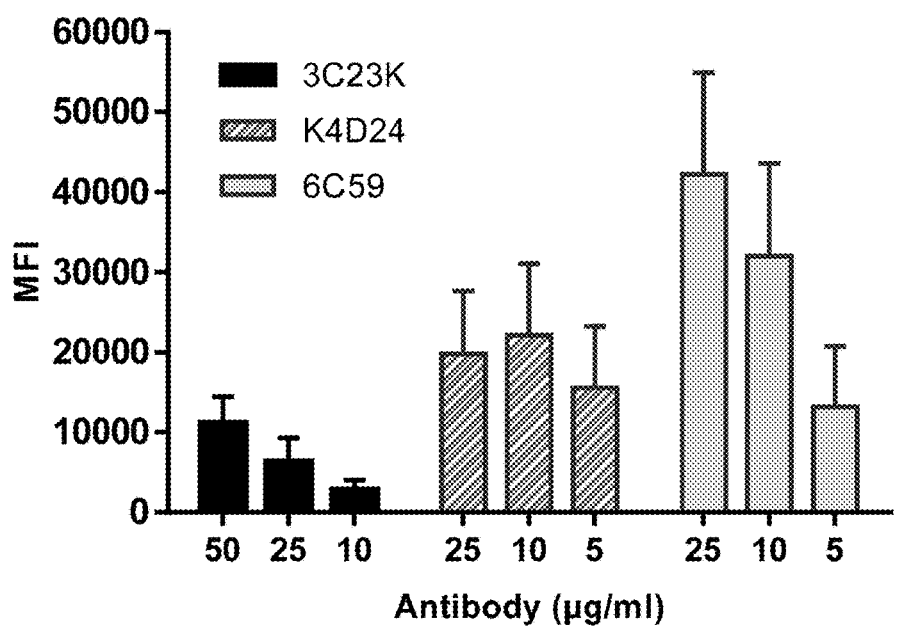
FIGS. 17A-17C: Binding of the K4D24 and 6C59 compared to 3C23K to the AMHR2 receptor expressed at the surface membrane of the COV434 WT cell line. A) Binding was determined by FACS analysis at three concentrations: 50, 25, 10 µg/ml for the 3C23K and 25, 10, 5 µg/ml for the variants. B) FACS histogram profiles of COV434WT staining at 10 µg/ml of antibodies. C) Percentage of COV434 WT cell staining with the antibodies. K4D24 and 6C59 strongly improve the level of detection of the AMHR2 receptor on the low expressing COV434 WT cell line.
Figure 17B:
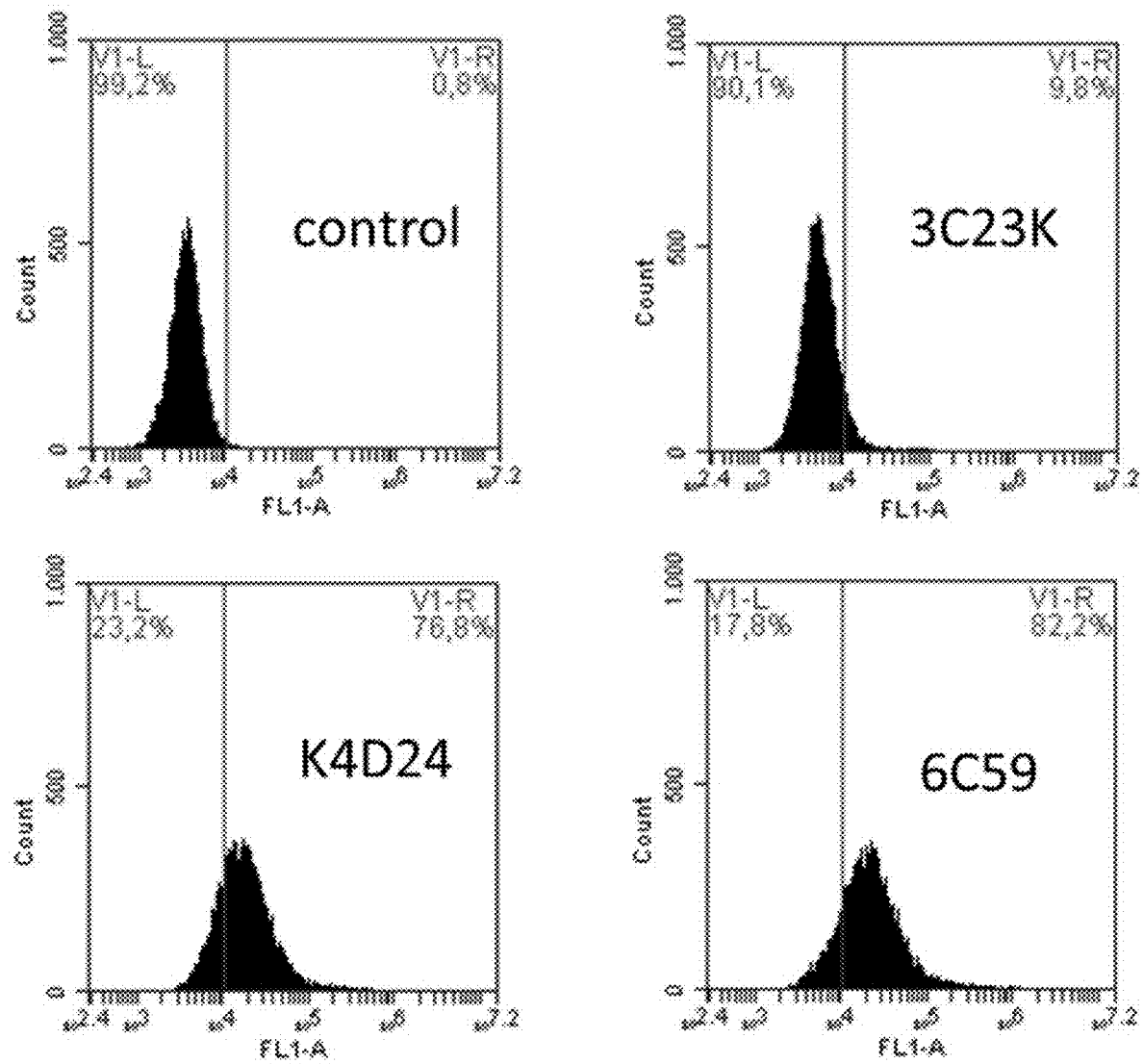
Figure 17C:
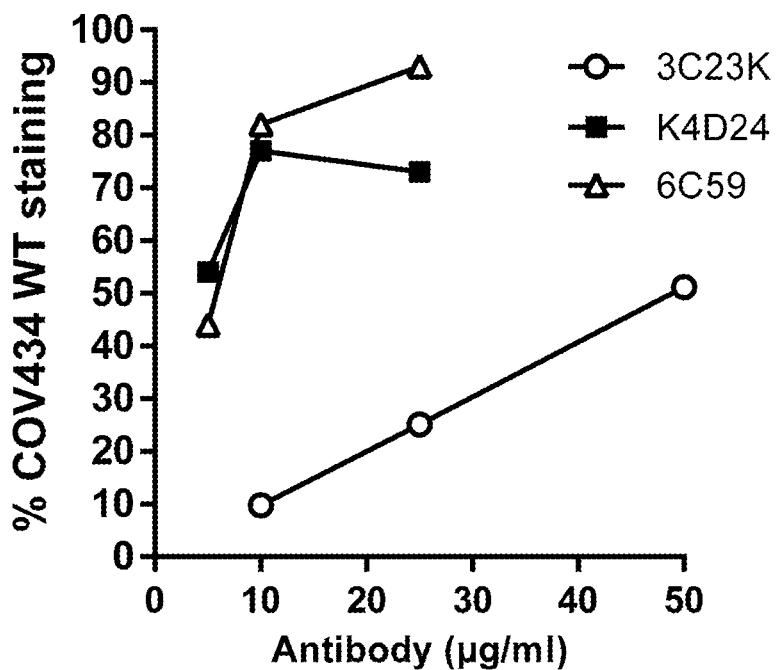

Binding of Variants Antibodies K4D24 and 6C59 to the AMHR-II Expressing Cell Lines The binding capacity of the anti-AMHR-II antibody variants K4D24 and 6C59 to the AMHR-II expressing cell lines was evaluated by flow cytometry analysis in the same manner as example 4. FACS analysis with COV434-AMHR-II transfected cell line is described in FIG. 16. The $K_{apparent}$ of the K4D24 and 6C59 variants were improved by a factor of 20 and 40 fold respectively as compared to the 3C23K (0.098 µg/ml and 0.05 µg/ml versus 2.2 µg/ml). The binding capacity of these variants was also assayed on the low expressing AMHR-II COV434 WT cell line. In this setting the binding was evaluated with three concentrations of variants (25, 10 and 5 µg/ml) and three concentrations of 3C23K (50, 25 and 10 µg/ml). As depicted in FIGS. 17A-17C, the K4D24 and 6C59 variants exhibit stronger binding as compared to 3C23K on the COV434 WT cell line. As an example, only 9.8% of COV434 WT cells are stained with the 3C23K used at 10 µg/ml, while at the same concentration, the staining with K4D24 and 6C59 increases up to 76.8% and 82.2%, respectively (FIGS. 17B and 17C).

Example 12

Figure 18:
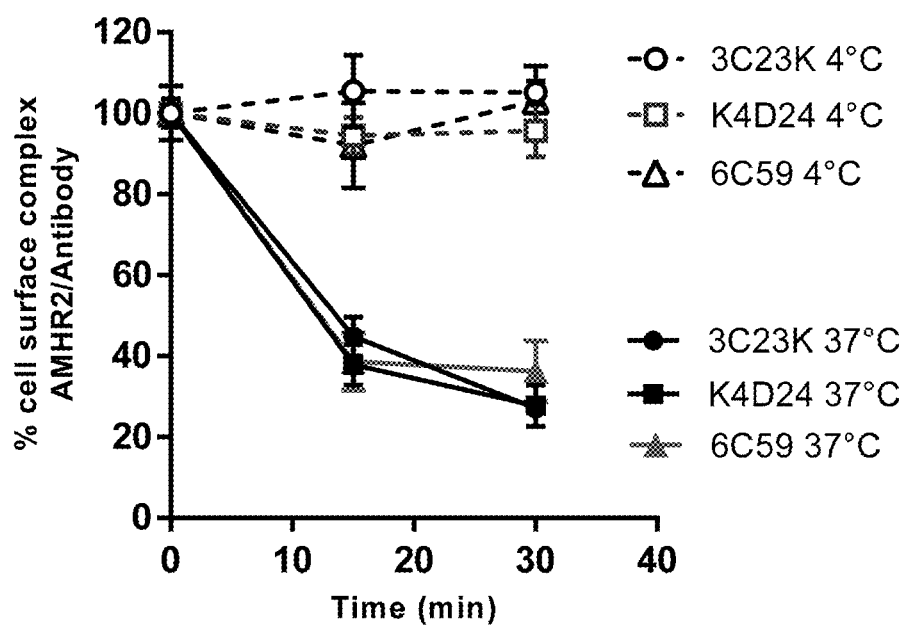
FIG. 18: Internalization of K4D24 and 6C59 compared to 3C23K evaluated by flow cytometry on COV434-AMHR2 transfected. K4D24 and 6C59 show similar internalization kinetic than 3C23K.

Evaluation of Internalization Capacity of the K4D24 and 6C59 Variants Antibodies The internalization capacity of the K4D24 and 6C59 variants was assayed by fluorescence cytometry analysis in the same manner as in Example 8 except for the concentrations used. Due to their strong binding, K4D24 and 6C59 were used at 0.5 µg/ml and 0.3 µg/ml respectively whereas the 3C23K was used at 10 µg/ml. As a result, as depicted in FIG. 18, the K4D24 and 6C59 variants antibodies were found to retain the same internalization potential as observed with the 3C23K antibody.

---

We claim:

1. An antibody drug conjugate (ADC) comprising a humanized antibody conjugated to bis-sulfone-PEG(24)-val-cit-paraaminobenzyl monomethyl auristatin E, said humanized antibody binding AMHR-II and comprising a light chain comprising SEQ ID NO: 14 and a heavy chain comprising SEQ ID NO: 16.

2. A pharmaceutical composition comprising an ADC according to claim 1, together with a pharmaceutically acceptable carrier, optionally together with an additional therapeutic agent.

3. A method of treating a patient having an anti-Mullerian hormone type II receptor (AMHR-II) expressing cancer comprising administering to the patient a pharmaceutical composition comprising a pharmaceutically effective amount of antibody drug conjugate (ADC) according to claim 1, wherein the cancer is a prostate or a gynecologic cancer.

4. The method according to claim 3, wherein said method comprises the administration of multiple doses of said ADC to said patient.

5. The method according to claim 4, wherein said ADC is administered:
   a) as a single weekly ADC dose administered for a period of up to 1 or 2 or 3 months; or
   b) consecutive once-weekly ADC doses for up to 4 weeks every 6 months for a period of up to 2 years; or
   c) one to 28 daily ADC doses for a period of up to 4 weeks; or
   d) two to seven ADC doses, administered once per day, for a period of about two weeks.

6. The method according to claim 3, wherein said method further comprises the administration of external radiotherapy, chemotherapy, cytokines or a naked antibody that specifically binds to AMHR-II.

7. The method according to 6, wherein naked antibody is administered subsequent to the administration of said ADC.

8. The method according to 7, wherein said naked antibody is administered:
   a) as a single dose every two to three months; or
   b) once weekly for a period of up to four weeks every six months with a duration of the once weekly administration that is between 1 and 4 years; or
   c) once weekly for a period of up to six months; or
   d) once per month for a period of up to 12 months; or
   e) biweekly for a period of up to 52 weeks.

9. The method according to claim 3, wherein said gynecologic cancer expressing AMHR-II is selected from ovarian cancer, metastatic ovarian cancer, or endometrial cancer.

* * * * *

SEQUENCE LISTING

```
<160> NUMBER OF SEQ ID NOS: 70

<210> SEQ ID NO 1
<211> LENGTH: 318
<212> TYPE: DNA
<213> ORGANISM: Artificial Sequence
<220> FEATURE:
<223> OTHER INFORMATION: 3C_23 VL without leader
<220> FEATURE:
<221> NAME/KEY: CDS
<222> LOCATION: (1)..(318)

<400> SEQUENCE: 1 gac atc cag atg aca cag tcc cca tct acc ctg tct gct tcc gtg gga        48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc        96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac       144
Ala Trp Tyr Gln Gln Lys Pro Gly Lys Ala Pro Lys Leu Leu Thr Tyr
        35                  40                  45 cca acc tcc tcc ctg gaa tcc ggg gtg ccc agc aga ttc tca ggc agt       192
Pro Thr Ser Ser Leu Glu Ser Gly Val Pro Ser Arg Phe Ser Gly Ser
    50                  55                  60 ggc tcc ggc acc gaa ttc acc ctg acc atc agc tca ctg cag cct gac       240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca       288
Asp Phe Ala Thr Tyr Tyr Cys Leu Gln Trp Ser Ser Tyr Pro Trp Thr
                85                  90                  95 ttc ggc ggc ggc acc aag gtg gag atc aag                               318
```

```
Phe Gly Gly Gly Thr Lys Val Glu Ile Lys
            100                 105

<210> SEQ ID NO 2
<211> LENGTH: 106
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 3
<211> LENGTH: 345
<212> TYPE: DNA
<213> ORGANISM: Artificial Sequence
<220> FEATURE:
<223> OTHER INFORMATION: 3C_23 VH without leader
<220> FEATURE:
<221> NAME/KEY: CDS
<222> LOCATION: (1)..(345)

<400> SEQUENCE: 3 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg     144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc     192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac     240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt     288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc     336
Thr Arg Gly Asp Arg Phe Ala Tyr Trp Gly Gln Gly Thr Leu Val Thr
            100                 105                 110 gtc tcg agc                                                         345
Val Ser Ser
        115
```

<210> SEQ ID NO 4
<211> LENGTH: 115
<212> TYPE: PRT
<213> ORGANISM: Artificial Sequence
<220> FEATURE:
<223> OTHER INFORMATION: Synthetic Construct

<400> SEQUENCE: 4

```
Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115
```

<210> SEQ ID NO 5
<211> LENGTH: 318
<212> TYPE: DNA
<213> ORGANISM: Artificial Sequence
<220> FEATURE:
<223> OTHER INFORMATION: 3C_23K VL without leader
<220> FEATURE:
<221> NAME/KEY: CDS
<222> LOCATION: (1)..(318)

<400> SEQUENCE: 5

```
gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac     144
Ala Trp Tyr Gln Gln Lys Pro Gly Lys Ala Pro Lys Leu Leu Thr Tyr
        35                  40                  45 cca acc tcc tcc ctg aaa tcc ggg gtg ccc agc aga ttc tca ggc agt     192
Pro Thr Ser Ser Leu Lys Ser Gly Val Pro Ser Arg Phe Ser Gly Ser
    50                  55                  60 ggc tcc ggc acc gaa ttc acc ctg acc atc agc tca ctg cag cct gac     240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca     288
Asp Phe Ala Thr Tyr Tyr Cys Leu Gln Trp Ser Ser Tyr Pro Trp Thr
                85                  90                  95 ttc ggc ggc ggc acc aag gtg gag atc aag                              318
Phe Gly Gly Gly Thr Lys Val Glu Ile Lys
            100                 105
```

<210> SEQ ID NO 6
<211> LENGTH: 106
<212> TYPE: PRT

```
<213> ORGANISM: Artificial Sequence
<220> FEATURE:
<223> OTHER INFORMATION: Synthetic Construct

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 7
<211> LENGTH: 345
<212> TYPE: DNA
<213> ORGANISM: Artificial Sequence
<220> FEATURE:
<223> OTHER INFORMATION: 3C_23K VH without leader
<220> FEATURE:
<221> NAME/KEY: CDS
<222> LOCATION: (1)..(345)

<400> SEQUENCE: 7 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg     144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc     192
Gly Trp Ile Tyr Pro Gly Asp Asp Ser Thr Lys Tyr Ser Gln Lys Phe
50                  55                  60 cag ggt cgc gtg acc att acc agg gac acc agc gcc tcc act gcc tac     240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt     288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc     336
Thr Arg Gly Asp Arg Phe Ala Tyr Trp Gly Gln Gly Thr Leu Val Thr
            100                 105                 110 gtc tcg agc                                                          345
Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: Synthetic Construct
```

-continued

<400> SEQUENCE: 8

```
Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115
```

<210> SEQ ID NO 9
<211> LENGTH: 639
<212> TYPE: DNA
<213> ORGANISM: Artificial Sequence
<220> FEATURE:
<223> OTHER INFORMATION: 3C_23 light chain without leader
<220> FEATURE:
<221> NAME/KEY: CDS
<222> LOCATION: (1)..(639)

<400> SEQUENCE: 9

```
gac atc cag atg aca cag tcc cca tct acc ctg tct gct tcc gtg gga        48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc        96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac       144
Ala Trp Tyr Gln Gln Lys Pro Gly Lys Ala Pro Lys Leu Leu Thr Tyr
        35                  40                  45 cca acc tcc tcc ctg gaa tcc ggg gtg ccc agc aga ttc tca ggc agt       192
Pro Thr Ser Ser Leu Glu Ser Gly Val Pro Ser Arg Phe Ser Gly Ser
    50                  55                  60 ggc tcc ggc acc gaa ttc acc ctg acc atc agc tca ctg cag cct gac       240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca       288
Asp Phe Ala Thr Tyr Tyr Cys Leu Gln Trp Ser Ser Tyr Pro Trp Thr
                85                  90                  95 ttc ggc ggc ggc acc aag gtg gag atc aag cgg acc gtc gcc gca cca       336
Phe Gly Gly Gly Thr Lys Val Glu Ile Lys Arg Thr Val Ala Ala Pro
            100                 105                 110 agt gtc ttc atc ttc ccg cca tct gat gag cag ttg aaa tct gga act       384
Ser Val Phe Ile Phe Pro Pro Ser Asp Glu Gln Leu Lys Ser Gly Thr
        115                 120                 125 gcc tct gtt gtg tgc ctg ctg aat aac ttc tat ccc aga gag gcc aaa       432
Ala Ser Val Val Cys Leu Leu Asn Asn Phe Tyr Pro Arg Glu Ala Lys
    130                 135                 140 gta cag tgg aag gtg gat aac gcc ctc caa tcg ggt aac tcc cag gag       480
Val Gln Trp Lys Val Asp Asn Ala Leu Gln Ser Gly Asn Ser Gln Glu
145                 150                 155                 160
```

```
agt gtc aca gag cag gac agc aag gac agc acc tac agc ctc agc agc    528
Ser Val Thr Glu Gln Asp Ser Lys Asp Ser Thr Tyr Ser Leu Ser Ser
            165                 170                 175 acc ctg acg ctg agc aaa gca gac tac gag aaa cac aaa gtc tac gcc    576
Thr Leu Thr Leu Ser Lys Ala Asp Tyr Glu Lys His Lys Val Tyr Ala
        180                 185                 190 tgc gaa gtc acc cat cag ggc ctg agc tcg ccc gtc aca aag agc ttc    624
Cys Glu Val Thr His Gln Gly Leu Ser Ser Pro Val Thr Lys Ser Phe
            195                 200                 205 aac agg gga gag tgt                                                639
Asn Arg Gly Glu Cys
    210

<210> SEQ ID NO 10
<211> LENGTH: 213
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 1335
<212> TYPE: DNA
<213> ORGANISM: Artificial Sequence
<220> FEATURE:
<223> OTHER INFORMATION: 3C_23 heavy chain without leader
<220> FEATURE:
<221> NAME/KEY: CDS
<222> LOCATION: (1)..(1335)
```

<400> SEQUENCE: 11

| | | | | | | | | | | | | | | | | |
|---|---|---|---|---|---|---|---|---|---|---|---|---|---|---|---|---|
| cag | gtg | cgg | ctg | gtg | cag | agc | ggg | gcc | gag | gtg | aag | aag | cct | gga | gcc | 48 |
| Gln | Val | Arg | Leu | Val | Gln | Ser | Gly | Ala | Glu | Val | Lys | Lys | Pro | Gly | Ala | |
| 1 | | | | 5 | | | | | 10 | | | | | 15 | | |

| tca | gtg | aag | gtg | agt | tgc | aag | gcc | tcc | ggt | tac | acc | ttc | acc | agc | tac | 96 |
|---|---|---|---|---|---|---|---|---|---|---|---|---|---|---|---|---|
| Ser | Val | Lys | Val | Ser | Cys | Lys | Ala | Ser | Gly | Tyr | Thr | Phe | Thr | Ser | Tyr | |
| | | | 20 | | | | | 25 | | | | | 30 | | | |

| cac | atc | cac | tgg | gtc | aga | cag | gct | ccc | ggc | cag | aga | ctg | gag | tgg | atg | 144 |
|---|---|---|---|---|---|---|---|---|---|---|---|---|---|---|---|---|
| His | Ile | His | Trp | Val | Arg | Gln | Ala | Pro | Gly | Gln | Arg | Leu | Glu | Trp | Met | |
| | | 35 | | | | | 40 | | | | | 45 | | | | |

| ggc | tgg | atc | tac | cct | gga | gat | gac | tcc | acc | aag | tac | tcc | cag | aag | ttc | 192 |
|---|---|---|---|---|---|---|---|---|---|---|---|---|---|---|---|---|
| Gly | Trp | Ile | Tyr | Pro | Gly | Asp | Asp | Ser | Thr | Lys | Tyr | Ser | Gln | Lys | Phe | |
| 50 | | | | | 55 | | | | | 60 | | | | | | |

| cag | ggt | cgc | gtg | acc | att | acc | agg | gac | acc | agc | gcc | tcc | act | gcc | tac | 240 |
|---|---|---|---|---|---|---|---|---|---|---|---|---|---|---|---|---|
| Gln | Gly | Arg | Val | Thr | Ile | Thr | Arg | Asp | Thr | Ser | Ala | Ser | Thr | Ala | Tyr | |
| 65 | | | | 70 | | | | | 75 | | | | | 80 | | |

| atg | gag | ctg | tct | tcc | ctg | aga | tct | gag | gat | acc | gca | gtc | tac | tac | tgt | 288 |
|---|---|---|---|---|---|---|---|---|---|---|---|---|---|---|---|---|
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |

| aca | cgg | ggg | gac | cgc | ttt | gct | tac | tgg | ggg | cag | ggc | act | ctg | gtg | acc | 336 |
|---|---|---|---|---|---|---|---|---|---|---|---|---|---|---|---|---|
| Thr | Arg | Gly | Asp | Arg | Phe | Ala | Tyr | Trp | Gly | Gln | Gly | Thr | Leu | Val | Thr | |
| | | | 100 | | | | | 105 | | | | | 110 | | | |

| gtc | tcg | agc | gcc | agc | acc | aag | ggc | cca | tcg | gtc | ttc | ccc | ctg | gca | ccc | 384 |
|---|---|---|---|---|---|---|---|---|---|---|---|---|---|---|---|---|
| Val | Ser | Ser | Ala | Ser | Thr | Lys | Gly | Pro | Ser | Val | Phe | Pro | Leu | Ala | Pro | |
| | | 115 | | | | | 120 | | | | | 125 | | | | |

| tcc | tcc | aag | agc | acc | tct | ggg | ggc | aca | gcg | gcc | ctg | ggc | tgc | ctg | gtc | 432 |
|---|---|---|---|---|---|---|---|---|---|---|---|---|---|---|---|---|
| Ser | Ser | Lys | Ser | Thr | Ser | Gly | Gly | Thr | Ala | Ala | Leu | Gly | Cys | Leu | Val | |
| | 130 | | | | | 135 | | | | | 140 | | | | | |

| aag | gac | tac | ttc | ccc | gaa | ccg | gtg | acg | gtg | tcg | tgg | aac | tca | ggc | gcc | 480 |
|---|---|---|---|---|---|---|---|---|---|---|---|---|---|---|---|---|
| Lys | Asp | Tyr | Phe | Pro | Glu | Pro | Val | Thr | Val | Ser | Trp | Asn | Ser | Gly | Ala | |
| 145 | | | | | 150 | | | | | 155 | | | | | 160 | |

| ctg | acc | agc | ggc | gtg | cac | acc | ttc | ccg | gct | gtc | cta | cag | tcc | tca | gga | 528 |
|---|---|---|---|---|---|---|---|---|---|---|---|---|---|---|---|---|
| Leu | Thr | Ser | Gly | Val | His | Thr | Phe | Pro | Ala | Val | Leu | Gln | Ser | Ser | Gly | |
| | | | | 165 | | | | | 170 | | | | | 175 | | |

| ctc | tac | tcc | ctc | agc | agc | gtg | gtg | acc | gtg | ccc | tcc | agc | agc | ttg | ggc | 576 |
|---|---|---|---|---|---|---|---|---|---|---|---|---|---|---|---|---|
| Leu | Tyr | Ser | Leu | Ser | Ser | Val | Val | Thr | Val | Pro | Ser | Ser | Ser | Leu | Gly | |
| | | | 180 | | | | | 185 | | | | | 190 | | | |

| acc | cag | acc | tac | atc | tgc | aac | gtg | aat | cac | aag | ccc | agc | aac | acc | aag | 624 |
|---|---|---|---|---|---|---|---|---|---|---|---|---|---|---|---|---|
| Thr | Gln | Thr | Tyr | Ile | Cys | Asn | Val | Asn | His | Lys | Pro | Ser | Asn | Thr | Lys | |
| | | 195 | | | | | 200 | | | | | 205 | | | | |

| gtg | gac | aag | aaa | gtt | gag | ccc | aaa | tct | tgt | gac | aaa | act | cac | aca | tgc | 672 |
|---|---|---|---|---|---|---|---|---|---|---|---|---|---|---|---|---|
| Val | Asp | Lys | Lys | Val | Glu | Pro | Lys | Ser | Cys | Asp | Lys | Thr | His | Thr | Cys | |
| | 210 | | | | | 215 | | | | | 220 | | | | | |

| cca | ccg | tgc | cca | gca | cct | gaa | ctc | ctg | ggg | gga | ccg | tca | gtc | ttc | ctc | 720 |
|---|---|---|---|---|---|---|---|---|---|---|---|---|---|---|---|---|
| Pro | Pro | Cys | Pro | Ala | Pro | Glu | Leu | Leu | Gly | Gly | Pro | Ser | Val | Phe | Leu | |
| 225 | | | | | 230 | | | | | 235 | | | | | 240 | |

| ttc | ccc | cca | aaa | ccc | aag | gac | acc | ctc | atg | atc | tcc | cgg | acc | cct | gag | 768 |
|---|---|---|---|---|---|---|---|---|---|---|---|---|---|---|---|---|
| Phe | Pro | Pro | Lys | Pro | Lys | Asp | Thr | Leu | Met | Ile | Ser | Arg | Thr | Pro | Glu | |
| | | | | 245 | | | | | 250 | | | | | 255 | | |

| gtc | aca | tgc | gtg | gtg | gtg | gac | gtg | agc | cac | gaa | gac | cct | gag | gtc | aag | 816 |
|---|---|---|---|---|---|---|---|---|---|---|---|---|---|---|---|---|
| Val | Thr | Cys | Val | Val | Val | Asp | Val | Ser | His | Glu | Asp | Pro | Glu | Val | Lys | |
| | | | 260 | | | | | 265 | | | | | 270 | | | |

| ttc | aac | tgg | tac | gtg | gac | ggc | gtg | gag | gtg | cat | aat | gcc | aag | aca | aag | 864 |
|---|---|---|---|---|---|---|---|---|---|---|---|---|---|---|---|---|
| Phe | Asn | Trp | Tyr | Val | Asp | Gly | Val | Glu | Val | His | Asn | Ala | Lys | Thr | Lys | |
| | | | 275 | | | | | 280 | | | | | 285 | | | |

| ccg | cgg | gag | gag | cag | tac | aac | agc | acg | tac | cgt | gtg | gtc | agc | gtc | ctc | 912 |
|---|---|---|---|---|---|---|---|---|---|---|---|---|---|---|---|---|
| Pro | Arg | Glu | Glu | Gln | Tyr | Asn | Ser | Thr | Tyr | Arg | Val | Val | Ser | Val | Leu | |
| | 290 | | | | | 295 | | | | | 300 | | | | | |

-continued

```
acc gtc ctg cac cag gac tgg ctg aat ggc aag gag tac aag tgc aag      960
Thr Val Leu His Gln Asp Trp Leu Asn Gly Lys Glu Tyr Lys Cys Lys
305                 310                 315                 320 gtc tcc aac aaa gcc ctc cca gcc ccc atc gag aaa acc atc tcc aaa     1008
Val Ser Asn Lys Ala Leu Pro Ala Pro Ile Glu Lys Thr Ile Ser Lys
                325                 330                 335 gcc aaa ggg cag ccc cga gaa cca cag gtg tac acc ctg ccc cca tcc     1056
Ala Lys Gly Gln Pro Arg Glu Pro Gln Val Tyr Thr Leu Pro Pro Ser
            340                 345                 350 cgg gat gag ctg acc aag aac cag gtc agc ctg acc tgc ctg gtc aaa     1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag     1152
Gly Phe Tyr Pro Ser Asp Ile Ala Val Glu Trp Glu Ser Asn Gly Gln
370                 375                 380 ccg gag aac aac tac aag acc acg cct ccc gtg ctg gac tcc gac ggc     1200
Pro Glu Asn Asn Tyr Lys Thr Thr Pro Pro Val Leu Asp Ser Asp Gly
385                 390                 395                 400 tcc ttc ttc ctc tac agc aag ctc acc gtg gac aag agc agg tgg cag     1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac     1296
Gln Gly Asn Val Phe Ser Cys Ser Val Met His Glu Ala Leu His Asn
            420                 425                 430 cac tac acg cag aag agc ctc tcc ctg tct ccg ggt aaa                 1335
His Tyr Thr Gln Lys Ser Leu Ser Leu Ser Pro Gly Lys
        435                 440                 445
```

<210> SEQ ID NO 12
<211> LENGTH: 445
<212> TYPE: PRT
<213> ORGANISM: Artificial Sequence
<220> FEATURE:
<223> OTHER INFORMATION: Synthetic Construct

<400> SEQUENCE: 12

```
Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 13
<211> LENGTH: 639
<212> TYPE: DNA
<213> ORGANISM: Artificial Sequence
<220> FEATURE:
<223> OTHER INFORMATION: 3C_23K light chain without leader
<220> FEATURE:
<221> NAME/KEY: CDS
<222> LOCATION: (1)..(639)

<400> SEQUENCE: 13 gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac     144
Ala Trp Tyr Gln Gln Lys Pro Gly Lys Ala Pro Lys Leu Leu Thr Tyr
        35                  40                  45 cca acc tcc tcc ctg aaa tcc ggg gtg ccc agc aga ttc tca ggc agt     192
Pro Thr Ser Ser Leu Lys Ser Gly Val Pro Ser Arg Phe Ser Gly Ser
    50                  55                  60
```

```
ggc tcc ggc acc gaa ttc acc ctg acc atc agc tca ctg cag cct gac    240
Gly Ser Gly Thr Glu Phe Thr Leu Thr Ile Ser Ser Leu Gln Pro Asp
 65              70                  75                  80 gac ttc gca acc tac tac tgt ctg cag tgg agt agc tac cct tgg aca    288
Asp Phe Ala Thr Tyr Tyr Cys Leu Gln Trp Ser Ser Tyr Pro Trp Thr
                 85                  90                  95 ttc ggc ggc ggc acc aag gtg gag atc aag cgg acc gtc gcc gca cca    336
Phe Gly Gly Gly Thr Lys Val Glu Ile Lys Arg Thr Val Ala Ala Pro
            100                 105                 110 agt gtc ttc atc ttc ccg cca tct gat gag cag ttg aaa tct gga act    384
Ser Val Phe Ile Phe Pro Pro Ser Asp Glu Gln Leu Lys Ser Gly Thr
        115                 120                 125 gcc tct gtt gtg tgc ctg ctg aat aac ttc tat ccc aga gag gcc aaa    432
Ala Ser Val Val Cys Leu Leu Asn Asn Phe Tyr Pro Arg Glu Ala Lys
130                 135                 140 gta cag tgg aag gtg gat aac gcc ctc caa tcg ggt aac tcc cag gag    480
Val Gln Trp Lys Val Asp Asn Ala Leu Gln Ser Gly Asn Ser Gln Glu
145                 150                 155                 160 agt gtc aca gag cag gac agc aag gac agc acc tac agc ctc agc agc    528
Ser Val Thr Glu Gln Asp Ser Lys Asp Ser Thr Tyr Ser Leu Ser Ser
                165                 170                 175 acc ctg acg ctg agc aaa gca gac tac gag aaa cac aaa gtc tac gcc    576
Thr Leu Thr Leu Ser Lys Ala Asp Tyr Glu Lys His Lys Val Tyr Ala
            180                 185                 190 tgc gaa gtc acc cat cag ggc ctg agc tcg ccc gtc aca aag agc ttc    624
Cys Glu Val Thr His Gln Gly Leu Ser Ser Pro Val Thr Lys Ser Phe
        195                 200                 205 aac agg gga gag tgt                                                 639
Asn Arg Gly Glu Cys
    210

<210> SEQ ID NO 14
<211> LENGTH: 213
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65              70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
```

```
                    145                 150                 155                 160
            Ser Val Thr Glu Gln Asp Ser Lys Asp Ser Thr Tyr Ser Leu Ser Ser
                            165                 170                 175

Thr Leu Thr Leu Ser Lys Ala Asp Tyr Glu Lys His Lys Val Tyr Ala
                            180                 185                 190

Cys Glu Val Thr His Gln Gly Leu Ser Ser Pro Val Thr Lys Ser Phe
                            195                 200                 205

Asn Arg Gly Glu Cys
                            210

<210> SEQ ID NO 15
<211> LENGTH: 1335
<212> TYPE: DNA
<213> ORGANISM: Artificial Sequence
<220> FEATURE:
<223> OTHER INFORMATION: 3C_23K heavy chain without leader
<220> FEATURE:
<221> NAME/KEY: CDS
<222> LOCATION: (1)..(1335)

<400> SEQUENCE: 15 cag gtg cgg ctg gtg cag agc ggg gcc gag gtg aag aag cct gga gcc         48
Gln Val Arg Leu Val Gln Ser Gly Ala Glu Val Lys Lys Pro Gly Ala
  1               5                  10                  15 tca gtg aag gtg agt tgc aag gcc tcc ggt tac acc ttc acc agc tac         96
Ser Val Lys Val Ser Cys Lys Ala Ser Gly Tyr Thr Phe Thr Ser Tyr
             20                  25                  30 cac atc cac tgg gtc aga cag gct ccc ggc cag aga ctg gag tgg atg        144
His Ile His Trp Val Arg Gln Ala Pro Gly Gln Arg Leu Glu Trp Met
         35                  40                  45 ggc tgg atc tac cct gga gat gac tcc acc aag tac tcc cag aag ttc        192
Gly Trp Ile Tyr Pro Gly Asp Asp Ser Thr Lys Tyr Ser Gln Lys Phe
     50                  55                  60 cag ggt cgc gtg acc att acc agg gac acc agc gcc tcc act gcc tac        240
Gln Gly Arg Val Thr Ile Thr Arg Asp Thr Ser Ala Ser Thr Ala Tyr
 65                  70                  75                  80 atg gag ctg tct tcc ctg aga tct gag gat acc gca gtc tac tac tgt        288
Met Glu Leu Ser Ser Leu Arg Ser Glu Asp Thr Ala Val Tyr Tyr Cys
                 85                  90                  95 aca cgg ggg gac cgc ttt gct tac tgg ggg cag ggc act ctg gtg acc        336
Thr Arg Gly Asp Arg Phe Ala Tyr Trp Gly Gln Gly Thr Leu Val Thr
            100                 105                 110 gtc tcg agc gcc agc acc aag ggc cca tcg gtc ttc ccc ctg gca ccc        384
Val Ser Ser Ala Ser Thr Lys Gly Pro Ser Val Phe Pro Leu Ala Pro
        115                 120                 125 tcc tcc aag agc acc tct ggg ggc aca gcg gcc ctg ggc tgc ctg gtc        432
Ser Ser Lys Ser Thr Ser Gly Gly Thr Ala Ala Leu Gly Cys Leu Val
    130                 135                 140 aag gac tac ttc ccc gaa ccg gtg acg gtg tcg tgg aac tca ggc gcc        480
Lys Asp Tyr Phe Pro Glu Pro Val Thr Val Ser Trp Asn Ser Gly Ala
145                 150                 155                 160 ctg acc agc ggc gtg cac acc ttc ccg gct gtc cta cag tcc tca gga        528
Leu Thr Ser Gly Val His Thr Phe Pro Ala Val Leu Gln Ser Ser Gly
                165                 170                 175 ctc tac tcc ctc agc agc gtg gtg acc gtg ccc tcc agc agc ttg ggc        576
Leu Tyr Ser Leu Ser Ser Val Val Thr Val Pro Ser Ser Ser Leu Gly
            180                 185                 190 acc cag acc tac atc tgc aac gtg aat cac aag ccc agc aac acc aag        624
Thr Gln Thr Tyr Ile Cys Asn Val Asn His Lys Pro Ser Asn Thr Lys
        195                 200                 205
```

```
gtg gac aag aaa gtt gag ccc aaa tct tgt gac aaa act cac aca tgc         672
Val Asp Lys Lys Val Glu Pro Lys Ser Cys Asp Lys Thr His Thr Cys
210             215                 220 cca ccg tgc cca gca cct gaa ctc ctg ggg gga ccg tca gtc ttc ctc         720
Pro Pro Cys Pro Ala Pro Glu Leu Leu Gly Gly Pro Ser Val Phe Leu
225             230                 235                 240 ttc ccc cca aaa ccc aag gac acc ctc atg atc tcc cgg acc cct gag         768
Phe Pro Pro Lys Pro Lys Asp Thr Leu Met Ile Ser Arg Thr Pro Glu
        245                 250                 255 gtc aca tgc gtg gtg gtg gac gtg agc cac gaa gac cct gag gtc aag         816
Val Thr Cys Val Val Val Asp Val Ser His Glu Asp Pro Glu Val Lys
        260                 265                 270 ttc aac tgg tac gtg gac ggc gtg gag gtg cat aat gcc aag aca aag         864
Phe Asn Trp Tyr Val Asp Gly Val Glu Val His Asn Ala Lys Thr Lys
        275                 280                 285 ccg cgg gag gag cag tac aac agc acg tac cgt gtg gtc agc gtc ctc         912
Pro Arg Glu Glu Gln Tyr Asn Ser Thr Tyr Arg Val Val Ser Val Leu
290             295                 300 acc gtc ctg cac cag gac tgg ctg aat ggc aag gag tac aag tgc aag         960
Thr Val Leu His Gln Asp Trp Leu Asn Gly Lys Glu Tyr Lys Cys Lys
305             310                 315                 320 gtc tcc aac aaa gcc ctc cca gcc ccc atc gag aaa acc atc tcc aaa        1008
Val Ser Asn Lys Ala Leu Pro Ala Pro Ile Glu Lys Thr Ile Ser Lys
        325                 330                 335 gcc aaa ggg cag ccc cga gaa cca cag gtg tac acc ctg ccc cca tcc        1056
Ala Lys Gly Gln Pro Arg Glu Pro Gln Val Tyr Thr Leu Pro Pro Ser
        340                 345                 350 cgg gat gag ctg acc aag aac cag gtc agc ctg acc tgc ctg gtc aaa        1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag        1152
Gly Phe Tyr Pro Ser Asp Ile Ala Val Glu Trp Glu Ser Asn Gly Gln
370             375                 380 ccg gag aac aac tac aag acc acg cct ccc gtg ctg gac tcc gac ggc        1200
Pro Glu Asn Asn Tyr Lys Thr Thr Pro Pro Val Leu Asp Ser Asp Gly
385             390                 395                 400 tcc ttc ttc ctc tac agc aag ctc acc gtg gac aag agc agg tgg cag        1248
Ser Phe Phe Leu Tyr Ser Lys Leu Thr Val Asp Lys Ser Arg Trp Gln
        405                 410                 415 cag ggg aac gtc ttc tca tgc tcc gtg atg cat gag gct ctg cac aac        1296
Gln Gly Asn Val Phe Ser Cys Ser Val Met His Glu Ala Leu His Asn
        420                 425                 430 cac tac acg cag aag agc ctc tcc ctg tct ccg ggt aaa                    1335
His Tyr Thr Gln Lys Ser Leu Ser Leu Ser Pro Gly Lys
435             440                 445

<210> SEQ ID NO 16
<211> LENGTH: 445
<212> TYPE: PRT
<213> ORGANISM: Artificial Sequence
<220> FEATURE:
<223> OTHER INFORMATION: Synthetic Construct

<400> SEQUENCE: 16

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile His Trp Val Arg Gln Ala Pro Gly Gln Arg Leu Glu Trp Met
            35                  40                  45
```

-continued

Gly Trp Ile Tyr Pro Gly Asp Ser Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 17
<211> LENGTH: 17
<212> TYPE: PRT

```
<213> ORGANISM: Homo sapiens
<220> FEATURE:
<221> NAME/KEY: MISC_FEATURE
<222> LOCATION: (1)..(17)
<223> OTHER INFORMATION: Anti-Mullerian Hormone type II Receptor signal
      peptide

<400> SEQUENCE: 17

Met Leu Gly Ser Leu Gly Leu Trp Ala Leu Leu Pro Thr Ala Val Glu
1               5                   10                  15

Ala

<210> SEQ ID NO 18
<211> LENGTH: 556
<212> TYPE: PRT
<213> ORGANISM: Homo sapiens
<220> FEATURE:
<221> NAME/KEY: MISC_FEATURE
<222> LOCATION: (1)..(556)
<223> OTHER INFORMATION: Anti-Mullerian Hormone type II Receptor protein
      lacking the signal peptide (mature protein)

<400> SEQUENCE: 18

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
                20                  25                  30

Pro Arg Ala Ile Arg Cys Leu Tyr Ser Arg Cys Cys Phe Gly Ile Trp
            35                  40                  45

Asn Leu Thr Gln Asp Arg Ala Gln Val Glu Met Gln Gly Cys Arg Asp
50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu Val Leu Leu Gly Leu Phe Leu Leu Leu Leu Leu Leu
130                 135                 140

Leu Gly Ser Ile Ile Leu Ala Leu Leu Gln Arg Lys Asn Tyr Arg Val
145                 150                 155                 160

Arg Gly Glu Pro Val Pro Glu Pro Arg Pro Asp Ser Gly Arg Asp Trp
                165                 170                 175

Ser Val Glu Leu Gln Glu Leu Pro Glu Leu Cys Phe Ser Gln Val Ile
            180                 185                 190

Arg Glu Gly Gly His Ala Val Val Trp Ala Gly Gln Leu Gln Gly Lys
        195                 200                 205

Leu Val Ala Ile Lys Ala Phe Pro Pro Arg Ser Val Ala Gln Phe Gln
210                 215                 220

Ala Glu Arg Ala Leu Tyr Glu Leu Pro Gly Leu Gln His Asp His Ile
225                 230                 235                 240

Val Arg Phe Ile Thr Ala Ser Arg Gly Gly Pro Gly Arg Leu Leu Ser
                245                 250                 255

Gly Pro Leu Leu Val Leu Glu Leu His Pro Lys Gly Ser Leu Cys His
            260                 265                 270

Tyr Leu Thr Gln Tyr Thr Ser Asp Trp Gly Ser Ser Leu Arg Met Ala
```

```
                275                 280                 285
Leu Ser Leu Ala Gln Gly Leu Ala Phe Leu His Glu Glu Arg Trp Gln
    290                 295                 300

Asn Gly Gln Tyr Lys Pro Gly Ile Ala His Arg Asp Leu Ser Ser Gln
305                 310                 315                 320

Asn Val Leu Ile Arg Glu Asp Gly Ser Cys Ala Ile Gly Asp Leu Gly
                325                 330                 335

Leu Ala Leu Val Leu Pro Gly Leu Thr Gln Pro Pro Ala Trp Thr Pro
            340                 345                 350

Thr Gln Pro Gln Gly Pro Ala Ala Ile Met Glu Ala Gly Thr Gln Arg
        355                 360                 365

Tyr Met Ala Pro Glu Leu Leu Asp Lys Thr Leu Asp Leu Gln Asp Trp
    370                 375                 380

Gly Met Ala Leu Arg Arg Ala Asp Ile Tyr Ser Leu Ala Leu Leu Leu
385                 390                 395                 400

Trp Glu Ile Leu Ser Arg Cys Pro Asp Leu Arg Pro Asp Ser Ser Pro
                405                 410                 415

Pro Pro Phe Gln Leu Ala Tyr Glu Ala Glu Leu Gly Asn Thr Pro Thr
            420                 425                 430

Ser Asp Glu Leu Trp Ala Leu Ala Val Gln Glu Arg Arg Arg Pro Tyr
        435                 440                 445

Ile Pro Ser Thr Trp Arg Cys Phe Ala Thr Asp Pro Asp Gly Leu Arg
    450                 455                 460

Glu Leu Leu Glu Asp Cys Trp Asp Ala Asp Pro Glu Ala Arg Leu Thr
465                 470                 475                 480

Ala Glu Cys Val Gln Gln Arg Leu Ala Ala Leu Ala His Pro Gln Glu
                485                 490                 495

Ser His Pro Phe Pro Glu Ser Cys Pro Arg Gly Cys Pro Pro Leu Cys
            500                 505                 510

Pro Glu Asp Cys Thr Ser Ile Pro Ala Pro Thr Ile Leu Pro Cys Arg
        515                 520                 525

Pro Gln Arg Ser Ala Cys His Phe Ser Val Gln Gln Gly Pro Cys Ser
    530                 535                 540

Arg Asn Pro Gln Pro Ala Cys Thr Leu Ser Pro Val
545                 550                 555
```

<210> SEQ ID NO 19
<211> LENGTH: 115
<212> TYPE: PRT
<213> ORGANISM: Artificial Sequence
<220> FEATURE:
<223> OTHER INFORMATION: 3C23K/3C23

<400> SEQUENCE: 19

```
Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

85                  90                  95

Thr Arg Gly Asp Arg Phe Ala Tyr Trp Gly Gln Gly Thr Leu Val Thr
                100                 105                 110

Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: 3C23KR/6B78

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
                100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: 5B42

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Ala Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
                100                 105                 110

Val Ser Ser
        115

<210> SEQ ID NO 22
<211> LENGTH: 115

<212> TYPE: PRT
<213> ORGANISM: Artificial Sequence
<220> FEATURE:
<223> OTHER INFORMATION: K4D-24/6C59

<400> SEQUENCE: 22

Arg Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 23
<211> LENGTH: 115
<212> TYPE: PRT
<213> ORGANISM: Artificial Sequence
<220> FEATURE:
<223> OTHER INFORMATION: K4D-20

<400> SEQUENCE: 23

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 24
<211> LENGTH: 115
<212> TYPE: PRT
<213> ORGANISM: Artificial Sequence
<220> FEATURE:
<223> OTHER INFORMATION: K4A-12

<400> SEQUENCE: 24

Gln Val Arg Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Ser Tyr

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 25
<211> LENGTH: 115
<212> TYPE: PRT
<213> ORGANISM: Artificial Sequence
<220> FEATURE:
<223> OTHER INFORMATION: K5D05

<400> SEQUENCE: 25

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: K5D-14

<400> SEQUENCE: 26

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

```
Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: K4D-123

<400> SEQUENCE: 27

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Ser Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: K4D-127/6C07

<400> SEQUENCE: 28

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Thr Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 29
```

-continued

```
<211> LENGTH: 115
<212> TYPE: PRT
<213> ORGANISM: Artificial Sequence
<220> FEATURE:
<223> OTHER INFORMATION: 5C14

<400> SEQUENCE: 29

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Phe Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 30
<211> LENGTH: 115
<212> TYPE: PRT
<213> ORGANISM: Artificial Sequence
<220> FEATURE:
<223> OTHER INFORMATION: 5C26

<400> SEQUENCE: 30

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Met Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 31
<211> LENGTH: 115
<212> TYPE: PRT
<213> ORGANISM: Artificial Sequence
<220> FEATURE:
<223> OTHER INFORMATION: 5C27

<400> SEQUENCE: 31

Gln Val Arg Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Pro Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 32
<211> LENGTH: 115
<212> TYPE: PRT
<213> ORGANISM: Artificial Sequence
<220> FEATURE:
<223> OTHER INFORMATION: 5C60

<400> SEQUENCE: 32

Gln Val Arg Leu Val Gln Ser Gly Ala Lys Val Arg Lys Pro Gly Ala
 1               5                  10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
            35                  40                  45

Gly Trp Ile Tyr Pro Gly Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 33
<211> LENGTH: 115
<212> TYPE: PRT
<213> ORGANISM: Artificial Sequence
<220> FEATURE:
<223> OTHER INFORMATION: 6C13

<400> SEQUENCE: 33

Gln Val Arg Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
            35                  40                  45

Gly Trp Ile Tyr Pro Glu Asp Asp Ser Thr Lys Tyr Ser Gln Lys Phe
        50                  55                  60

Gln Gly Arg Val Thr Ile Thr Arg Asp Thr Ser Ala Ser Thr Ala Tyr
 65                  70                  75                  80
```

```
Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: 6C18

<400> SEQUENCE: 34

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Arg Phe Ala Tyr Trp Gly Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: 6C54

<400> SEQUENCE: 35

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Pro Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115
```

```
<210> SEQ ID NO 36
<211> LENGTH: 106
<212> TYPE: PRT
<213> ORGANISM: Artificial Sequence
<220> FEATURE:
<223> OTHER INFORMATION: 3C23K

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 37
<211> LENGTH: 106
<212> TYPE: PRT
<213> ORGANISM: Artificial Sequence
<220> FEATURE:
<223> OTHER INFORMATION: L-K55E

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 38
<211> LENGTH: 106
<212> TYPE: PRT
<213> ORGANISM: Artificial Sequence
<220> FEATURE:
<223> OTHER INFORMATION: L-T48I, L-P50S

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Ile Tyr
        35                  40                  45
```

Ser Thr Ser Ser Leu Lys Ser Gly Val Pro Ser Arg Phe Ser Gly Ser
            50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105

<210> SEQ ID NO 39
<211> LENGTH: 106
<212> TYPE: PRT
<213> ORGANISM: Artificial Sequence
<220> FEATURE:
<223> OTHER INFORMATION: LT48I, L-K55E

<400> SEQUENCE: 39

Asp Ile Gln Met Thr Gln Ser Pro Ser Thr Leu Ser Ala Ser Val Gly
 1               5                  10                  15

Asp Arg Val Thr Ile Thr Cys Arg Ala Ser Ser Ser Val Arg Tyr Ile
                 20                  25                  30

Ala Trp Tyr Gln Gln Lys Pro Gly Lys Ala Pro Lys Leu Leu Ile Tyr
             35                  40                  45

Pro Thr Ser Ser Leu Glu Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: LS27P, L-S28P

<400> SEQUENCE: 40

Asp Ile Gln Met Thr Gln Ser Pro Ser Thr Leu Ser Ala Ser Val Gly
 1               5                  10                  15

Asp Arg Val Thr Ile Thr Cys Arg Ala Ser Pro Pro Val Arg Tyr Ile
                 20                  25                  30

Ala Trp Tyr Gln Gln Lys Pro Gly Lys Ala Pro Lys Leu Leu Thr Tyr
             35                  40                  45

Pro Thr Ser Ser Leu Lys Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105

<210> SEQ ID NO 41
<211> LENGTH: 106
<212> TYPE: PRT

<213> ORGANISM: Artificial Sequence
<220> FEATURE:
<223> OTHER INFORMATION: L-M4L, L-T20A

<400> SEQUENCE: 41

Asp Ile Gln Leu Thr Gln Ser Pro Ser Thr Leu Ser Ala Ser Val Gly
1               5                   10                  15

Asp Arg Val Ala Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: L-S27P

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Arg Ala Ser Pro Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 43
<211> LENGTH: 106
<212> TYPE: PRT
<213> ORGANISM: Artificial Sequence
<220> FEATURE:
<223> OTHER INFORMATION: L-M4L, L-S9P, L-R31W

<400> SEQUENCE: 43

Asp Ile Gln Leu Thr Gln Ser Pro Pro Thr Leu Ser Ala Ser Val Gly
1               5                   10                  15

Asp Arg Val Thr Ile Thr Cys Arg Ala Ser Ser Ser Val Trp Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 44
<211> LENGTH: 106
<212> TYPE: PRT
<213> ORGANISM: Artificial Sequence
<220> FEATURE:
<223> OTHER INFORMATION: L-M4L

<400> SEQUENCE: 44

Asp Ile Gln Leu Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
                20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 45
<211> LENGTH: 106
<212> TYPE: PRT
<213> ORGANISM: Artificial Sequence
<220> FEATURE:
<223> OTHER INFORMATION: L-I33T

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Thr
                20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 46
<211> LENGTH: 106
<212> TYPE: PRT
<213> ORGANISM: Artificial Sequence
<220> FEATURE:
<223> OTHER INFORMATION: L-M4L, L-K39E

<400> SEQUENCE: 46

Asp Ile Gln Leu Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Glu Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: L-T22P

<400> SEQUENCE: 47

Asp Ile Gln Met Thr Gln Ser Pro Ser Thr Leu Ser Ala Ser Val Gly
1               5                   10                  15

Asp Arg Val Thr Ile Pro Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 48
<211> LENGTH: 106
<212> TYPE: PRT
<213> ORGANISM: Artificial Sequence
<220> FEATURE:
<223> OTHER INFORMATION: L-Y32D

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Asp Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 49
<211> LENGTH: 106
<212> TYPE: PRT
<213> ORGANISM: Artificial Sequence
<220> FEATURE:
<223> OTHER INFORMATION: L-Q37H

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr His Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 50
<211> LENGTH: 106
<212> TYPE: PRT
<213> ORGANISM: Artificial Sequence
<220> FEATURE:
<223> OTHER INFORMATION: L-G97S

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Ser Gly Gly Thr Lys Val Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: L-S12P

<400> SEQUENCE: 51

-continued

Asp Ile Gln Met Thr Gln Ser Pro Ser Thr Leu Pro Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 52
<211> LENGTH: 106
<212> TYPE: PRT
<213> ORGANISM: Artificial Sequence
<220> FEATURE:
<223> OTHER INFORMATION: L-19A

<400> SEQUENCE: 52

Asp Ile Gln Met Thr Gln Ser Pro Ser Thr Leu Ser Ala Ser Val Gly
1               5                   10                  15

Asp Arg Ala Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: L-T72A

<400> SEQUENCE: 53

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
            50                  55                  60

Gly Ser Gly Thr Glu Phe Ala Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 54
<211> LENGTH: 106
<212> TYPE: PRT
<213> ORGANISM: Artificial Sequence
<220> FEATURE:
<223> OTHER INFORMATION: L-R31W

<400> SEQUENCE: 54

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Trp Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 55
<211> LENGTH: 106
<212> TYPE: PRT
<213> ORGANISM: Artificial Sequence
<220> FEATURE:
<223> OTHER INFORMATION: L-M4L, L-M39K

<400> SEQUENCE: 55

Asp Ile Gln Leu Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Met Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: L-I2N

<400> SEQUENCE: 56

Asp Asn Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 57
<211> LENGTH: 106
<212> TYPE: PRT
<213> ORGANISM: Artificial Sequence
<220> FEATURE:
<223> OTHER INFORMATION: L-G63C, L-W91C

<400> SEQUENCE: 57

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Cys Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Cys Ser Ser Tyr Pro Trp Thr
                85                  90                  95

Phe Gly Gly Gly Thr Lys Val Glu Ile Lys
            100                 105

<210> SEQ ID NO 58
<211> LENGTH: 106
<212> TYPE: PRT
<213> ORGANISM: Artificial Sequence
<220> FEATURE:
<223> OTHER INFORMATION: L-R31G

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Gly Tyr Ile
            20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 59
<211> LENGTH: 106
<212> TYPE: PRT
<213> ORGANISM: Artificial Sequence
<220> FEATURE:
<223> OTHER INFORMATION: L-I75F

<400> SEQUENCE: 59

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Phe Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 60
<211> LENGTH: 106
<212> TYPE: PRT
<213> ORGANISM: Artificial Sequence
<220> FEATURE:
<223> OTHER INFORMATION: L-I2T

<400> SEQUENCE: 60

Asp Thr Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 61
<211> LENGTH: 106
<212> TYPE: PRT
<213> ORGANISM: Artificial Sequence
<220> FEATURE:
<223> OTHER INFORMATION: L-I2T, L-K42R

<400> SEQUENCE: 61

Asp Thr Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

```
Ala Trp Tyr Gln Gln Lys Pro Gly Arg Ala Pro Lys Leu Leu Thr Tyr
             35                  40                  45

Pro Thr Ser Ser Leu Lys Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
                100                 105

<210> SEQ ID NO 62
<211> LENGTH: 106
<212> TYPE: PRT
<213> ORGANISM: Artificial Sequence
<220> FEATURE:
<223> OTHER INFORMATION: L-Y49H

<400> SEQUENCE: 62

Asp Ile Gln Met Thr Gln Ser Pro Ser Thr Leu Ser Ala Ser Val Gly
 1                   5                  10                  15

Asp Arg Val Thr Ile Thr Cys Arg Ala Ser Ser Ser Val Arg Tyr Ile
                 20                  25                  30

Ala Trp Tyr Gln Gln Lys Pro Gly Lys Ala Pro Lys Leu Leu Thr His
             35                  40                  45

Pro Thr Ser Ser Leu Lys Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
                100                 105

<210> SEQ ID NO 63
<211> LENGTH: 106
<212> TYPE: PRT
<213> ORGANISM: Artificial Sequence
<220> FEATURE:
<223> OTHER INFORMATION: L-M4L, L-T20S, L-K39E

<400> SEQUENCE: 63

Asp Ile Gln Leu Thr Gln Ser Pro Ser Thr Leu Ser Ala Ser Val Gly
 1                   5                  10                  15

Asp Arg Val Ser Ile Thr Cys Arg Ala Ser Ser Ser Val Arg Tyr Ile
                 20                  25                  30

Ala Trp Tyr Gln Gln Glu Pro Gly Lys Ala Pro Lys Leu Leu Thr Tyr
             35                  40                  45

Pro Thr Ser Ser Leu Lys Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
                100                 105

<210> SEQ ID NO 64
```

<211> LENGTH: 106
<212> TYPE: PRT
<213> ORGANISM: Artificial Sequence
<220> FEATURE:
<223> OTHER INFORMATION: L-T69P

<400> SEQUENCE: 64

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Pro Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105
```

<210> SEQ ID NO 65
<211> LENGTH: 10
<212> TYPE: PRT
<213> ORGANISM: Artificial Sequence
<220> FEATURE:
<223> OTHER INFORMATION: CDRL-1
<220> FEATURE:
<221> NAME/KEY: MISC_FEATURE
<223> OTHER INFORMATION: Xaa = Ile or Thr
<220> FEATURE:
<221> NAME/KEY: MISC_FEATURE
<222> LOCATION: (4)..(5)
<223> OTHER INFORMATION: Xaa = Ser or Pro
<220> FEATURE:
<221> NAME/KEY: MISC_FEATURE
<222> LOCATION: (7)..(7)
<223> OTHER INFORMATION: Xaa = Arg or Trp or Gly
<220> FEATURE:
<221> NAME/KEY: MISC_FEATURE
<222> LOCATION: (8)..(8)
<223> OTHER INFORMATION: Xaa = Thr or Asp
<220> FEATURE:
<221> NAME/KEY: MISC_FEATURE
<222> LOCATION: (9)..(9)
<223> OTHER INFORMATION: Xaa = Ile or Thr

<400> SEQUENCE: 65

```
Arg Ala Ser Xaa Xaa Val Xaa Xaa Xaa Ala
1               5                   10
```

<210> SEQ ID NO 66
<211> LENGTH: 7
<212> TYPE: PRT
<213> ORGANISM: Artificial Sequence
<220> FEATURE:
<223> OTHER INFORMATION: CDRL-2
<220> FEATURE:
<221> NAME/KEY: MISC_FEATURE
<222> LOCATION: (6)..(6)
<223> OTHER INFORMATION: Xaa = Lys or Glu

<400> SEQUENCE: 66

```
Pro Thr Ser Ser Leu Xaa Ser
1               5
```

```
<210> SEQ ID NO 67
<211> LENGTH: 9
<212> TYPE: PRT
<213> ORGANISM: Artificial Sequence
<220> FEATURE:
<223> OTHER INFORMATION: CDRL-3

<400> SEQUENCE: 67

Leu Gln Trp Ser Ser Tyr Pro Trp Thr
1               5

<210> SEQ ID NO 68
<211> LENGTH: 13
<212> TYPE: PRT
<213> ORGANISM: Artificial Sequence
<220> FEATURE:
<223> OTHER INFORMATION: CDRH-1
<220> FEATURE:
<221> NAME/KEY: MISC_FEATURE
<222> LOCATION: (6)..(6)
<223> OTHER INFORMATION: Xaa = Ser or Thr
<220> FEATURE:
<221> NAME/KEY: MISC_FEATURE
<222> LOCATION: (9)..(9)
<223> OTHER INFORMATION: Xaa = Ser or Gly
<220> FEATURE:
<221> NAME/KEY: MISC_FEATURE
<222> LOCATION: (10)..(10)
<223> OTHER INFORMATION: Xaa = Thr or Asn

<400> SEQUENCE: 68

Lys Ala Ser Gly Tyr Xaa Phe Thr Xaa Xaa His Ile His
1               5                   10

<210> SEQ ID NO 69
<211> LENGTH: 17
<212> TYPE: PRT
<213> ORGANISM: Artificial Sequence
<220> FEATURE:
<223> OTHER INFORMATION: CDRH-2
<220> FEATURE:
<221> NAME/KEY: MISC_FEATURE
<222> LOCATION: (5)..(5)
<223> OTHER INFORMATION: Xaa = Gly or Glu

<400> SEQUENCE: 69

Trp Ile Tyr Pro Xaa Asp Asp Ser Thr Lys Tyr Ser Gln Lys Phe Gln
1               5                   10                  15

Gly

<210> SEQ ID NO 70
<211> LENGTH: 6
<212> TYPE: PRT
<213> ORGANISM: Artificial Sequence
<220> FEATURE:
<223> OTHER INFORMATION: CDRH-3

<400> SEQUENCE: 70

Gly Asp Arg Phe Ala Tyr
1               5
```